(12) United States Patent
Murphy et al.

(10) Patent No.: US 8,268,614 B2
(45) Date of Patent: Sep. 18, 2012

(54) METHOD FOR ASSAYING CELL MOVEMENT

(75) Inventors: Christopher Murphy, Madison, WI (US); Barbara Israel, Mt Horeb, WI (US); Nicholas Abbot, Madison, WI (US)

(73) Assignee: Platypus Technologies, LLC, Madison, WI (US)

( * ) Notice: Subject to any disclaimer, the term of this patent is extended or adjusted under 35 U.S.C. 154(b) by 420 days.

(21) Appl. No.: 10/579,118

(22) PCT Filed: Nov. 10, 2004

(86) PCT No.: PCT/US2004/037656
§ 371 (c)(1),
(2), (4) Date: Feb. 26, 2007

(87) PCT Pub. No.: WO2005/047863
PCT Pub. Date: May 26, 2005

(65) Prior Publication Data
US 2007/0178534 A1  Aug. 2, 2007

Related U.S. Application Data

(60) Continuation-in-part of application No. 11/342,413, filed on Jan. 30, 2006, which is a division of application No. 10/443,419, filed on May 22, 2003, now Pat. No. 7,018,838.

(60) Provisional application No. 60/382,446, filed on May 22, 2002, provisional application No. 60/518,706, filed on Nov. 10, 2003.

(51) Int. Cl.
*C12M 1/12* (2006.01)
(52) U.S. Cl. ..................................... 435/297.5; 359/398
(58) Field of Classification Search .................... 435/30, 435/297.5; 359/398
See application file for complete search history.

(56) References Cited

U.S. PATENT DOCUMENTS

| | | | |
|---|---|---|---|
| 2,639,815 A | 5/1953 | Paluck | |
| 3,645,693 A | 2/1972 | Poziomek et al. | |
| 3,883,398 A | 5/1975 | Ono | |
| 3,910,763 A | 10/1975 | Poziomek et al. | |
| 4,068,925 A | 1/1978 | Tani et al. | |
| 4,096,086 A | 6/1978 | Kanbe et al. | |
| 4,285,697 A | 8/1981 | Neary et al. | |
| 4,551,264 A | 11/1985 | Eidenschink et al. | |
| 4,597,942 A | 7/1986 | Meathrel et al. | |
| 4,612,873 A | 9/1986 | Eberle | |
| 4,795,253 A | 1/1989 | Sandridge et al. | |
| 4,927,879 A | 5/1990 | Pidgeon | |
| 5,055,408 A | 10/1991 | Higo et al. | |
| 5,059,394 A | 10/1991 | Phillips et al. | |
| 5,063,024 A | 11/1991 | Partanen et al. | |
| 5,073,294 A | 12/1991 | Shannon et al. | |
| 5,132,226 A | 7/1992 | Dreher et al. | |
| 5,141,718 A | 8/1992 | Clark et al. | |
| 5,298,394 A | 3/1994 | Arima et al. | |
| 5,355,215 A | 10/1994 | Schroeder et al. | |
| 5,370,841 A | 12/1994 | McDonnell et al. | |
| 5,474,796 A | 12/1995 | Brennan | |
| 5,484,565 A | 1/1996 | Larsen et al. | |
| 5,599,919 A | 2/1997 | Yen et al. | |
| 5,601,980 A | 2/1997 | Gordon et al. | |
| 5,700,637 A | 12/1997 | Southern | |
| 5,801,055 A * | 9/1998 | Henderson | 435/297.5 |
| 5,858,659 A | 1/1999 | Sapolsky et al. | |
| 5,908,786 A | 6/1999 | Moreno et al. | |
| 5,925,525 A | 7/1999 | Fodor et al. | |
| 5,985,551 A | 11/1999 | Brennan | |
| 6,001,311 A | 12/1999 | Brennan | |
| 6,017,696 A | 1/2000 | Heller | |
| 6,040,193 A | 3/2000 | Winkler et al. | |
| 6,045,996 A | 4/2000 | Cronin et al. | |
| 6,051,380 A | 4/2000 | Sosnowski et al. | |
| 6,068,818 A | 5/2000 | Ackley et al. | |
| 6,171,780 B1 * | 1/2001 | Pham et al. | 435/4 |
| 6,171,802 B1 | 1/2001 | Woolverton et al. | |
| 6,201,588 B1 | 3/2001 | Walton et al. | |
| 6,242,266 B1 | 6/2001 | Schleifer et al. | |
| 6,277,489 B1 | 8/2001 | Abbott et al. | |
| 6,277,490 B1 | 8/2001 | Ruf | |
| 6,284,197 B1 | 9/2001 | Abbott et al. | |
| 6,288,392 B1 | 9/2001 | Abbott et al. | |
| 6,306,659 B1 | 10/2001 | Parce et al. | |
| 6,444,254 B1 | 9/2002 | Chilkoti et al. | |
| 6,468,657 B1 | 10/2002 | Hou et al. | |
| 6,586,257 B1 | 7/2003 | Vuong | |

(Continued)

FOREIGN PATENT DOCUMENTS
GB    2297549 A    7/1996
(Continued)

OTHER PUBLICATIONS

Gupta et al, "Optical Amplification of Ligand-Receptor Binding Using Liquid Crystals," Science vol. 279, Mar. 27, 1998 pp. 2077-2080.
Green et al., "Mechanism of the Transformation of a Stiff Polymer Lyotropic Nematic Liquid Crystal to the Cholesteric State by Dopant-Mediated ChiralInformation Transfer", J. Am. Chem. Soc., 1998. 120,9810-9817.
Seung Ryeol Kim et al. Anal. Chem "A Possible Substrate for Biomolecular Assays Based on Liquid Crystals, Analytical 2 Chemistry,"(2000) 72(19);4646-4653.
Lauer L. et al, "Spot Complaint Neuronal Networks by Structure Optimized Micro-Contact Printing" Biomaterials, Elsevier Science, 2001, vol. 22, pp. 1925-1932.

(Continued)

Primary Examiner — Ralph Gitomer
(74) Attorney, Agent, or Firm — Casimir Jones SC

(57) ABSTRACT

The present invention relates to the field of assays of cell movement. In particular, the present invention provides methods for assaying cell movement where inserts are used to confine cells to a defined area in a well of a multiwell plate and movement from the defined area is assayed.

8 Claims, 48 Drawing Sheets

U.S. PATENT DOCUMENTS

| | | | |
|---|---|---|---|
| 6,596,545 B1 | 7/2003 | Wagner et al. | |
| 6,692,699 B2 | 2/2004 | Abbott et al. | |
| 6,780,492 B2 | 8/2004 | Abbott | |
| 6,797,463 B2 | 9/2004 | Abbott et al. | |
| 6,824,837 B2 | 11/2004 | Abbott | |
| 6,844,184 B2 | 1/2005 | Kim et al. | |
| 6,849,321 B2 | 2/2005 | Abbott et al. | |
| 6,852,285 B2 | 2/2005 | Abbott et al. | |
| 6,858,423 B1 | 2/2005 | Abbott et al. | |
| 6,884,357 B2 | 4/2005 | Siddiqi | |
| 7,018,838 B2 * | 3/2006 | Murphy et al. | 435/325 |
| 7,125,592 B2 | 10/2006 | Abbott | |
| 7,135,143 B2 | 11/2006 | Abbott | |
| 7,303,694 B2 | 12/2007 | Abbott | |
| 2002/0004216 A1 | 1/2002 | Abbott et al. | |
| 2002/0028451 A1 | 3/2002 | Abbott et al. | |
| 2002/0052002 A1 | 5/2002 | Niehaus et al. | |
| 2002/0055093 A1 | 5/2002 | Abbott et al. | |
| 2002/0117412 A1 | 8/2002 | Rabiner et al. | |
| 2002/0123134 A1 | 9/2002 | Huang et al. | |
| 2002/0142453 A1 | 10/2002 | Abbott et al. | |
| 2002/0164604 A1 | 11/2002 | Abbott et al. | |
| 2002/0172621 A1 | 11/2002 | Barbera-Guillem | |
| 2002/0173033 A1 | 11/2002 | Hammerick et al. | |
| 2003/0032046 A1 | 2/2003 | Duffy et al. | |
| 2003/0049862 A1 | 3/2003 | He et al. | |
| 2003/0071949 A1 | 4/2003 | Abbott | |
| 2003/0099993 A1 | 5/2003 | Abbott et al. | |
| 2003/0124029 A1 | 7/2003 | Webb et al. | |
| 2003/0127396 A1 | 7/2003 | Siddiqi | |
| 2003/0180966 A1 | 9/2003 | Abbott | |
| 2003/0194753 A1 | 10/2003 | Abbott | |
| 2004/0002131 A1 | 1/2004 | Kim et al. | |
| 2004/0009583 A1 | 1/2004 | Benn et al. | |
| 2004/0038408 A1 | 2/2004 | Abbott et al. | |
| 2004/0091620 A1 | 5/2004 | Abbott | |
| 2004/0142411 A1 | 7/2004 | Kirk et al. | |
| 2004/0161800 A1 | 8/2004 | Abbott et al. | |
| 2004/0224380 A1 | 11/2004 | Chou et al. | |
| 2005/0064395 A1 | 3/2005 | Israel et al. | |
| 2005/0079486 A1 | 4/2005 | Abbott | |
| 2005/0079487 A1 | 4/2005 | Murphy | |
| 2005/0106562 A1 | 5/2005 | Abbott | |
| 2005/0112544 A1 * | 5/2005 | Xu et al. | 435/4 |
| 2005/0221271 A1 | 10/2005 | Murphy | |
| 2005/0260703 A1 | 11/2005 | Abbott | |
| 2006/0003389 A1 | 1/2006 | Abbott | |
| 2006/0141446 A1 | 6/2006 | Murphy et al. | |
| 2006/0252031 A1 | 11/2006 | Abbott et al. | |
| 2007/0004046 A1 | 1/2007 | Abbott | |
| 2007/0042505 A1 | 2/2007 | Abbott et al. | |
| 2007/0099249 A1 | 5/2007 | Abbott | |
| 2007/0104612 A1 | 5/2007 | Abbott | |
| 2007/0110614 A1 | 5/2007 | Abbott | |
| 2007/0231832 A1 | 10/2007 | Abbott | |
| 2007/0269848 A1 | 11/2007 | Abbott | |
| 2008/0187949 A1 * | 8/2008 | Goldbard et al. | 435/29 |
| 2009/0054262 A1 * | 2/2009 | Abbott et al. | 506/12 |

FOREIGN PATENT DOCUMENTS

| | | | |
|---|---|---|---|
| WO | WO 91/18653 A2 | | 12/1991 |
| WO | WO 99/63329 | * | 12/1999 |
| WO | WO 00/50570 A2 | | 8/2000 |
| WO | WO 01/61325 | | 2/2001 |
| WO | WO 01/61357 | | 2/2001 |
| WO | WO 02/071929 A2 | | 9/2002 |
| WO | WO 02/075294 | | 9/2002 |
| WO | WO 03/021339 | | 9/2002 |
| WO | WO 03/029481 | | 4/2003 |
| WO | WO 03/081230 | | 10/2003 |
| WO | WO 03/086197 | | 10/2003 |
| WO | WO 2004/041061 | | 5/2004 |
| WO | WO 2004/044583 | | 5/2004 |
| WO | WO 2005/010160 | | 7/2004 |
| WO | WO 03/019191 | | 8/2004 |

OTHER PUBLICATIONS

Kikuchi H E et al, "Culture of Bone-Marrow-Derived Cells in Microfabricated Pit Arrays" Proc SPIE Int Soc Opt Eng; 2001, vol. 4265, pp. 40-49.

Iwuoha E I et al: Reactivities of Organic Phase Biosensors 3: Electrochemical Study of Cytochrome P450 Cam Immobilized in a Methyltriethoysilance Sol-Gel Electroanalysis, VHC Publishers Inc. ( 2000) vol. 12, p. 980.

Skaife, Justin G et al. "Quantitative Interpretation of the Optical Textures of Liquid Crystals Caused by Specific Binding of Immunoglobulins to Surface-Bound Antugens," Langmuir (2000) 16(7):3529-3536.

Skaife, Justin G et al, "Quanitative Characterization of Obliquely Deposited Subtrates of Gold by Atomic Force Microscopy: Influence of Subtrate Topography on Anchoring of Liquid Crystals" Chemistry of Materials, V 11(3) 1999, pp. 612-623.

Vinay K. Gupta et al. "Using Droplets of Nematic Liquid Crystal to Probe the Microscopic and Mesoscopic Structure of Organic Surfaces," Langmuir 15:21 (1999) 7213-7223.

R.R. Shah et al. "Principles for Measurement of Chemical Exposure Based on Recognition-Driven Anchoring Transitions in Liquid i Crystals," Science (2001) 393(5533):1296-99.

Kleinfeld D. et al., "Controlled Outgrowth of Dissociated Neurons on Patterned Substrates," J. Neurosci. (1998) 8:4098 120.

Kumar et al. "Patterned Self-Assembled Monolayers and Meso-Scale Phenomena," Langmuir (1994) 10:1498 511.

Xia Y, "Use of Controlled Reactive Spreading of-Liquid Alkanethiol OD the Surface of Gold to Modify the Size of Features Produced by Mierocontact Printing," Whitesides, G., J. Am. Chern. Soc. (1995) 117:327475.

Hickman et al.,"Rational pattern design for in vitro cellular networks using surface photochemistry," J. Vac. Sci. Technol. (1994) 12:607 16.

Jerome, Blandine, "Surface effects and anchoring in liquid crystals," Rep. Prog. Phys. (1991) 54:391 451.

Gupta et al. Design of Surfaces for Patterned Alignment of liquid Crystals on Planar and Curved Substrates, Science (1997) 276:1533-1536.

Drawhorn et al, "Anchoring of Nematic Liquid Crystals on Self-Assembled Monolayers Formed from Alkanethiols on Semitransparent Films of Gold," J. Phys. Chem. (1995) 45:16511.

Ladam, Guy et al, "Protein Adsorption onto Auto-Assembled Polyelectrolyte Films," Langmuir (2001) 17(3):878-882.

Wagner et aL "Covalent Immobilization of Native Biomolecules onto Au(111} via N-Hydroxysuccinimide Ester Functionalized Self-Assembled Monolayers for Scanning Probe Microscopy," Biophys. J. (1996) 70:2052 2066.

Tarlov et al.,"UV Photopatterning of Alkanethiolate Monolayers," J. Am. Chem. Soc (1993) 115: 5305.

Kumar et aL, "Patterned Self-Assembled Monolayers and Meso-Scale Phenomena," Acc. Chem. Res. (1995) 28: 219.

Resler D. P et al, "High-efficiency liquid-crystal optical phased-array beam steering," Opt. Lett. (1996) 21, 689.

Stern, Margaret B, "Binary Optics: A VLSI-based microoptics technology," Microelectron. Eng. (1996) 32. 369.

Goto et aL, "Design of an Aberration-Free Spherical Micro Lens with a Diffractive Relief Grating Film on a Refractive Spherical Glass Substrate," Jpn. J. AppL Phys. (1992) 31,1586.

Magiera et aL,"Hybrid Imaging Element—Possibilities of Aberration Correction," Soc. Photo Opt. Instrum. Eng., (1996) 2774, 204.

Bernard, et al. Affinity capture of proteins from solution and their dissociation by contact printing. Nature Biotechnology. 2001; 19(9):866-869.

Renault et al. "Fabricating Microarrays of Functional Proteins Using Affinity Contact Printing." Angew. Chem. Int. Ed. 2002; 41 (13):2320-2323.

Fast, Cheap, Portable: A New Pathogen Detection Tool. Biomedical Instrumentation & Technology.2002; 36(1): 15.

Woolverton, et al. A liquid crystal biosensor for virus detection. Abstracts of the General Meeting of the American Society for Microbiology. 2002;102:110-111. (Abstract Only) (1 pg.).

Espinopza LA, Schumann KR, Luk YY, Israel BA, Abbott NL; Orientational Behavior of Thermotropic Liquid Crystals on Surfaces Presenting Electrostatically Bound Vesicular Stomatitis Virus. Langmuir Mar. 16, 2004; 20(6):2375-85.

Tingey et al. "Imaging of Affinity Microcontact Printed Proteins by Using Liquid Crystals." Langmuir.2004; 20:6816-6826.

* cited by examiner

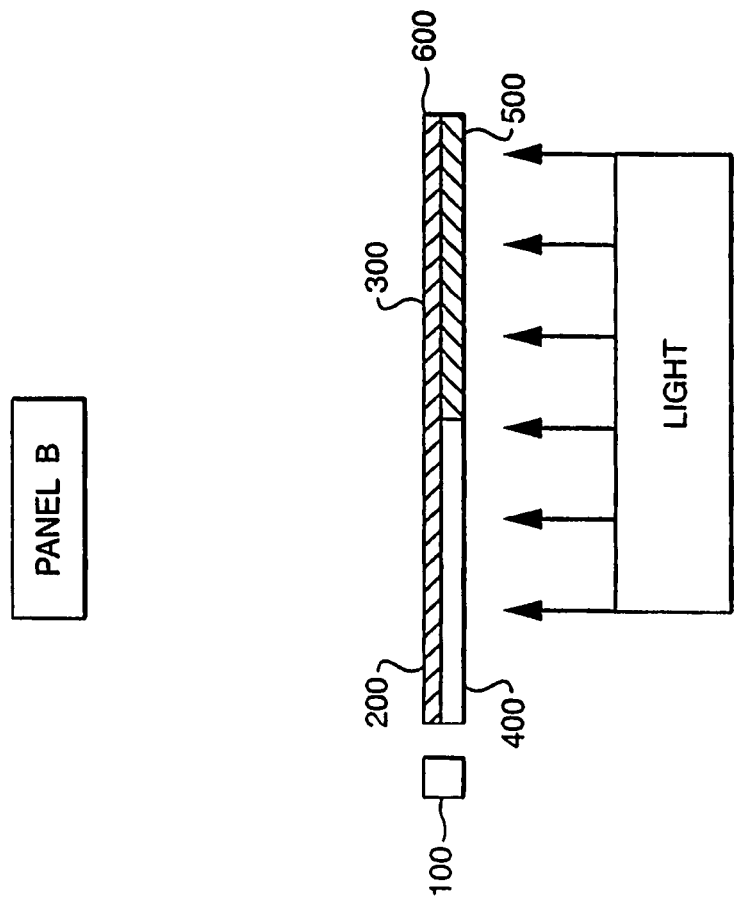
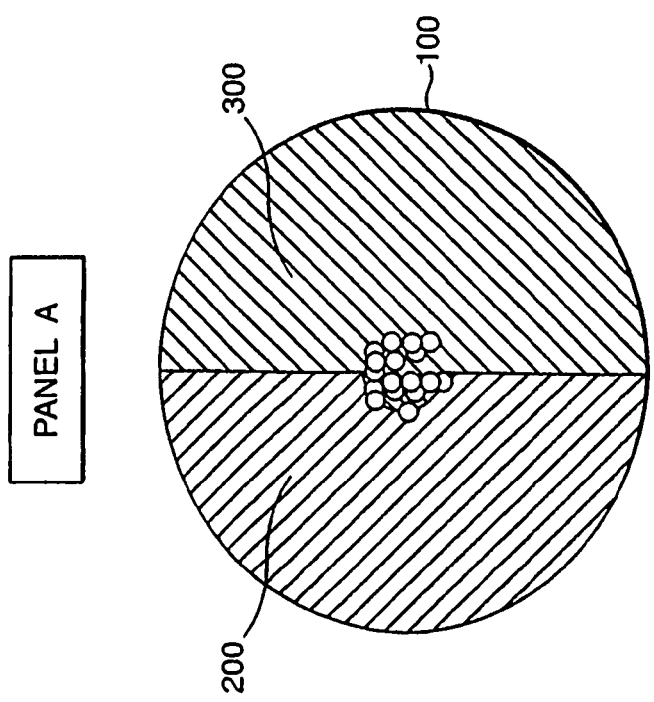
FIG. 33

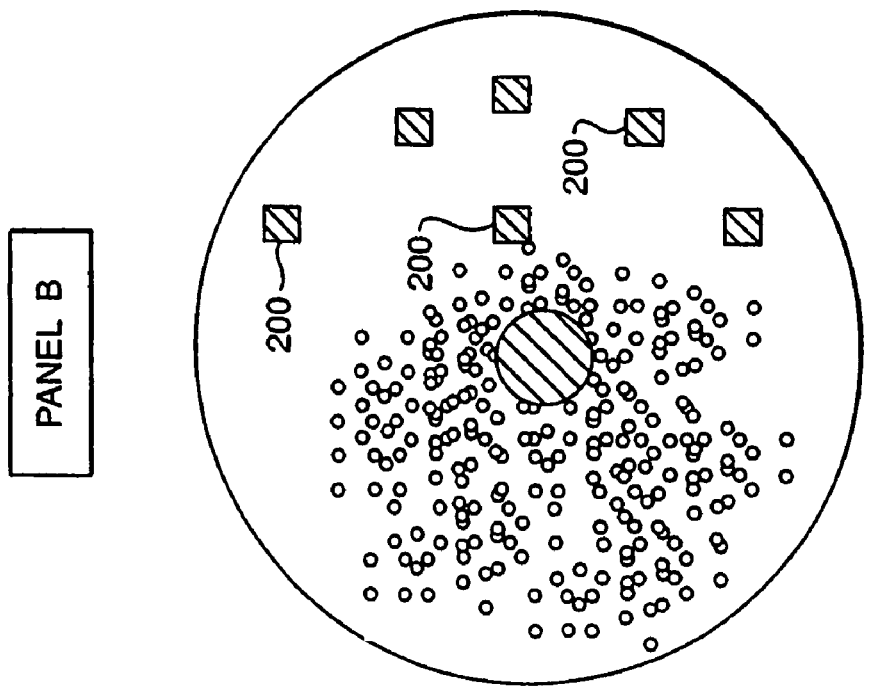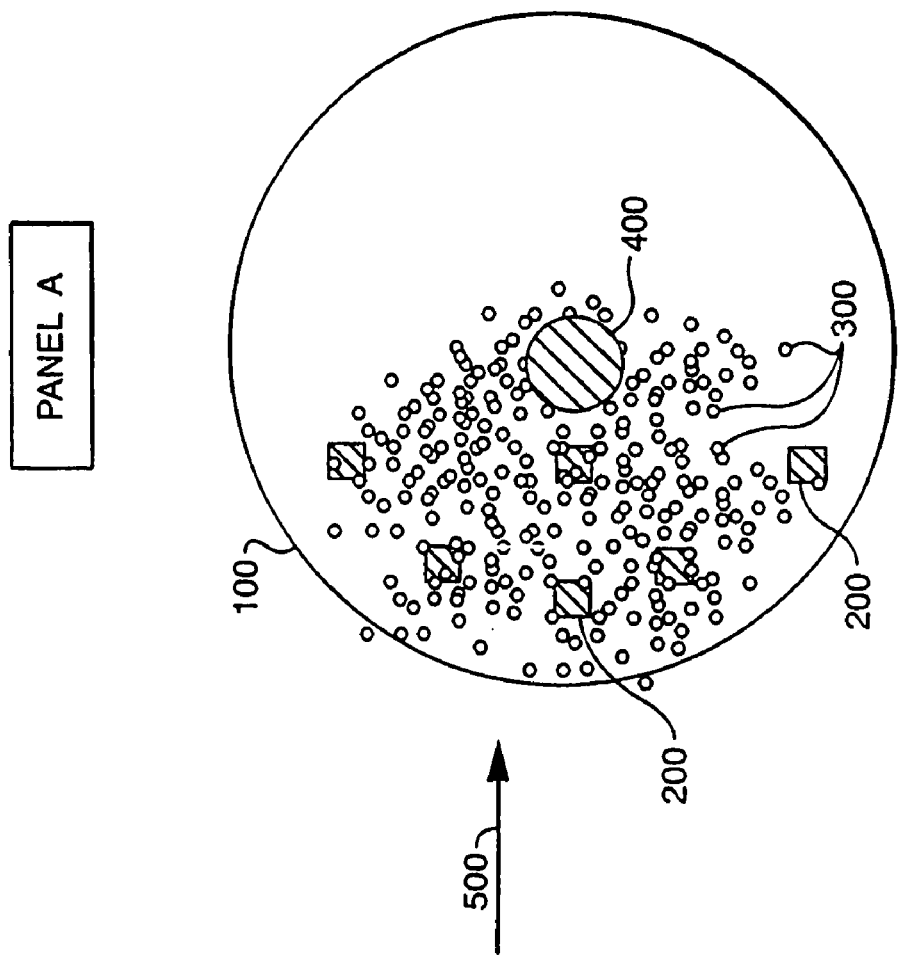
FIG. 34

Figure 54

METHOD FOR ASSAYING CELL MOVEMENT

This application is a continuation-in-part of U.S. application Ser. No. 11/342,413, filed Jan. 30, 2006, which is a divisional of U.S. application Ser. No. 10/443,419, now U.S. Pat. No. 7,018,838, filed May 22, 2003, which claims the benefit of provisional application 60/382,446, filed May 22, 2002; and this application also claims the benefit of PCT Appl. US04/37656, filed Nov. 10, 2004, which claims the benefit of provisional application 60/518,706, filed Nov. 10, 2003.

STATEMENT REGARDING FEDERALLY SPONSORED RESEARCH OR DEVELOPMENT

This Application was supported in part by the SBIR under Grant GM069026. The government has certain rights in the invention.

FIELD OF THE INVENTION

The present invention relates to the fields of molecular biology, cellular biology, developmental biology, stem cell differentiation, immunology, oncology, general laboratory sciences and microbiology, and in particular to methods and compositions based on liquid crystal assays and other biophotonically based assays for detecting and quantifying the number of cells present on a test surface or within a test substrate and the proliferation, death or movement of cells under control conditions and in response to chemotactic and other cytoactive (including compounds that are chemokinetic but not chemotactic and agents that inhibit cell migration) agents. Additionally, the present invention describes a novel biophotonic approach for the detection and quantification of enzymatic activity.

BACKGROUND OF THE INVENTION

Every year cancer claims the lives of hundreds of thousands of people worldwide. The populations of many of the heavily industrialized countries are particularly susceptible to cancer induced morbidity and mortality. In fact, cancer is the second leading cause of death in industrialized nations. For example, prostate cancer is the second most common malignancy in men. It is estimated that in 2002 in the United States nearly 180,000 men will be diagnosed with prostate cancer. Breast cancer is the most common female malignancy in most industrialized countries, and in the United States it is estimated that breast cancer will affect about 10% of women during their lives. Approximately 30 to 40% of women with operable breast cancer eventually develop metastases distant from the primary tumor.

Metastasis, the formation of secondary tumors in organs and tissues remote from the site of the primary tumor, is the main cause of treatment failure and death for cancer patients. Indeed, the distinguishing feature of malignant cells is their capacity to invade surrounding normal tissues and metastasize through the blood and lymphatic systems to distant organs. Cancer metastasis is a complex process by which certain cancer cells acquire substantial genetic mutations and perturbed signal cascades that allow them to leave the primary tumor mass and establish secondary tumors at distant sites. Metastatic cancer cells break adhesions with neighboring cells, dissolve the extracellular matrix, migrate and invade surrounding tissue, travel via the circulatory system, invade, survive and proliferate in new sites. Unfortunately, the molecular mechanisms that promote and restrain the metastatic spread of cancer cells have yet to be clearly identified.

Medical researchers have made considerable efforts to understand whether chemotactic agents are involved in metastasis and why particular cancers preferentially metastasize to certain sites. Breast cancer, for example, favors metastasizing to regional lymph nodes, bone marrow, and lung and liver tissues. Prostate cancer favors metastasizing to bone marrow. Several theories have been advanced to explain the preferential metastasis of certain cancers.

It has recently been shown that one important property of highly metastatic cells is their ability to respond to chemotactic agents such as paracrine and autocrine motility factors. For example, recent work done by Muller et al. provides evidence for chemotactic homing of breast cancer to metastatic sites. (Muller et al. "*Involvement of chemokine receptors in breast cancer metastasis*," Nature, 410:50-56 [2001]); See also, M. More, "*The role of chemoattraction in cancer metastases*," Bioessays, 23:674-676 [2001]). Muller et al. findings indicate that CXCR4 and CCR7 chemokine receptors are found on breast cancer cells and that ligands for these receptors are highly expressed at sites associated with preferential breast cancer metastases.

Many conventional assay methods have been adapted for studying the effects of chemotactic agents on cancer and other cells of interest (e.g., densitometric, analyses of membrane filters, visible spectrum or spectrophotometric ELISA microplate readers, fluorescence microplate readers, scintillation counters, and photoluminescence readers). Each of these methods has particular advantages and disadvantages. One disadvantage found in each of these methods is the requirement that the cells of interest be "tagged" with dyes, fluorescing agents, or radioisotopes, in order to observe the cellular responses to chemical agents. Extrinsic cell labeling techniques add to the expense and complexity of the existing assay methods and often requires the expertise of highly skilled technicians.

An important property of metastatic cells is their ability to produce proteases, such as Matrix Metalloproteinases (MMPs) that are capable of digesting constituents of the extracellular matrix. The elaboration of these proteases facilitates their invasion of tissues. The role of proteases in the metastatic process using in vitro and in vivo systems as well as their quantification for use as a prognostic indicator for metastatic potential has been widely reported. The amount of a given protease present can be measured using ELISA but this requires a specific antibody capable of reacting with the protease from a given species. Another drawback of ELISA is that it measures the total amount of a given protease and does not discriminate between proenzyme, activated enzyme or inhibitor complexed enzyme. For example, the activation state of MMP's in the cellular environment is tightly regulated by Tissue Inhibitors of Metalloproteinases (TIMPs). Zymography (to measure proteases) and reverse zymography (to measure TIMPs), are widely used methods that involve gel electrophoresis combined with enzymatic digestion of an appropriate substrate. Both the proenzyme and active forms of proteases can be distinguished on the basis of molecular weight. Unfortunately, standard zymographic methods are laborious requiring many preparative steps (Hawkes S P, Li H, Taniguchi T. Zymography and reverse zymography for detecting MMPs and TIMPs. In *Matrix Metalloproteinase Protocols*. Volume 151 of Methods in Molecular Biology. Ian Clark ed. Humana Press. Totowa N.J. 2001. pp 399-410).

Other assays used include a variety of protease assays including quantifying radiolabelled collagen fragments released by enzymatic cleavage of a radiolabelled substrate, and the measurement of fluorescence produced when an fluorescently autoquenched fluorescent substrate undergoes digestion and creating an increase in quantifiable fluorescent signal. These methods do not allow discrimination between proteases however (Cawston T E, Koshy P, Rowan A D. Assay of matrix metalloproteinases against matrix substrates. In Matrix Metalloproteinase Protocols. Volume 151 of Methods in Molecular Biology. Ian Clark ed. Humana Press. Totowa N.J. 2001. pp 389-397).

What are needed are assay devices and systems for detecting quantifying cell number and identifying their spatial location as well as identifying and quantifying proteases and protease inhibitors that do not require extrinsic cell labeling techniques that are robust and easier to use which allows for enhanced evaluation of samples.

SUMMARY OF THE INVENTION

The present invention relates to the fields of molecular biology, cellular biology, immunology, oncology, developmental biology, stem cell differentiation, general laboratory sciences and microbiology, and in particular to methods and compositions based on liquid crystal assays and other biophotonically based assays for detecting and quantifying the number of cells present on a substrate (allows for the quantitation of cell adhesion and cell proliferation) as well as direct quantification of proliferation, cell death, differentiation, or cell migration on a surface or through an extracellular matrix (cell invasion) under control conditions and in response to the presence of chemotactic, growth, differentiation enhancing and other cytoactive (accounts for chemokinetic agents and agents that inhibit cell migration) agents.

Accordingly, in some embodiments, the present invention provides an assay apparatus comprising a surface having at least one discreet assay region, the discrete assay region comprising at least one cell seeding region and at least one test compound formulated for controlled release. In some embodiments, the test compound formulated for controlled release is provided in a matrix. In some preferred embodiments, the matrix is a polymer. The present invention is not limited to the use of any particular type of polymer. Indeed, the use of a varieties of polymers is contemplated, including, but not limited to, chitosan, chitosan-alginate, poly(N-isopropylacrylamide) hydrogels, lipid microspheres, copolymers of polylactic and polyglycolic acid, dextran hydrogels, and poly (ethylene glycol) hydrogels. In some embodiments, the matrix further comprises an extracellular matrix component. The present invention is not limited to any particular extracellular matrix components. Indeed, the use of a variety of extracellular matrix components is contemplated, including, but not limited to, collagen, vitronectin, fibronectin, and laminin. In some preferred embodiments, the cell seeding region comprises an extracellular matrix component. The present invention is not limited to the use of any particular test compound. Indeed, the present invention contemplates the use of a variety of test compounds, including, but not limited to, polypeptides, sugars, amino acids and small molecule organic compounds. The present invention is not limited to the use of any particular polypeptides. Indeed, the use of a variety polypeptides is contemplated, including, but not limited to integrin binding sequences and growth factors. The present invention is not limited to the use of any particular carbohydrates. Indeed, the use of a variety of carbohydrates is contemplated, including, but not limited to, glucose, fructose, sucrose, galactose and derivatives thereof. The present invention is not limited to the use of any particular small molecule organic compounds. Indeed, a variety find use in the present invention, including, but not limited to, steroids, immunomodulators, hormones, antineoplastic drugs, antimetabolites, chemotherapeutic agents, antimicrobial drugs, NTHEs, vasodialators, beta-adrenergic blockers, diuretics, anesthetics, antidepressants, sedatives, tranquilizers, vasoconstrictors, anti-ulcer drugs, stimulants, antihypertensive drugs and cholesterol lowering drugs. In some preferred embodiments, the test compound is suspected of promoting or inhibiting the movement of cells. The assay regions of the devices of the present invention may be configured for a variety of readouts, including, but not limited to, colorimetric, fluorimetric, optical density, liquid crystal, and light scattering readouts. In some embodiments, the at least one cell seeding region contains at least one cell. In some embodiments, the at least one assay region is configured to orient mesogens. In some embodiments the devices comprises at least one reservoir. In some embodiments, the at least one reservoir is fluidically connected to at least one microfluidic channel. In some preferred embodiments, the at least one reservoir fluidically contacts the at least one assay region. In some embodiments, the apparatus comprises about 6, 12, 24, 36, 96, 384, or 1536 assay regions. In some embodiments, the about 6, 12, 24, 36, 96, 384, or 1536 regions are arranged in an array of a plurality of rows and columns. In some preferred embodiments, the array of assay regions is configured to correspond to the reading positions of a plate reader device. In some embodiments, the apparatus comprises two or more test compounds formulated for controlled release.

In some embodiments, the apparatus further comprising at least one well having bottom and side surfaces, wherein the at least one discreet assay region is located on the bottom surface of the well, and wherein the matrix is located in the well. The present invention is not limited to any particular matrix location. In some embodiments, the matrix is located on the side surface of the well. In other embodiments, the matrix is located on the bottom of the well. In other embodiments, the matrix is located in a discrete region of the well. In some embodiments, the discrete region is on the bottom of the well. In other embodiments, the discrete region is on the side of the well.

In some embodiments, the present invention provides methods comprising a) providing cells and an assay apparatus comprising a surface having at least one discreet assay region, the discrete assay region comprising at least one cell seeding region and at least one test compound formulated for controlled release; b) contacting the cell seeding region with the cells; c) culturing the cells under conditions that the test compound is released; and d) assaying the response of the cells to the test compound. In some embodiments, the surface comprises a plurality of discrete assay regions arranged in an array. In some embodiments, the surface comprises about 6, 12, 24, 36, 96, 384, or 1536 assay regions. In some embodiments, the about 6, 12, 24, 36, 96, 384, or 1536 assay regions are arranged in an array of a plurality of rows and columns. In some preferred embodiments, the array of the assay regions is configured to correspond to the reading positions of a plate reader device. As described above, in some embodiments, the test compound formulated for controlled release is provided in a matrix. In some embodiments, the test compound is selected from the group consisting of polypeptides, sugars, amino acids and small molecule organic compounds. In some embodiments, the test compound is suspected of promoting or inhibiting movement of the at least one cell. In some embodiments, the assay regions are configured for readouts selected from the group consisting of colorimetric, fluorimetric, optical density, and light scattering readouts. In some embodiments, the at least one cell seeding region contains at least one cell. In some embodiments, the at least one assay region is configured to orient mesogens. In some embodiments, the surface comprises reservoirs and microfluidic channels. Also, as described above, the matrix can be provided in a variety of location.

The present invention also provides kits comprising: a) an assay apparatus comprising a surface having at least one discreet assay region, the discrete assay region comprising at least one cell seeding region; b) unpolymerized matrix material; and c) instructions for polymerizing the matrix material in the presence of the at least one test compound, applying the matrix material to the assay apparatus, and culturing cells in the assay apparatus. The assay devices in the kits are substantially as described above. As above, the kits find use for the detection and analysis of variety of cells and test compounds.

In some embodiments, the present invention provides devices for facilitating the seeding of cells in a multiwell plate comprising a plurality of cylinders sized to be inserted into individual wells of a multiwell plate, the cylinders movably connected to at least one horizontal member so that the cylinders can be positioned in individual wells in the multiwell plate. In some embodiments, the movable connection allows for horizontal movement of the cylinders. In other embodiments, the moveable connection allowed for vertical movement of the cylinders. In some embodiments, the cylinders are sized to be inserted into a well of a multiwell plate selected from the group consisting of 6, 12, 24, 36, 96, 384, or 1536 well multiwell plates.

In other embodiments, the present invention provides devices for facilitating the seeding of cells in a multiwell plate comprising an inserted sized to be inserted into individual wells of multiwell plate, the insert comprising a substantially circular surface having therein an opening so that when the insert is positioned in the well the bottom surface of the well is exposed by the opening in the insert, the insert further comprising lift piece so that the insert can be lifted from the well. In some preferred embodiments, the inserts are sized to be inserted into a well of a multiwell plate selected from the group consisting of 6, 12, 24, 36, 96, 384, or 1536 well multiwell plates.

In other embodiments, the present invention provides methods of assaying cell migration comprising: a) providing cells and an assay device; b) seeding cells in a discreet area of the assay device; c) assaying cell movement with a plate reading device. In some embodiments, the assay device is a multiwell plate. In some embodiments, the assay device is a slide comprising multiple discreet assay regions. In some preferred embodiments, the plate reading device assays the presence of cells within discrete regions of the assay device. In some embodiments, the discrete regions are concentric circles. In some embodiments, the multiwell plate comprises asymmetrically masked wells. In other embodiments, the plate reader asymmetrically samples individual wells in the multiwell plate. In some embodiments, the multiple discreet assay regions are asymmetrically masked. In other embodiments, the plate reader asymmetrically samples individual assay regions on the slide.

In still other embodiments, the present inventions provides methods of analyzing surfaces comprising: a) providing a plate reading device and an article having a coated surface; b) measuring optical density at multiple discreet regions on the coated surface; and c) comparing the optical density at the multiple discreet regions to determine the uniformity of the coated surface. In some embodiments, the methods further comprise discarding articles that have less than a predetermined threshold of uniformity. In some embodiments, the plate reading device is configured to provide readings from about 6 to about 2000 discreet regions. In other embodiments, the methods further comprise presenting the comparisons graphically.

In other embodiments, the present invention provides methods for analyzing a lipid membrane containing entity comprising: a) providing: i) a sample suspected of containing of a biological entity with a lipid membrane; ii) a detection device comprising a substrate comprising at least one detection region; iii) mesogens; b) contacting the detection region with the sample; c) contacting the substrate with the mesogens, wherein the presence of the biological entity with a lipid membrane is indicated by a change in the mesogens over the detection regions and wherein the change is independent of the presence of an additional homeotropic director on the detection region. The present invention is not limited to any particular in the mesogens. In some embodiments, the change in the mesogens is selected from the group consisting of a change in color, a change in texture, a change in tilt, and homeotropic orientation. The present invention is not limited to the analysis of any particular biological entity having a lipid membrane. Indeed, the analysis of a variety of such entities is contemplated, including, but not limited to cells, a bacteria, Mycoplasma, viruses, and liposomes or combinations thereof. The present invention is not limited to the use of any particular substrate. Indeed, the use of a variety of substrates is contemplated, including, but not limited to metal films, glass, silicon, diamond and polymeric materials. The use of a variety of polymeric materials is contemplated, including, but not limited to, polyurethane, PDMS, polyimide, polystyrene, polycarbonate and polyisocyanoacrylate. The present invention is not limited to the use of any particular mesogens. Indeed, the sue of a variety of mesogens is contemplated, including, but not limited to, 4-cyano-4'-pentylbiphenyl, N-(4methoxybenzylidene)-4-butlyaniline and combinations thereof. In some embodiments, the detection region further comprises a recognition moiety that recognizes the biological entity. The present invention is not limited to any particular recognition moiety. Indeed, the use of a variety recognition components is contemplated, including, but not limited to antigen binding proteins and nucleic acids. In some preferred embodiments, the antigen binding protein is an immunoglobulin. In some embodiments, the substrate comprises a plurality of detection regions. In some embodiments, the plurality of detection regions have the same recognition moiety bound thereto. In other embodiments, the plurality of detection regions have different recognition moieties bound thereto. In further embodiments, the detection device further comprises a second substrate arranged opposite the first substrate to form a cell. In some embodiments, the change in the mesogens is detected by viewing the detection device between cross polar lenses. In some preferred embodiments, the detection region does not homeotropically orient mesogens in the absence of virus. The present invention is not limited to the analysis of any particular type of sample. Indeed, the use of a variety of samples is contemplated, including biological fluids, tissue homogenates, feces, vesicular fluids, swabs of orifices or tissues, and media in which virus has been cultured or prepared. In some preferred embodiments, the biological fluid is selected from the group consisting of cerebral-spinal fluid, urine, serum, plasma, nasal secretions, sputum, semen and saliva. In some embodiments, the homeotropic ordering is observed within 48 hours of the application of the sample to the detection region.

In some embodiments, the present invention provides devices for the detection of an entity comprising a lipid membrane, the device comprising a first substrate comprising at least one detection region having at least one recognition moiety specific for the entity comprising a lipid membrane immobilized thereon, wherein the detection region does not homeotropically orient an added mesogen in the absence of the virus. In some embodiments, the first substrate comprises a plurality of detection regions. In preferred embodiments, the devices comprise the features described in more detail above.

In some embodiments, the present invention provides kits comprising: a) a device for the detection of a entity comprising a lipid membrane comprising a first substrate comprising at least one detection region having a first recognition moiety specific for the entity comprising a lipid membrane immobilized thereon, wherein the detection region does not homeotropically orient an added mesogen in the absence of the entity comprising a lipid membrane; and b) instructions for detection of the entity comprising a lipid membrane. In some embodiments, the kits further comprise a vial containing mesogens. In other embodiments, the kits further comprise a vial comprising the entity comprising a lipid membrane for use as a positive control. In preferred embodiments, the devices included in the kit comprise the features described above.

BRIEF DESCRIPTION OF THE DRAWINGS

FIG. 33 is a schematic depiction of an assay device of the present invention.

FIG. 34 is a schematic depiction of an assay device of the present invention in use.

Figure 54:
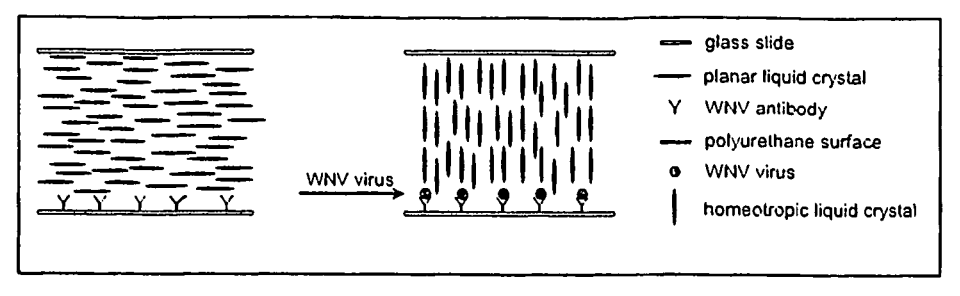

FIG. 54 provides a schematic view of an assay device of the present invention demonstrating homeotropic orientation of a liquid crystal directed by bound virus.

DEFINITIONS

Figure 1A:
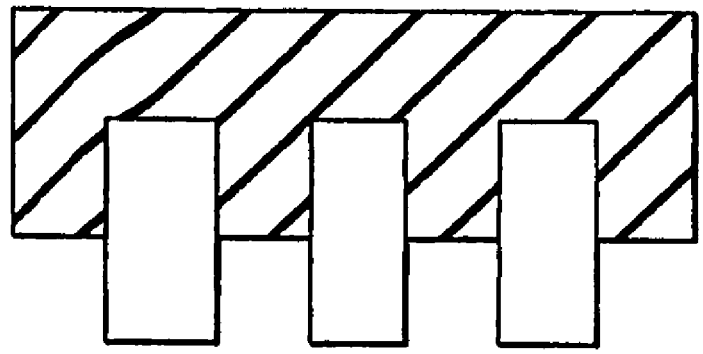
FIG. 1A is a schematic depiction of a nanostamper for use in the present invention.

As used herein, the term "substrate" refers to material capable of supporting associated assay components (e.g., assay regions, mesogens that constitute the functional units of liquid crystals, cells, test compounds, etc.). For example, in some embodiments, the substrate comprises a planar (i.e., 2 dimensional) glass, metal, composite, plastic, silica, or other biocompatible or biologically unreactive (or biologically reactive) composition. In some other embodiments, the substrate comprises a porous (e.g., microporous) or structured (i.e., 3 dimensional) composition (e.g., sol-gel matrices).

As used herein, the term "mesogen" refers to compounds that form liquid crystals, and in particular rigid, rodlike or disclike molecules that are components of liquid crystalline materials.

As used herein, "assay region" refers to a position on a substrate configured for the collection of data. In some embodiments, assay regions are configured to order mesogens. In other embodiments, assay regions are configured specifically to not order mesogens. In still further embodiments, assay regions are configured to provide two or more distinct regions (e.g., optically opaque regions and optically transparent regions, regions that are capable of ordering mesogens of liquid crystal (mesogens) and regions specifically lacking the ability to order mesogens placed on their surface, and combinations thereof).

As used herein, "array" refers to a substrate with a plurality of molecules (e.g., mesogens, recognition moieties) and/or structures (e.g., wells, reservoirs, channels, and the like) associated with its surface in an orderly arrangement (e.g., a plurality of rows and columns). In another sense, the term "array" refers to the orderly arrangement (e.g., rows and columns) of two or more assay regions on a substrate.

The term "cell seeding region" as used herein, refers to a portion of an assay region or a substrate that is configured to provide an initial attachment site for one or more cell(s) of interest. In certain preferred embodiments, the cell seeding region comprises a depression in an assay region of the substrate.

As used herein, "taxis" refers to a response in which the direction of movement is affected by an environmental cue. Clearly distinguished from a kinesis.

As used herein, "kinesis" refers to alteration in the movement of a cell, without any directional bias. Thus speed may increase or decrease (orthokinesis) or there may be an alteration in turning behavior (klinokinesis).

As used herein, "orthokinesis" refers to kinesis in which the speed or frequency of movement is increased (positive orthokinesis) or decreased (negative orthokinesis).

As used herein, the term "chemokinesis" refers to a response by a motile cell to a soluble chemical that involves an increase or decrease in speed (positive or negative orthokinesis) or of frequency of movement or a change in the frequency or magnitude of turning behavior (klinokinesis).

As used herein, the term "chemotaxis" refers to a response of motile cells or organisms in which the direction of movement is affected by the gradient of a diffusible substance. Differs from chemokinesis in that the gradient alters probability of motion in one direction only, rather than rate or frequency of random motion.

As used herein, the term "neoplasia" refers to abnormal new growth and thus means the same as tumor, which may be benign or malignant. This is now a general term used interchangeably with the term cancer, for more than 100 diseases that are characterized by uncontrolled, abnormal growth of cells. Neoplastic or cancerous cells can spread locally or through the bloodstream and lymphatic systems to other parts of the body.

As used herein, the term "migration" refers to the passing from one location to another. Used to describe the change in position of cells, microorganisms, particles or molecules.

As used herein, "cell movement" refers to any movement or change in shape of a cell including, but not limited to locomotion and cytoplasmic streaming, etc. As used herein, the term "proliferation" refers to the reproduction or multiplication of similar forms, especially of cells.

As used herein, "contraction" refers to a shortening or reduction in size of a cell. Typically associated with transduction of forces onto or into a substrate to which the cell is associated.

As used herein, the term "invasion" refers to the movement of cell(s) into a territory of differing composition. In particular it refers to the use of in vitro assay systems where cells are seeded on one substrate and they subsequently move into a 3 dimensional matrix. Ability to "invade" the 3 dimensional matrix is sometimes used as an indicator of malignant potential.

As used herein, the term "phototaxis" refers to movement of a cell or organism towards (positive phototaxis) or away from a source of light (negative phototaxis).

As used herein, the term "aerotaxis" refers to an organism's movement toward or away from oxygen as a reaction to its presence. The term is most often used when discussing aerobes (oxygen-using) versus anaerobes (which don't use oxygen).

As used herein, the term "osmotaxis" refers to movement of a cell or organism towards (positive osmotaxis) or away from (negative osmotaxis) a source of increased osmotic concentration of solutes.

As used herein, the term "immobilization" refers to the attachment or entrapment, either chemically or otherwise, of a material to another entity (e.g., a solid support) in a manner that restricts the movement of the material.

As used herein, the term "surface configured to orient mesogens" refers to surfaces that intrinsically orient mesogens (e.g., through anisotropic surface features such as obliquely deposited gold or rubbed proteins) and surfaces that are modified to orient liquid crystals by application of extrinsic structure or forces, including, but not limited to particles, electric fields, magnetic fields, or combinations thereof.

As used herein, the term "matrix" refers to any three dimensional network of materials, including, but not limited to, extracellular matrices, synthetic or biological polysaccharide matrices, collagen matrices, matrigel, polymer networks, soft microfabricated structures (e.g., from PDMS), gels of lyotropic liquid crystals, and matrices prepared from bacterial cell secretions. The materials of the matrices may be chemically crosslinked or physically crosslinked.

As used herein, the terms "material" and "materials" refer to, in their broadest sense, any composition of matter.

As used herein the term "polypeptide" is used in its broadest sense to refer to all molecules or molecular assemblies containing two or more amino acids. Such molecules include, but are not limited to, proteins, peptides, enzymes, antibodies, receptors, lipoproteins, and glycoproteins.

As used herein the term "antigen binding protein" refers to a response evoked in an animal by an immunogen (antigen), or to proteins selected in a phage display system, and to proteins derived from such proteins or glycoproteins (e.g., single chain antibodies and F(ab')2, Fab' and Fab fragments). An antibody demonstrates binding to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., VH and VL respectively), which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions. The recognition sequence may be derived from the circulating plasma of an animal or from specific in vitro culture systems (e.g., monoclonal antibodies, recombinant antibodies, and Fabs harvested from eukaryotic and prokaryotic culture systems or phage display systems).

As used herein, the term "non-specific binding" refers to the positioning (immobilization) of an analyte (target molecule, cell, parasite, virus, bacteria, particle etc) of interest on the surface, wherein the analyte that is not bound by a recognition moiety.

As used herein, the term "analytes" refers to any material that is to be analyzed. Such materials can include, but are not limited to, ions, molecules, amino acids, polypeptides, nucleic acids, antigens, bacteria, fungi, compounds, viruses, cells, prokaryotic and eukaryotic organisms, multicellular organisms, antibodies, cell parts, and particulate matter in suspension.

As used herein, the term "small organic molecule" refers to any molecule with low molecular weight (i.e., less than 10,000 atomic mass units and preferably less than 5,000 atomic mass units). Small organic molecules can, for example, bind to ligands, interact with ligands, bind to receptors, bind to nucleic acid, and bind to proteins. Small organic molecules include, but are not limited to, peptides, polypeptides, steroids, vitamins, and various organic molecules with known biological activity such as those discussed in Section III below and compounds and derivatives related thereto.

As used herein, the term "selective binding" refers to the binding of one material to another in a manner dependent upon the presence of a particular molecular structure (i.e., specific binding). For example, a receptor will selectively bind ligands that contain the chemical structures complementary to the ligand binding site(s). This is in contrast to "non-selective binding," whereby interactions are arbitrary and not based on structural compatibilities of the molecules.

As used herein, the term "conformational change" refers to the alteration of the molecular structure of a substance. It is intended that the term encompass the alteration of the structure of a single molecule or molecular aggregate (e.g., the change in structure of a receptor upon binding a ligand).

As used herein, the term "pathogen" refers to disease causing organisms, microorganisms, or agents including, but not limited to, viruses, bacteria, parasites (including, but not limited to, organisms within the phyla Protozoa, Platyhelminthes, Aschehminithes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. "Gram negative" and "Gram positive" refer to staining patterns obtained with the Gram-staining process that is well known in the art (See e.g., Finegold and Martin, Diagnostic Microbiology, 6th Ed. (1982), CV Mosby St. Louis, pp 13-15).

As used herein, the term "polymerization" encompasses any process that results in the conversion of small molecular monomers into larger molecules consisting of repeated units. Typically, polymerization involves chemical crosslinking of monomers to one another.

As used herein, the term "membrane receptors" refers to constituents of membranes that are capable of interacting with other molecules or materials. Such constituents can include, but are not limited to, proteins, lipids, carbohydrates, and combinations thereof.

As used herein, the term "volatile organic compound" or "VOC" refers to organic compounds that are reactive (i.e., evaporate quickly, explosive, corrosive, etc.), and typically are hazardous to human health or the environment above certain concentrations. Examples of VOCs include, but are not limited to, alcohols, benzenes, toluenes, chloroforms, and cyclohexanes.

As used herein, the term "enzyme" refers to molecules or molecule aggregates that are responsible for catalyzing chemical and biological reactions. Such molecules are typically proteins, but can also comprise short peptides, RNAs, DNAs, ribozymes, antibodies, and other molecules, metals and ions.

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the term "carbohydrate" refers to a class of molecules including, but not limited to, sugars, starches, cellulose, chitin, glycogen, and similar structures. Carbohydrates can also exist as components of glycolipids and glycoproteins.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the term "chelating compound" refers to any compound composed of or containing coordinate links that complete a closed ring structure. The compounds can combine with metal ions, attached by coordinate bonds to at least two of the nonmetal ions.

As used herein, the term "recognition moiety" refers to any molecule, molecular group, or molecular complex that is capable of recognizing (i.e., specifically interacting with) a molecule. For example, the ligand binding site of a receptor would be considered a molecular recognition complex. The term "recognition moiety" also encompasses binding sequences known to bind with a specific target molecule (e.g., the binding sequence of Raf 1 that specifically binds Ras) and molecules that bind metals.

As used herein, the term "cellular binding moiety" refers to any molecule, molecular group, or molecular complex that binds cells. Examples of cellular binding moieties include, but are not limited to, integrin binding sequences such as RGD sequences and other binding sequences found in extracellular matrix proteins.

As used herein, the terms "home testing" and "point of care testing" refer to testing that occurs outside of a laboratory environment. Such testing can occur indoors or outdoors at, for example, a private residence, a place of business, public or private land, in a vehicle, as well as at the patient's bedside.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses, including those incapable of replication without the presence of other viruses.

As used herein, the term "nanostructures" refers to microscopic structures, typically measured on a nanometer scale. Such structures include various three-dimensional assemblies, including, but not limited to, liposomes, films, multilayers, braided, lamellar, helical, tubular, pillar like and fiber-like shapes, and combinations thereof. Such structures can, in some embodiments, exist as solvated polymers in aggregate forms such as rods and coils. Such structures can also be formed from inorganic materials, such as prepared by the physical deposition of a gold film onto the surface of a solid, proteins immobilized on surfaces that have been mechanically rubbed, polymeric materials that have been mechanically rubbed, polymeric or metallic surfaces into which order has been introduced onto its surface by the use of micro and nanoabrasive materials (nanoblasting), high pressure water etching, and polymeric materials that have been molded or imprinted with topography by using a silicon template prepared by electron beam or other lithographic processes. Extrinsically structured anisotropic surfaces can also be formed by the placement of submicron to 10 µm sized particles (anisometric and/or isometric depending on the method used) and aligning or partially aligning the particles through the use of external fields (including, but not limited to, electric fields, magnetic fields, shear fields and/or fluid flow). It is also possible to create an aligned surface using mechanical transfer of organized or aligned particles (e.g., fabrication with a hydrophobic stamp containing the desired topography). The particles, when deposited onto the surface are organized or aligned such that mesogens contained within an overlying liquid crystal are aligned. These particles are displaced or reoriented when cells grow on the surface. Alternatively, the stamp can be made from friable materials that are transferred to the substrate upon contact with the substrate. Examples of such transferable materials include, but are not limited to, charcoal, chalk, soapstone, graphite, pumice, other easily fragmented and transferred materials and synthetic laminated material, prepared such that fracturing layers are designed into the material. Nanostructured substrates can also be fabricated using scanning probe methods, including atomic force microscopy and scanning tunneling microscopy, as well as x-ray lithography, micro/nanoabrasive methods, interferometric optical lithographic methods, and imprinting and embossing (including hot and cold embossing). Similarly, order can be introduced into a particle covered surface whereby particles are initially randomly positioned across a surface and an ordered pattern introduced by the selective removal of particles.

As used the term "multilayer" refers to structures comprised of two or more monolayers. The individual monolayers may chemically interact with one another (e.g., through covalent bonding, ionic interactions, van der Waals' interactions, dipole bonding, hydrogen bonding, hydrophobic or hydrophilic assembly, and steric hindrance) to produce a film with novel properties (i.e., properties that are different from those of the monolayers alone).

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g., a single lipid molecule) and small molecular assemblies (e.g., polymerized lipids), whereby the individual small molecular assemblies can be further aggregated (e.g., assembled and polymerized) into larger molecular assemblies.

As used herein, the term "ligands" refers to any ion, molecule, molecular group, or other substance that binds to another entity to form a larger complex. Examples of ligands include, but are not limited to, peptides, carbohydrates, nucleic acids, antibodies, or any molecules that bind to receptors.

As used herein, the terms "organic matrix" and "biological matrix" refer to collections of organic molecules that are assembled into a larger multi-molecular structure. Such structures can include, but are not limited to, films, monolayers, and bilayers. As used herein, the term "organic monolayer" refers to a thin film comprised of a single layer of carbon-based molecules. In one embodiment, such monolayers can be comprised of polar molecules whereby the hydrophobic ends all line up at one side of the monolayer. The term "monolayer assemblies" refers to structures comprised of monolayers. The term "organic polymetric matrix" refers to organic matrices whereby some or all of the molecular constituents of the matrix are polymerized.

As used herein, the term "linker" or "spacer molecule" refers to material that links one entity to another. In one sense, a molecule or molecular group can be a linker that is covalently attached to two or more other molecules (e.g., linking a ligand to a self-assembling monomer).

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., C—C). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "ultraviolet irradiation" refers to exposure to radiation with wavelengths less than that of visible light (i.e., less than approximately 360 nm) but greater than that of X-rays (i.e., greater than approximately 0.1 nm). Ultraviolet radiation possesses greater energy than visible light and is therefore, more effective at inducing photochemical reactions.

As used herein, the term "badge" refers to any device that is portable and can be carried or worn by an individual working in an analyte detecting environment.

As used herein, the term "biological organisms" refers to any carbon-based life forms.

As used herein, the term "in situ" refers to processes, events, objects, or information that are present or take place within the context of their natural environment.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids (including lacrimal and salivary secretions as well as urinary samples), solids, tissues, cells, and gases. Biological samples include blood products, such as plasma, serum and the like. Biological samples also include specimens obtained in the course of laboratory investigations and include cells in media, bacteria, fungi, parasites and/or virus in media and particulate matter in suspension. Environmental samples include environmental material such as surface matter, soil, water, crystals and industrial samples. These examples are not to be construed as limiting the sample types applicable to the present invention.

As used herein, the term "liquid crystal" refers to a thermodynamic stable phase characterized by anisotropy of properties without the existence of a three-dimensional crystal lattice, generally lying in the temperature range between the solid and isotropic liquid phase.

As used herein, "thermotropic liquid crystal" refers to liquid crystals that result from the melting of mesogenic solids due to an increase in temperature. Both pure substances and mixtures form thermotropic liquid crystals.

"Lyotropic," as used herein, refers to molecules that form phases with orientational and/or positional order in a solvent. Lyotropic liquid crystals can be formed using amphiphilic molecules (e.g., sodium laurate, phosphatidylethanolamine, lecithin). The solvent can be water.

As used herein, the term "heterogeneous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample. Chiral nematic crystals show a strong optical activity that is much higher than can be explained on the bases of the rotatory power of the individual mesogens. When light equal in wavelength to the pitch of the director impinges on the liquid crystal, the director acts like a diffraction grating, reflecting most and sometimes all light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals which are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti-ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exists in a complicated, orientationally ordered twisted structure. The distance between these defects is hundreds of nanometers, so these phases reflect light just as crystals reflect x-rays.

"Discotic phases" are formed from molecules that are disc shaped rather than elongated. Usually these molecules have aromatic cores and six lateral substituents. If the molecules are chiral or a chiral dopant is added to a discotic liquid crystal, a chiral nematic discotic phase can form.

As used herein, the term "virus recognition moiety" refers to any compound that binds specifically to a virus. Examples of "virus recognition moieties" include, but are not limited to antigen binding proteins and nucleic acid aptamers.

As used herein, the term "homeotropic director" refers to a topographical feature (e.g., a nanostructure) of a substrate that homeotropically orients a liquid crystal.

As used herein, the term "pathogen" refers to disease causing organisms, microorganisms, or agents including, but not limited to, viruses, bacteria, parasites (including, but not limited to, organisms within the phyla Protozoa, Platyhelminthes, Aschehminithes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), CV Mosby St. Louis, pp 13-15).

As used herein, the term "lipid membrane" refers to, in its broadest sense, a thin sheet or layer comprising lipid molecules. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterol and/or other components. As used herein, the term "membrane fragment" refers to any portion or piece of a membrane.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "liposome" refers to artificially produced spherical lipid complexes that can be induced to segregate out of aqueous media.

GENERAL DESCRIPTION OF THE INVENTION

The present invention relates to the fields of molecular biology, cellular biology, immunology, oncology, developmental biology, stem cell growth and differentiation, general laboratory science, and microbiology, and in particular to methods and compositions based on liquid crystal assays and other biophotonic assays for detecting and quantifying the presence of cells, cell secretory products including polypeptides and enzymes, microorganisms (including but not limited to viruses, bacteria, fungi and parasites) and particulate matter on a substrate. The ability to correlate an output signal with cell number makes the devices of the present invention widely useful for assays of cell adhesion as well as cell proliferation, cell death and cellular differentiation. Additionally, methods are described that allow quantification of movement of cells in response to cytoactive agents as well as under control conditions. Compounds that promote cell migration may be chemotactic (e.g., compounds that stimulate directed cell migration in response to a gradient) or chemokinetic (e.g., compounds that stimulate cell migration that is not gradient or directionally dependent) agents. Additionally, inhibition of cell migration may be quantified. It is contemplated that adhesion is indicative of a change in functionality of the cell. Indeed, adhesion represents a first essential step in cell migration. Adhesion is also a requirement for survival and subsequent proliferation of anchorage dependent cell types such as fibroblasts and epithelial cells. For example, adhesion documents an essential change in leukocytes that participate subsequently in diapedesis and is an essential component of wound healing.

It is contemplated that proliferation is indicative of normal growth and/or replacement of effete cells in the maintenance of homeostasis. Proliferation is also a fundamental aspect of neoplasia and an essential component of wound healing, ontogeny, inflammation and the immune response. Adhesion, migration, differentiation and proliferation are fundamental cell behaviors that are modulated by soluble factors (e.g., cytokines, chemokines, neuropeptides, neurotrophins, polypeptide growth factors) as well as by the extracellular matrix constituents (e.g., collagens, laminin, vitronectin, fibronectin) and influenced by other cells and their products in the environment. Examining how these processes are modulated in vitro provides insights into normal physiologic processes, assists in elucidating the impact of factors in isolation and in combination with each other and allows dissection of disease processes such as neoplasia.

The present invention provides devices and methods for the determination of cell number in combination with cell proliferation and cell adhesion assays. As such, the present invention provides a single platform to multiple cell assays, including, but not limited to, adhesion, migration, proliferation, invasion, death, differentiation and contraction assays. Therefore, the devices and methods of the present invention provide distinct advantages over and complement methods including direct cell counting using microscopy and a hemocytometer or automated cell counting devices (e.g., a Coulter counter); colorimetric assays that utilize substrate conversion by intracellular enzymes (e.g., MTT assays); direct colorimetric assays based on extraction of dyes (and subsequent quantification) after initial vital staining of cells; fluorometric assays based on enzymatic conversion (e.g., Calcein AM—molecular probes that provides a fluorometrically converted substrate for intracellular esterases; fluorometric assays based on DNA binding (e.g. Hoechst dyes); colorimetric or fluorometric assays based on identification of intracellular correlative indicators of cell proliferation such as detection of Proliferating Cell Nuclear Antigen (PCNA); BRDU labeling of DNA and examining by microscopy; radiometric assays based on incorporation of tritiated thymidine; and flow cytometry with propidium iodide labeling.

Accordingly, in some embodiments the invention contemplates the placement of any analyte (particles, virus, bacteria, fungi, parasites, cells, proteins including enzymes) onto an ordered surface such that liquid crystals placed on top are prevented from accessing the ordering influence of the underlying substrate. Thus, the presence of the analyte is revealed in a non-specific manner. In other embodiments, the presence of an analyte will interfere with (disrupt) the ordering influence of an electrical and/or magnetic field. In still other embodiments of the invention, the presence of the analyte changes the structure of the surface such that the ordering influence of the surface on the liquid crystals is changed. In other embodiments, the spatial and orientational order of the bound analytes is of a type such that the presence of the analyte introduces order into the liquid crystal.

The present invention further contemplates the use of liquid crystal films to report and amplify changes in the order of an underlying substrate. While not limited to any particular mechanism, it is believed that this phenomenon is a result of the introduction of order into a mesogenic layer deposited onto a disordered substrate, or conversely, the introduction of disorder into a mesogenic layer deposited on an ordered substrate. It is contemplated that the order (or disorder) in a substrate is generated by the regular (or irregular) occurrence of nanostructures, microstructures or molecules on the substrate.

An aligned (ordered) surface can be created using a wide variety of techniques including oblique deposition of gold, simple rubbing of polymeric surfaces or by the rubbing of proteins covalently bound to a variety of surfaces, micromolding of polymers, micro/nanoabrasive processing of surfaces, lithographic methods of fabrication, including optical lithography, electron beam lithography and x-ray lithography. Additionally, LCs can be ordered on isotropic surfaces that support particles that have been oriented or organized in an anisotropic fashion. Any biologic event that imparts order to a disordered surface or disorder to an ordered surface (including isotropic surfaces that support particles that have been oriented or organized in an anisotropic fashion) is readily detected by the use of liquid crystals. In certain embodiments, the nanostructures are chemical moieties, including but not limited to, polypeptides and proteins, nucleic acids, lipids, phospholipids, carbohydrates, ions, organic molecules and inorganic molecules, and the like. In certain other embodiments, the nanostructures are physical features in the substrate surface produced by photolithography, electron beam lithography, micromolding, scanning probe methods including atomic force microscopy and scanning tunneling microscopy, photoetching, chemical etching, microcontact printing, chemical spotting, mechanical abrasives, high pressure water etching and the like.

In preferred embodiments, the surface order is created by rubbing a polymeric surface or a surface that has had one or more proteins and/or other biological moieties (e.g., sugars, specific receptors or cell receptor recognition sequences [e.g., RGD]) covalently bound to it. In other embodiments, the surface is doped with submicron to 10 μm sized particles (particles can be anisometric and/or Isometric depending on the method used) and aligning or partially aligning them through the use of external fields (including but not limited to electric fields, magnetic fields, shear fields and/or fluid flow). The particles can also be delivered to the surface by microcontact printing the particles from a topographically textured stamp. The topography of the stamp can align and order the particles prior to their transfer to the surface.

Accordingly, the present invention contemplates that the orientation of magnetic micro-nanoparticles can be manipulated (e.g., ordered) by controlled application of a magnetic field or electrical current. In some embodiments, the nanostructures on a substrate surface are produced by a combination of the physical methods.

The present invention contemplates that the changes in the local order (or disorder) of the mesogenic layer result from physically perturbing the layer. The change in order of the surface is readily observed with placement of a thin layer of liquid crystal and the use of polarizers or specific wavelengths of light and photodiode or a charge coupled device (CCD). The change in order of the surface could be either localized and discreet in nature or generalized.

In some embodiments, the perturbations are caused by the migration of cells across the surface. In other embodiments, the perturbations are caused by the adhesion, proliferation, morphological changes, loss and/or contraction of cells on the surface. In some of these embodiments, the cell membrane is intact, while in other embodiments the cell membrane is solubilized. In some embodiments, where cellular functions (e.g., cellular motility, adhesion, proliferation, apoptosis) are being assayed, the secretion of cellular factors that alter (e.g., adhere to) the surface may change local surface order. In some embodiments, liquid crystalline membranes are used to nonspecifically report biomechanical transduction events associated with cell adhesions, migration and contraction. It is contemplated that these assays function by a change of order in the crystalline membrane itself. For example, one such contemplated assay material is a film of liquid crystal that spontaneously adsorbs phospholipids at its surface. In another embodiment, an elastomeric liquid crystalline material is used. In yet another embodiment, a polymer-stabilized or polymer-dispersed liquid crystal is used.

Preferred embodiments of the present invention are directed to assays for quantitating the effects of chemotactic and chemokinetic agents as well as inhibitors of cell migration on cells (e.g., cancer cells). The present invention is not limited however to providing assays for quantitating the effects of agents suspected of being involved in cancer formation and metastasis on cellular functions and motility.

Many motility factors for cancer cells and non-malignant cells were described first as being growth factors. A motility factor converts a static, adherent cell to a motile status, a transition that is characterized by the appearance of membrane ruffling, lamellae, filopodia and pseudopodia. Several motility factors have been described for cancer cells including: (1) autocrine motility factor (AMF) which stimulates chemokinesis and chemotaxis of metastatic melanoma cells in an autocrine fashion; (2) autotaxin; (3) scatter factor/hepatocyte growth factor (e.g., ligands for the c-met oncogene product, a tyrosine kinase receptor family member); (4) TGF-α and EGF; (5) insulin like growth factors; and (6) constituents of the extracellular matrix such as fibronectin; 7) PDGF; 8) LPA; 9) amphiregulin; and 10) chemokines. These factors stimulate chemokinesis and chemotaxis. The present invention specifically contemplates assays for detecting and quantifying the effects of one or more of these motility factors on cancer cell (and non-cancer cell) motility.

While metastatic cancer cells are thought to rely upon the processes of cell adhesion, deformability, motility, and receptor recognition for creating metastases, none of these processes are unique to metastatic cancer cells. These processes have been observed in numerous non-cancerous cell types and cellular processes (e.g., trophoblast implantation, mammary gland involution, embryonic morphogenesis, hematopoietic stem cells, and tissue remodeling).

Thus, certain embodiments of the present invention are directed to assays for quantifying the effects of potential cytoactive agents (e.g., mitogenic, growth inhibiting, chemotactic, and chemokinetic agents, inhibitors of cell migration, as well as agents that promote or inhibit cell adhesion, death, or differentiation) on cell types involved in fertility and conception, stem cell differentiation and proliferation, gene therapy and cell targeting, immunology, and diseases characterized by abnormal cell motility or migration. Certain other embodiments provide assays for quantitating the effects of cytoactive agents on bacteria, archaea, and eukarya. In certain embodiments the cytoactive agent being assayed is an attractant (e.g., positive chemotactic agent) of one or more cell types. In certain other embodiments the agent is a stimulant to cell migration but is non-directional in its effects (e.g., a chemokinetic agent). In certain other embodiments the cytoactive agent is an inhibitor or repellent of one or more cell types. In some embodiments, and in particular those embodiments directed to assays employing bacteria and archaea cells, potential tactic agents include, but are not limited to, phototaxis, aerotaxis, or osmotaxis agents, and the like.

The present invention also provides devices and methods for using liquid crystals to determine the metabolic states of cells, for detecting secretory products of cells, for analyzing the structure of cell cytoskeletons, and for analyzing and measuring cell invasion into matrices. In particularly preferred embodiments, the present invention provides matrices that comprise a liquid crystal component and matrices that orient liquid crystals. In other preferred embodiments, the substrate itself is a liquid crystal. Each of these embodiments is described in more detail below. It will be recognized that many of the exemplary assay devices are not limited to use with liquid crystal display methodology. In particular, many of the devices and methods are useful with detection methodologies, including but not limited to fluorimetry, densitometry, colorimetry, and radiometry.

DETAILED DESCRIPTION OF THE INVENTION

The present invention relates to the fields of molecular biology, cellular biology, immunology, oncolocy, cellular differentiation, general laboratory science and microbiology, and in particular to methods and compositions based on liquid crystal assays and other biophotonic assays for detecting and quantifying the presence of cells on a substrate, for the detection and quantification of cell secretory products including enzymes and the quantification of fundamental cell behaviors such as adhesion, differentiation, death, proliferation, and migration. The cell assays can be performed under control conditions as well as for evaluation of cell responsiveness to cytoactive agents. Liquid crystal-based assay systems (LC assays) are described in WO 99/63329, which is herein incorporated by reference, and Gupta et al., Science 279:2077-2080 (1998). See also Seung-Ryeol Kim, Rahul R. Shah, and Nicholas L. Abbott; Orientations of Liquid Crystals on Mechanically Rubbed Films of Bovine Serum Albumin: A Possible Substrate for Biomolecular Assays Based on Liquid Crystals, Analytical Chemistry; 2000; 72(19); 4646-4653; Justin J. Skaife and Nicholas L. Abbott; Quantitative Interpretation of the Optical Textures of Liquid Crystals Caused by Specific Binding of Immunoglobulins to Surface-Bound Antigens, Langmuir; 2000; 16(7); 3529-3536; Vinay K. Gupta and Nicholas L. Abbott; Using Droplets of Nematic Liquid Crystal To Probe the Microscopic and Mesoscopic Structure of Organic Surfaces, Langmuir; 1999; 15(21); 7213-7223. R. R. Shah and N. L. Abbott, Principles for measurement of chemical exposure based on recognition-driven anchoring transitions in liquid crystals, Science; 2001; 293 (5533):1296-99. WO 01/61357 describes the detection of viruses using liquid crystal based assays. These assays utilize a patterned detection region on a substrate that organizes mesogens in a homeotropic orientation. The assays are designed so that binding of a virus to the detection regions disrupts the homeotropic orientation.

The LC assays of the present invention are useful for detecting the presence, spatial distribution, and states of cells, and also for detecting and quantitating a wide variety of molecules (e.g., chemical and biological materials, such as ions, proteins and polypeptides, lipids, polysaccharides, nucleic acids, low molecular weight compounds, and the like) that act as chemotactic or cellular adhesion and proliferation inducing agents or are secreted by cells in response to environmental stimuli. The LC assays may also be used to investigate regional differences on individual cell surfaces as to the expression of surface receptors or secretion of molecules such as growth factors, chemokines, cytokines, enzymes and constituents of the extracellular matrix. The LC assays of the present inventions are also useful for detecting and quantitating cells attached to a substrate (directly applicable to assays of cell adhesion, cell differentiation and cell proliferation) as well as assaying migration in a variety of cell types (e.g., cancer cells, lymphocytes, bacteria, archaea, etc.). This allows the quantitative analysis of the impact of a wide array of cytoactive compounds that may promote, have no effect or inhibit the fundamental cellular processes.

The assays can also be used to discern subtle changes in the motility of a cell (or particular type of cell) upon contact with a suspected cytoactive agent. Indeed, the assays can be used to detect and quantify a variety of biological and non-biological entities including, but not limited to, eukaryotic cells, prokaryotic cells, viruses bacteria, fungi, beads, and particles in suspension. LC assays of the present invention are used to directly detect interruption of their surfaces and, in preferred embodiments, the assayed materials do not require labels, fluorescent dyes, colored substrates, or secondary antibodies.

In some preferred embodiments, the present inventions finds use in the detection and/or analysis of cells, including, but not limited to include, Chinese hamster ovary cells (CHO-K1, ATCC CCl-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); human hepatoma line (Hep G2), and, for example, the following cancerous cells or cells isolated from the following carcinomas: fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrbm's macroglobulinemia, and heavy chain disease.

Furthermore, the LC assays of the present invention are readily adaptable to multi-array formats that permit simultaneous quantitation of the effects of one or more cytoactive agents upon one or more types of target cells and appropriate controls. Adaptability to multi-array formats also makes the LC assays of the present invention useful in high-throughput screening applications such as drug discovery. The LC assays of the present invention are also fast because the liquid crystals reorient in response to alterations in a surface in seconds.

In some embodiments of the present invention, the LC assays comprise a substrate to which recognition moieties are attached, preferably via an organic layer on the substrate (See, e.g., U.S. Pat. No. 6,284,197, which is incorporated herein by reference). In preferred embodiments, the substrate or organic layer serves to uniformly orient the liquid crystal. In some preferred embodiments, the substrate surface is prepared by rubbing, micro/nanoblasting (i.e., abrasion of a surface with submicron particles to create roughness), high pressure water etching or oblique deposition of a metal. In some embodiments the substrate consists of a protein coated surface. In some embodiments, the substrate provides a uniform, homogenous or planar surface, while in other embodiments, the surface is heterogeneous and/or contains topographic features. In some particularly preferred embodiments, the substrate is patterned to allow quantification.

Ordered nanostructured anisotropic surfaces introduce order into (e.g., align) liquid crystal films that are placed onto their surfaces. This ordering influence of the substrate can be eliminated by specific binding of target molecules to receptors immobilized upon the surface in which the dimensions of the topographic features of the substrate are matched to that of the target molecule. Another method contemplated herein for the detection and quantification of cells, microorganisms (e.g., bacteria, viruses, fungi, parasites) and particulate matter, is to simply block access to the ordering influence of the underlying nanostructured substrate by placement of cells, microorganisms, particulate matter or non-specifically or specifically secreted or deposited proteins or other matrices on its surface.

Accordingly, in some embodiments, assay substrates are provided that facilitate detection and quantification of cells, microorganisms and particulate matter in a nonspecific manner. These assay substrates preferably include at least one assay region that orients liquid crystals. In preferred embodiments, the assay region that orients liquid crystals comprises a surface. As described above, the surface may have intrinsic features (e.g., anisotropic structures) that orient liquid crystals, or the surface may have associated therewith particles or other materials that orient liquid crystals (i.e., extrinsic ordering materials). These extrinsic ordering materials may align liquid crystals directly or may be a aligned by application of an extrinsic force such as a magnetic field, electric field, or polarized light. As such, the present invention is not limited to any particular method of providing a surface or other structure that orients liquid crystals. For example, in some embodiments, nanorods are deposited on the surface and aligned using a motive force exemplified by but not limited to electric fields, magnetic fields, and fluid flow across surface.

In some preferred embodiments, the assays of the present invention may be used to quantify the amount of particulate matter is a sample, for example, the amount of viral particles in a sample. Currently, viruses are usually quantified by biological assays (e.g., LD50, TCID 50 or plaque titrations). Particle counts aren't often performed because they require electron microscopy. The assays of the present invention may be used to quantify viral particles in a sample by applying the viral particles to a substrate surface via diffusion of an electric field, and overlaying the substrate with a liquid crystal. The disorder of the liquid crystal is related to the number of particles on the ordered surface.

In some preferred embodiments, it is contemplated that when a particular cell type of interest is deposited upon, adheres to and/or migrates across the surface of the LC substrate, the topographic features in contact with the liquid crystal film is altered thus altering the alignment of the overlying LC film. In the case of a migrating cell, local order may be disrupted by its passage over an anisotropically ordered surface or may locally introduce order into a randomly ordered surface.

In preferred embodiments, the concentration of chemotactic agents and the number of cells contacted to a LC assay surface are controlled such that distinct cellular migration paths are observable. According to the present invention, the disruption of orientation can be detected by a variety of methods, including viewing with polarized light, measuring the threshold electrical field required to change the orientation of the liquid crystal, and viewing in the presence of dichroic agents.

In other preferred embodiments, one or more chemical agents and cell types are contacted (e.g., arrayed) over the surface of a disordered surface such that subsequent cellular adhesion and migration causes the uniform orientation of the previously disordered liquid crystal along the discrete path of motility. The ordered liquid crystals can be viewed using polarizing filters and/or using a specific wavelength or combination of wavelengths of light. In some embodiments, the change in order of the surface is localized and discreet in nature. In other embodiments, the change in the order of the surface is generalized.

Accordingly, the present invention provides improved substrates and devices for LC assays, including quantitative LC assays. For convenience, the description of the present invention is divided into the following sections: I. Substrates; II. Organic Layers; III. Recognition Moieties; IV. Mesogenic Layers; V. Patterned Liquid Crystals; VI. Analytical Devices; VII. Cell Assays and VIII. Zymography Assays.

I. Substrates

Substrates that are useful in practicing the present invention can be made of practically any physicochemically stable material. In a preferred embodiment, the substrate material is non-reactive towards the constituents of the mesogenic layer. The substrates can be either rigid or flexible and can be either optically transparent or optically opaque. The substrates can be electrical insulators, conductors or semiconductors. Further, the substrates can be substantially impermeable to liquids, vapors and/or gases or, alternatively, the substrates can be permeable to one or more of these classes of materials. Exemplary substrate materials include, but are not limited to, inorganic crystals, inorganic glasses, inorganic oxides, metals, organic polymers and combinations thereof.

A. Inorganic Crystal and Glasses

In some embodiments of the present invention, inorganic crystals and inorganic glasses are utilized as substrate materials (e.g., LiF, NaF, NaCl, KBr, KI, $CaF_2$, $MgF_2$, $HgF_2$, BN, $AsS_3$, ZnS, $Si_3N_4$ and the like). The crystals and glasses can be prepared by art standard techniques (See, e.g., Goodman, C. H. L., Crystal Growth Theory and Techniques, Plenum Press, New York 1974). Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

B. Inorganic Oxides

In other embodiments of the present invention, inorganic oxides are utilized as the substrate. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In a presently preferred embodiment, the substrate is a rigid structure that is impermeable to liquids and gases. In this embodiment, the substrate consists of a glass plate onto which a metal, such as gold is layered by evaporative deposition. In a still further preferred embodiment, the substrate is a glass plate ($SiO_2$) onto which a first metal layer such as titanium has been layered. A layer of a second metal such as gold is then layered on top of the first metal layer.

C. Metals

In still further embodiments of the present invention, metals are utilized as substrates. The metal can be used as a crystal, a sheet or a powder. The metal can be deposited onto a backing by any method known to those of skill in the art including, but not limited to, evaporative deposition, sputtering, electroless deposition, electrolytic deposition and adsorption or deposition of preformed particles of the metal including metallic nanoparticles.

Any metal that is chemically inert towards the mesogenic layer will be useful as a substrate in the present invention. Metals that are reactive or interactive towards the mesogenic layer will also be useful in the present invention. Metals that are presently preferred as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another. In a preferred embodiment, the metal used for the substrate is gold. In a particularly preferred embodiment the metal used is gold layered on titanium.

The metal layers can be either permeable or impermeable to materials such as liquids, solutions, vapors and gases.

D. Organic Polymers

In still other embodiments of the present invention, organic polymers are utilized as substrate materials. Organic polymers useful as substrates in the present invention include polymers that are permeable to gases, liquids and molecules in solution. Other useful polymers are those that are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins (See, Cognard, J. ALIGNMENT OF NEMATIC LIQUID CRYSTALS AND THEIR MIXTURES, in Mol. Cryst. Liq. Cryst. 1:1-74 (1982)). Presently preferred organic polymers include polydimethylsiloxane, polyethylene, polyacrylonitrile, cellulosic materials, polycarbonates and polyvinyl pyridinium.

In a presently preferred embodiment, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds that are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In a further preferred embodiment, the layer of gold on the permeable membrane is itself permeable. In a still further preferred embodiment, the permeable gold layer has a thickness of about 70 Angstroms or less.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in a preferred embodiment, the film is of a thickness of from about 0.01 nanometer to about 1 micrometer. In a further preferred embodiment, the film is of a thickness of from about 5 nanometers to about 100 nanometers. In yet a further preferred embodiment, the film is of a thickness of from about 10 nanometers to about 50 nanometers.

E. Substrate Surfaces

It is contemplated that the nature of the surface of the substrate has a profound effect on the anchoring of the mesogenic layer that is associated with the surface. The surface can be engineered by the use of mechanical and/or chemical techniques. The surface of each of the above enumerated substrates can be substantially smooth (planar). Alternatively, the surface can be roughened or patterned by rubbing, etching, grooving, stretching, stressing, impacting, nanoblasting, oblique deposition or other similar techniques known to those with skill in the art. Additionally, an ordered surface can be created by the deposition (decoration) of nano-micro sized particles that are deposited onto a planar surface. These particles may be placed onto the surface in an ordered array using a nanostamper or "negative" nanostamper (see FIGS. 1A and 1B) or may be placed on in a random array and subsequently ordered using motive forces exemplified by but not limited to electric fields, magnetic fields and fluid flow. Of particular relevance is the texture of the surface that is in contact with the mesogenic compounds.

Thus, in one preferred embodiment, the substrate is glass or an organic polymer and the surface has been prepared by rubbing. Rubbing can be accomplished using virtually any material including tissues, paper, fabrics, brushes, polishing paste, etc. In a preferred embodiment, the rubbing is accomplished by use of a diamond rubbing paste. In another preferred embodiment, the face of the substrate that contacts the mesogenic compounds is a metal layer that has been obliquely deposited by evaporation. In a further preferred embodiment, the metal layer is a gold layer.

In other embodiments of the present invention, anisotropic surfaces are prepared by nanoblasting a substrate with nanometer scale beads (e.g., 1-200 nm, preferably 50-100 nm) at a defined angle of incidence (e.g., from about 5-85 degrees, preferably about 45 degrees). The nanoblasted surface can be utilized as is or can be further modified, such as by obliquely depositing gold on the surface.

In still further embodiments, the ansiotropic surfaces of the devices of the present invention are prepared by stretching an appropriate substrate. For example, polymers substrates such as polystyrene can be stretched by heating to a temperature above the glass transition temperature of the substrate, applying a tensile force, and cooling to a temperature below the glass transition temperature before removing the force.

In some embodiments, the present invention provides substrates with heterogenous features for use in the various devices and methods. In some embodiments, the heterogenity is a uniform or non-uniform gradient in topography across the surface. For example, gold can be deposited onto a substrate at varying angles of incidence. Regions containing gold deposited at a near-normal angle of incidence will cause non-uniform anchoring of the liquid crystal, while areas in which the angle of incidence was greater than 10 degrees will uniformly orient crystals. Alternatively, the heterogeneity may be the presence of two or more distinct scales of topography distributed uniformly across the substrate. It is contemplated that such substrates are useful for increasing the dynamic range of detection of analytes or for detecting the presence of analytes of a different size within a sample.

The substrate can also be patterned using techniques such as photolithography (Kleinfield et al., *J. Neurosci.* 8:4098-120 (1998)), photoetching, chemical etching, microcontact printing (Kumar et al., *Langmuir* 10:1498-511 (1994)), and chemical spotting.

The size and complexity of the pattern on the substrate is limited only by the resolution of the technique utilized and the purpose for which the pattern is intended. For example, using microcontact printing, features as small as 200 nm have been layered onto a substrate (See, Xia, Y.; Whitesides, G., *J. Am. Chem. Soc.* 117:3274-75 (1995)). Similarly, using photolithography, patterns with features as small as 1 μm have been produced (See, Hickman et al., *J. Vac. Sci. Technol.* 12:607-16 (1994)). Patterns which are useful in the present invention include those which comprise features such as wells, enclosures, partitions, recesses, inlets, outlets, channels, troughs, diffraction gratings and the like.

In a presently preferred embodiment, the patterning is used to produce a substrate having a plurality of adjacent wells, wherein each of the wells is isolated from the other wells by a raised wall or partition and the wells do not fluidically communicate. Thus, an analyte (e.g., a potential chemotactic agent), or other substance, placed in a particular well remains substantially confined to that well. In another preferred embodiment, the patterning allows the creation of channels through the device whereby an agent can enter and/or exit the device.

The pattern can be printed directly onto the substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art (See, e.g., Kleinfield et al., *J. Neurosci.* 8:4098-120 (1998)). Following removal of the photoresist, a second organic layer, having a structure different from the first organic layer, can be bonded to the substrate on those areas initially covered by the resist. Using this technique, substrates with patterns having regions of different chemical characteristics can be produced. Thus, for example, a pattern having an array of adjacent wells can be created by varying the hydrophobicity/hydrophilicity, charge and other chemical characteristics of the pattern constituents. In one embodiment, hydrophilic compounds can be confined to individual wells by patterning walls using hydrophobic materials. Similarly, positively or negatively charged compounds can be confined to wells having walls made of compounds with charges similar to those of the confined compounds. Similar substrate configurations are accessible through microprinting a layer with the desired characteristics directly onto the substrate (See, Mrkish, M.; Whitesides, G. M., *Ann. Rev. Biophys. Biomol. Struct.* 25:55-78 (1996)).

In yet another preferred embodiment, the patterned substrate controls the anchoring alignment of the liquid crystal. In a particularly preferred embodiment, the substrate is patterned with an organic compound that forms a self-assembled monolayer. In this embodiment, the organic layer controls the azimuthal orientation and/or polar orientation of a supported mesogenic layer.

In still further preferred embodiments, the present invention provides surfaces that have particles (preferably nano- to micro-sized particles distributed thereon). It is contemplated that such particles find use both in orienting liquid crystals and in masking underlying orienting features associated with the surface, depending on the configuration. In some embodiments, a stamping device is utilized that deposits micro- to nano-sized particles on a surface (See, e.g., FIG. 1A). It is possible to make a stamp from relatively friable materials that are transferred to the substrate upon mechanical contact with the substrate. Examples of such transferable materials include but are not limited to charcoal, chalk, soapstone, graphite, pumice and other easily fragmented and transferred materials. This can include a synthetic laminated material, prepared such that fracturing layers are designed into the material.

It is also possible to create an aligned surface using mechanical transfer of organized or aligned particles ("positive transfer stamp"). Such a device would have a design similar to FIG. 1A but instead of the arrayed ridges being composed of a friable material, they are composed of a non-consumable material appropriate for picking up particles and depositing them on a test surface in an ordered array. For example, a hydrophobic stamp containing topography may be fabricated. The particles, when deposited onto the topography are either organized or aligned such that when transferred to a substrate on which the cells are grown, the liquid crystal is aligned. These particles can be hidden, displaced or reoriented when cells are deposited onto, attach to, grow or migrate on the surface. In some preferred embodiments of a transfer stamp, electric or magnetic fields are applied across the stamp to collect particles. In further preferred embodiments, the applied field is changed so as to affect the transfer of particles to the test substrate in an ordered array. The ordered array of particles would subsequently align mesogens in a LC film placed on the test substrate's surface. In some embodiments of the invention, the positions of the particles once transferred to the substrates are made tolerant to handling and unintended disruption of ordering by chemical or physical attachment to the substrate.

Figure 2A:
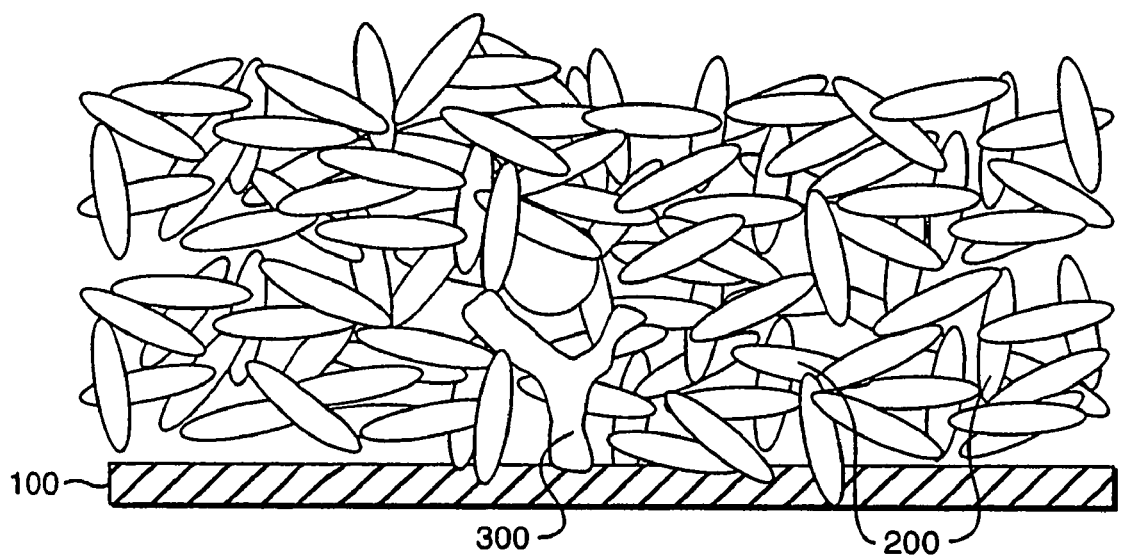
FIG. 2A is a schematic depiction of random ordering of mesogens.

FIG. 2A depicts the use of a negative nanostamping device. In this embodiment, nano to micro-sized particulate matter is randomly distributed across the test surface of a substrate and anisotropic order created by using a "negative stamping" method that removes material in an ordered fashion leaving an anisotropically patterned surface that aligns the mesogens in an LC film.

In some embodiments, the substrate surface further comprises a plurality of magnetic particles (e.g., metallic nanorods) evenly distributed across the substrate surface. In certain of these embodiments, the magnetic particles are salted onto the surface of the substrate. The present invention contemplates that the orientation of magnetic nanoparticles can be manipulated (e.g., ordered) by controlled application of a magnetic field or electrical current.

In some embodiments, the cells, microorganisms, or particles on a planar surface are visualized by introducing order into the liquid crystal film by methods exemplified by, but not limited to, the use of electric fields, magnetic fields and/or the placement of nano- and/or microparticles deposited on the surface that are ordered on initial deposition (using a nano or microstamper device) or ordered subsequent to deposition by use of electric fields, magnetic fields or the use of fluid flow. In the case of ordering the LC film with electric or magnetic fields or by fluid flow without the use of an intrinsic anisotropic nanostructured substrate or the use of anisotropically ordered nano and/or microparticles decorating the surface, the order introduced in the LC film by these methods is disrupted locally by the presence of cells, microorganisms and/or particulate matter as well as specifically immobilized target molecules. The degree of disruption is quantifiable by the magnitude of the ordering motive force (e.g. electric field) required to maintain a uniformly ordered LC film despite the presence of a disruptive element represented by the presence of material (e.g., cells, microorganisms, particulate matter) on the surface.

Figure 2B:
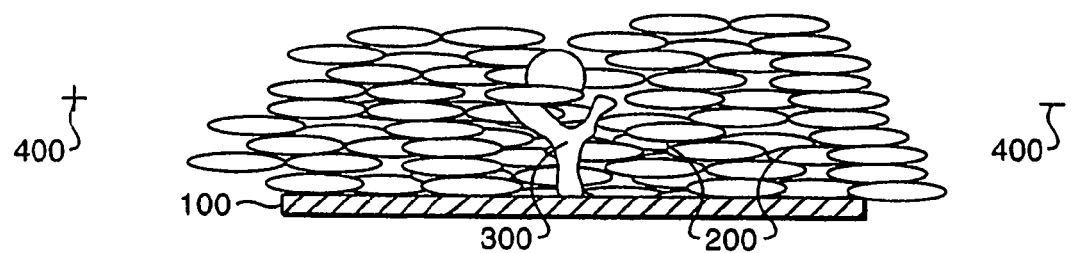
FIG. 2B is a schematic depiction of ordering of mesogens induced by an electric field.
Figure 3:
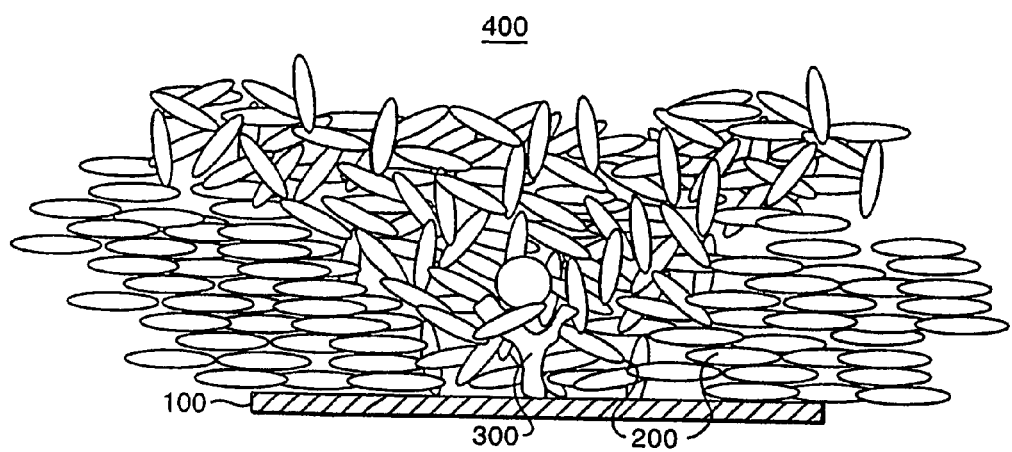
FIG. 3 is a schematic depiction of the effect of reducing or discontinuing a motive force such as an electric field.

Additionally, it is contemplated that upon cessation of application of said motive force the cells, microorganisms, and/or particulate matter present on the surface introduce disorder into the LC layer proportional to their size and density. In some embodiments, the analytes (e.g., particulate matter, cells, or microorganisms) are passively placed onto the surface and nonspecifically associated with the surface; while in other embodiments, the analytes are specifically immobilized onto (e.g., target molecules immobilized by specific binding to receptors) the planar surface. This principle is illustrated in FIGS. 2A, 2B, and 3. In FIG. 2A it can be seen that the mesogens are randomly arranged around the binding sequence immobilized on the planar surface (100) with its target analyte (300). The element to be detected on the planar surface could also be a particle, a cell or a microorganism (bacteria, fungi, virus, parasite). These elements to be detected may be specifically bound to the surface as depicted or could simply be resting on the surface or non-specifically (i.e. no specific binding sequence present) associated to the surface. On a planar surface with or without elements to be detected the mesogens have a random distribution (200).

Referring to FIG. 2B, an electric field (400) is used as an example of the motive force that could be used to align the mesogens in the liquid crystal, though other motive forces that align liquid crystal mesogens (exemplified by, but not limited to magnetic fields and fluid flow) could also be used. It can be appreciated that the motive force is sufficient to overcome the introduction of disorder into the mesogenic layer by the presence of elements on the planar surface. While the force is applied, all mesogenic elements are aligned (200). Referring to FIG. 3, the effect of greatly reducing or discontinuing application of an aligning motive force is illustrated. The mesogenic elements away from the target analyte, cell, microorganism or particle on the surface stay aligned. The mesogenic elements in association with the target analyte, cell, microorganism or particle have disorder introduced into them. This disorder is communicated many molecular lengths away and allows detection using polarized light or specific wavelengths or combinations of wavelengths of light. It will be appreciated that the orientation of the liquid crystal on the substrate, in the absence of the applied field and bound analyte, has a degenerate degree of orientational freedom. This means that the liquid crystal can be irreversibly changed by the application of the field. An example of such an interface is a liquid-liquid interface (e.g., degenerate azimuthal orientations), but the invention is not confined to operation at this interface. Examples of degenerate anchoring of liquid crystals on solid surfaces are well known to those skilled in the art (see Physics of Liquid Crystals, Prost and de Gennes).

Figure 4:
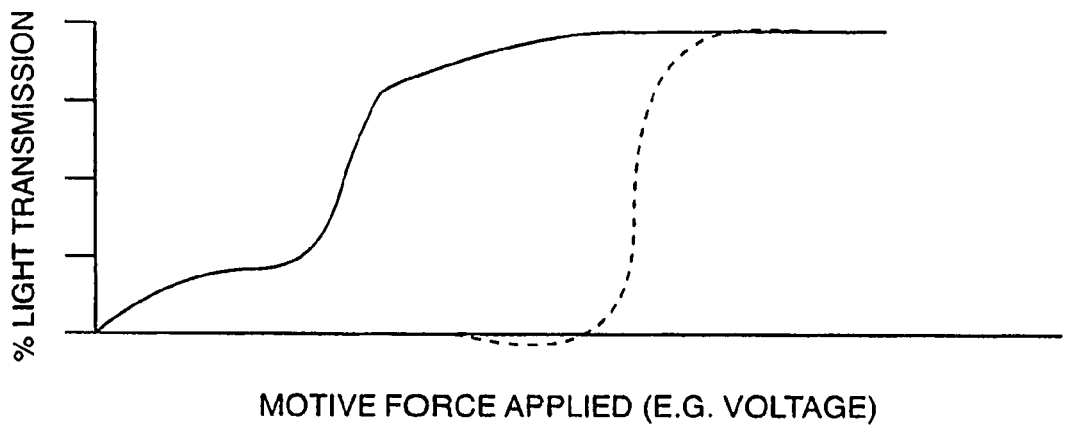
FIG. 4 is a graphical depiction of the relationship between light transmission and motive force.

Additionally, in other embodiments, the present invention contemplates methods in which a planar surface is seeded with cells, microorganisms or particulate matter. A liquid crystal film is placed onto the surface and alignment is introduced using a motive force (e.g., electric fields, magnetic fields or fluid flow). The present invention is not limited to any particular mechanism of action. Indeed, an understanding of the mechanism of action is not necessary to practice the present invention. Nevertheless, the magnitude of the force required to maintain alignment of the liquid crystal is proportional to the degree of disruptive force possessed by an element on the surface. A major contributor to the disruptive force (i.e., the ability to introduce disorder into the mesogenic layer) is related to its size. Collecting information (e.g., a curve) of the change in light transmission as a function of motive force applied necessary to maintain a uniformly aligned LC film provides quantitative data on the relative amount of different sized particles. FIG. 4 demonstrates that the force/light transmission curves differ significantly between two populations of elements placed on a planar surface.

In FIG. 4, the solid line depicts the force curve associated with a population of analytes having heterogeneously sized particles with a few predominant sizes and the dashed line is consistent with the presence of a homogenous population of relatively large particles. The positions of these curves also depend on the number of particles on the surface. For a given applied force (e.g., electric field), the transmission of light is greater if more particles are present on the surface. That is, the particles prevent the uniform alignment promoted by the applied field.

Additionally, rather than using a nanostructured or microstructured substrate, it is possible to use an electric field or magnetic field to order the LC or enhance the optical contrast between regions of the substrate occupied or not occupied by cells or other particulate matter, microorganisms (bacteria, fungi, viruses, parasites) as well as specific or non-specific analytes. These embodiments are described in more detail below.

F. Liquid Crystal Substrates and Matrices

Additionally, in some embodiments, liquid crystalline substrates are employed to report biomechanical forces imparted to the substrate by the adhesion, movement and contraction of cells. In some embodiments, the LC substrate is functionalized by the adhesion of matrix proteins, glass or other biocompatible polymeric substrates to support cell function. In other embodiments, the LC substrate comprises a low molecular weight LC film spread over a solid substrate, a LC gel that is formed by particles or gelator molecules dispersed in the liquid crystal, a polymeric liquid crystal, a polymer-stabilized liquid crystalline film that is prepared by the polymerization of a network of polymer in a liquid crystal (similar to that used in polymer-dispersed liquid crystal displays), or polymer stabilized liquid crystals (e.g., lyotropic liquid crystals). The surfaces of the liquid crystal films can be functionalized by immobilization of receptors that are anchored to the surface by one of the various methods of immobilization known to those skilled in the art, including but not limited to covalent attachment, physisorption for example by using a receptor coupled to a surface-active molecule, or by use of polymers adsorbed to the surface of the liquid crystalline substrate.

In some preferred embodiments, a hybrid liquid crystalline film is prepared from a combination of a liquid crystal and extracellular matrix (ECM) constituents or a combination of liquid crystals and cell adhesion molecules (e.g. ICAM, selecting, syndeeans). In another preferred embodiment of the invention, the extracellular matrix constituents or synthetic mimics of ECM exhibits liquid crystalline order that is altered by the present of cells attached to the matrix. The degree of disorder or order of the liquid crystal film can be assessed and quantified using white light or using a specific wavelength or combination of wavelengths of light.

In yet other embodiments, the use of a liquid crystalline matrix is employed that reports the transduction of biomechanical forces from cells placed on the surface into the matrix that alters the passage of light. Additionally, in some embodiments, thin films of extracellular matrices (e.g., collagen or fibronectin), cell surface adhesion molecules, thin polymeric films that support cell function and may have been functionalized by the immobilization of extracellular matrix constituents or specific binding sequences (e.g., RGD) that promote cell function, and hybrid extracellular-liquid crystalline matrices are used to report biomechanical forces imparted into these films by cellular processes such as adhesion, migration or contraction.

In still further embodiments, matrices (e.g., ECMs) are provided that have been modified to orient liquid crystals. Such matrices also find use in adhesion, migration, and invasion assays.

II. Organic Layers

In addition to the ability of a substrate to anchor a mesogenic layer, an organic layer attached to the substrate is similarly able to provide such anchoring. A wide range of organic layers can be used in conjunction with the present invention. These include, but are not limited to, organic layers formed from organosulfur compounds (including thiols and disulfides), organosilanes, amphiphilic molecules, cyclodextrins, polyols (e.g., poly(ethyleneglycol), poly(propyleneglycol), fullerenes, and biomolecules (e.g., proteins, lipids, nucleic acids, polysaccharides, phospholipids and the like). In preferred embodiments that employ organic layers, the layer is selected after considering the affects the layer will have on the assay. For example, assays where the migration of cells are being considered, one skilled in the art would select an organic layer that is not expected to interfere with reactions' conditions and cellular migration, alternatively, one skilled in the art could select an organic layer expected to either promote or retard cellular migration.

A. Anchoring

An organic layer that is bound to, supported on or adsorbed onto, the surface of the substrate can anchor a mesogenic layer. As used herein, the term "anchoring" refers to the set of orientations adopted by the molecules in the mesogenic phase. The mesogenic layer will adopt particular orientations while minimizing the free energy of the interface between the organic layer and the mesogenic layer. The orientation of the mesogenic layer is referred to as an "anchoring direction." A number of anchoring directions are possible.

It is contemplated that the particular anchoring direction adopted will depend upon the nature of the mesogenic layer, the organic layer and the substrate. Anchoring directions of use in the present invention include, for example, conical anchoring, degenerate anchoring, homeotropic anchoring, multistable anchoring, planar anchoring and tilted anchoring. Planar anchoring and homeotropic anchoring are preferred with planar anchoring being most preferred.

The anchoring of mesogenic compounds by surfaces has been extensively studied for a large number of systems (See, for example, Jerome, *Rep. Prog. Phys.* 54:391-451 (1991)). The anchoring of a mesogenic substance by a surface is specified, in general, by the orientation of the director of the bulk phase of the mesogenic layer. The orientation of the director, relative to the surface, is described by a polar angle (measured from the normal of the surface) and an azimuthal angle (measured in the plane of the surface).

Control of the anchoring of mesogens has been largely based on the use of organic surfaces prepared by coating surface-active molecules or polymer films on inorganic (e.g., silicon oxide) substrates followed by surface treatments such as rubbing. Other systems which have been found useful include surfaces prepared through the reactions of organosilanes with various substrates (See, for example, Yang et al., In MICROCHEMISTRY: SPECTROSCOPY AND CHEMISTRY IN SMALL DOMAINS; Masuhara et al., Eds.; North-Holland, Amsterdam, 1994; p. 441).

Molecularly designed surfaces formed by organic layers on a substrate can be used to control both the azimuthal and polar orientations of a supported mesogenic layer. Self-assembled monolayers (SAMs) can be patterned on a surface. For example, patterned organic layers made from $CH_3(CH_2)_{14}SH$ and $CH_3(CH_2)_{15}SH$ on obliquely deposited gold produce a supported mesogenic layer which is twisted 90°. Other anchoring modes are readily accessible by varying the chain length and the number of species of the organic layer constituents (See, Gupta and Abbott, *Science* 276:1533-1536 (1997)).

Transitions between anchoring modes have been obtained on a series of organic layers by varying the structure of the organic layer. Structural features that have been found to affect the anchoring of mesogenic compounds include, for example, the density of molecules within the organic layer, the size and shape of the molecules constituting the organic layer and the number of individual layers making up the bulk organic layer.

The density of the organic layer on the substrate has been shown to have an effect on the mode of mesogen anchoring. For example, transitions between homeotropic and degenerate anchorings have been obtained on surfactant monolayers by varying the density of the monolayers (See, Proust et al., *Solid State Commun.* 11:1227-30 (1972)). Thus, it is within the scope of the present invention to tailor the anchoring mode of a mesogen by controlling the density of the organic layer on the substrate.

The molecular structure, size and shape of the individual molecules making up the organic layer also effects the anchoring mode. For example, it has been demonstrated that varying the length of the aliphatic chains of surfactants on a substrate can also induce anchoring transitions; with long chains, a homeotropic anchoring is obtained while with short chains, a conical anchoring is obtained with the tilt angle θ increasing as the chain becomes shorter (See, e.g., Porte, J. *Physique* 37:1245-52 (1976)). Additionally, recent reports have demonstrated that the polar angle of the mesogenic phase can be controlled by the choice of the constituents of the organic layer. See, Gupta and Abbott, *Langmuir* 12:2587-2593 (1996). Thus, it is within the scope of the present invention to engineer the magnitude of the anchoring shift as well as the type of shift by the judicious choice of organic layer constituents.

Biomolecules can also be used as organic layers. (see Seung-Ryeol Kim, Rahul R. Shah, and Nicholas L. Abbott; Orientations of Liquid Crystals on Mechanically Rubbed Films of Bovine Serum Albumin: A Possible Substrate for Biomolecular Assays Based on Liquid Crystals, Analytical Chemistry; 2000; 72(19); 4646-4653). A preferred embodiment when using biomolecules as organic layers is based on the mechanical rubbing of the organic layer with a fabric cloth following chemical immobilization of the organic layer on the surface of a substrate.

A wide variety of organic layers are useful in practicing the present invention. These organic layers can comprise monolayers, bilayers and multilayers. Furthermore, the organic layers can be attached by covalent bonds, ionic bonds, physisorption, chemisorption and the like, including, but not limited to, hydrophobic interactions, hydrophilic interactions, van der Waals interactions and the like.

In a presently preferred embodiment, organic layers which form self-assembled monolayers are used. The use of self-assembled monolayers (SAMs) formed from alkanethiols on thin, semitransparent films of gold in studies on the anchoring of liquid crystals on surfaces has been reported (See, Drawhom and Abbott, *J. Phys. Chem.* 45:16511 (1995)). The principal result of that work was the demonstration that SAMs formed from n-alkanethiols with long ($CH_3(CH_2)_{15}SH$) and short ($CH_3(CH_2)_4SH$ or $CH_3(CH_2)_9SH$) aliphatic chains can homeotropically anchor mesogens. In contrast, single-component SAMs caused non-uniform, planar, or tilted anchoring at room temperature.

In the discussion that follows, self-assembled monolayers are utilized as an exemplary organic layer. This use is not intended to be limiting. It will be understood that the various configurations of the self-assembled monolayers and their methods of synthesis, binding properties and other characteristics are equally applicable to each of the organic layers of use in the present invention.

B. Self-Assembled Monolayers

Self-assembled monolayers are generally depicted as an assembly of organized, closely packed linear molecules. There are two widely-used methods to deposit molecular monolayers on solid substrates: Langmuir-Blodgett transfer and self-assembly. Additional methods include techniques such as depositing a vapor of the monolayer precursor onto a substrate surface and the layer-by-layer deposition of polymers and polyelectrolytes from solution (Guy Ladam, Pierre Schaaf, Frédéric J. G. Cuisinier, Gero Decher, and Jean-Claude Voegel; Protein Adsorption onto Auto-Assembled Polyelectrolyte Films, Langmuir; 2001; 17(3); 878-882).

The composition of a layer of a SAM useful in the present invention can be varied over a wide range of compound structures and molar ratios. In one embodiment, the SAM is formed from only one compound. In a presently preferred embodiment, the SAM is formed from two or more components. In another preferred embodiment, when two or more components are used, one component is a long-chain hydrocarbon having a chain length of between 10 and 25 carbons and a second component is a short-chain hydrocarbon having a chain length of between 1 and 9 carbon atoms. In particularly preferred embodiments, the SAM is formed from $CH_3(CH_2)_{15}SH$ and $CH_3(CH_2)_4SH$ or $CH_3(CH_2)_{15}SH$ and $CH_3(CH_2)_9SH$. In any of the above described embodiments, the carbon chains can be functionalized at the ω-terminus (e.g., $NH_2$, COOH, OH, CN), at internal positions of the chain (e.g., aza, oxa, thia) or at both the ω-terminus and internal positions of the chain.

The mesogenic layer can be layered on top of one SAM layer or it can be sandwiched between two SAM layers. In those embodiments in which the mesogenic layer is sandwiched between two SAMs, a second substrate, optionally substantially identical in composition to that bearing the SAM can be layered on top of the mesogenic layer. Alternatively a compositionally different substrate can be layered on top of the mesogenic layer. In a preferred embodiment, the second substrate is permeable. In yet another preferred embodiment two substrates are used, but only one of the substrates has an attached organic layer.

When the mesogenic layer is sandwiched between two layers of SAMs several compositional permutations of the layers of SAMs are available. For example, in one embodiment, the first organic layer and the second organic layer have substantially identical compositions and both of the organic layers bear an attached recognition moiety. A variation on this embodiment utilizes first and second organic layers with substantially similar compositions, wherein only one of the layers bears a recognition moiety.

In another embodiment, the first and second organic layers have substantially different compositions and only one of the organic layers has an attached recognition moiety. In a further embodiment, the first organic layer and said second organic layer have substantially different compositions and both of the organic layers have an attached recognition moiety.

In a presently preferred embodiment, the organic layers have substantially identical compositions and one or both of the organic layers has attached thereto a recognition moiety.

A recognition moiety can be attached to the surface of a SAM by any of a large number of art-known attachment methods. In one preferred embodiment, a reactive SAM component is attached to the substrate and the recognition moiety is subsequently bound to the SAM component via the reactive group on the component and a group of complementary reactivity on the recognition moiety (See, e.g., Hegner et al. *Biophys. J.* 70:2052-2066 (1996)). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a recognition moiety.

C. Functionalized SAMs

The discussion that follows focuses on the attachment of a reactive SAM component to the substrate surface. This focus is for convenience only and one of skill in the art will understand that the discussion is equally applicable to embodiments in which the SAM component-recognition moiety is preformed prior to its attachment to the substrate. As used herein, "reactive SAM components" refers to components that have a functional group available for reaction with a recognition moiety or other species following the attachment of the component to the substrate.

Currently favored classes of reactions available with reactive SAM components are those that proceed under relatively mild conditions. These include, but are not limited to nucleophilic substitutions (e.g., reactions of amines and alcohols with acyl halides), electrophilic substitutions (e.g., enamine reactions) and additions to carbon-carbon and carbon-heteroatom multiple bonds (e.g., Michael reaction, Diels-Alder addition). These and other useful reactions are discussed in March, ADVANCED ORGANIC CHEMISTRY, Third Ed., John Wiley & Sons, New York, 1985.

According to the present invention, a substrate's surface is functionalized with SAM, components and other species by covalently binding a reactive SAM component to the substrate surface in such a way as to derivatize the substrate surface with a plurality of available reactive functional groups. Reactive groups which can be used in practicing the present invention include, for example, amines, hydroxyl groups, carboxylic acids, carboxylic acid derivatives, alkenes, sulfhydryls, siloxanes, etc.

A wide variety of reaction types are available for the functionalization of a substrate surface. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced polytetrafluoroethylene.

When the substrates are constructed of a siliaceous material such as glass, the surface can be derivatized by reacting the surface Si—OH, SiO—H, and/or Si—Si groups with a functionalizing reagent. When the substrate is made of a metal film, the surface can be derivatized with a material displaying avidity for that metal.

In a preferred embodiment, wherein the substrates are made from glass, the covalent bonding of the reactive group to the glass surface is achieved by conversion of groups on the substrate's surface by a silicon modifying reagent such as:

   (1)

where R is an alkyl group, such as methyl or ethyl, $R^1$ is a linking group between silicon and X and X is a reactive group or a protected reactive group. The reactive group can also be a recognition moiety as discussed below. Silane derivatives having halogens or other leaving groups beside the displayed alkoxy groups are also useful in the present invention.

A number of siloxane functionalizing reagents can be used, for example:
1. Hydroxyalkyl siloxanes (Silylate surface, functionalize with diborane, and $H_2O_2$ to oxidize the alcohol)
   a. allyl trichlorosilane→→3-hydroxypropyl
   b. 7-oct-1-enyl trichlorosilane→→8-hydroxyoctyl
2. Diol(dihydroxyalkyl)siloxanes (silylate surface and hydrolyze to diol)
   a. (glycidyl triethoxysilane→→(2,3-dihydroxypropyloxy)propyl
3. Aminoalkyl siloxanes (amines requiring no intermediate functionalizing step).
   a. 3-aminopropyl trimethoxysilane→aminopropyl
4. Dimeric secondary aminoalkyl siloxanes
   a. bis(3-trimethoxysilylpropyl)amine→bis(silyloxylpropyl)amine.

It will be apparent to those of skill in the art that an array of similarly useful functionalizing chemistries are available when SAM components other than siloxanes are used. Thus, for example, similarly functionalized alkyl thiols can be attached to metal films and subsequently reacted to produce the functional groups such as those exemplified above.

In another preferred embodiment, the substrate is at least partially a metal film, such as a gold film, and the reactive group is tethered to the metal surface by an agent displaying avidity for that surface. In a presently preferred embodiment, the substrate is at least partially a gold film and the group which reacts with the metal surface comprises a thiol, sulfide or disulfide such as:

   (2)

$R^2$ is a linking group between sulfur and $X^2$ and $X^2$ is a reactive group or a protected reactive group. $X^2$ can also be a recognition moiety as discussed below. Y is a member selected from the group consisting of H, $R^3$ and $R^3$—S—, wherein $R^2$ and $R^3$ are independently selected. When $R^2$ and $R^3$ are the same, symmetrical sulfides and disulfides result, and when they are different, asymmetrical sulfides and disulfides result.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding haloamines, halo-carboxylic acids, etc. by reaction of these halo precursors with sodium sulfhydride. See, e.g., Reid, ORGANIC CHEMISTRY of BIVALENT SULFUR, VOL 1, pp. 21-29, 32-35, vol. 5, pp. 27-34, Chemical Publishing Co., New York, 1.958, 1963. Additionally, functionalized sulfides can be prepared via alkylthio-de-halogenation with a mercaptan salt (See, Reid, ORGANIC CHEMISTRY OF BIVALENT SULFUR, vol. 2, pp. 16-21, 24-29, vol. 3, pp. 11-14, Chemical Publishing Co., New York, 1960). Other methods for producing compounds useful in practicing the present invention will be apparent to those of skill in the art.

In another preferred embodiment, the functionalizing reagent provides for more than one reactive group per each reagent molecule. Using reagents such as Compound 3, below, each reactive site on the substrate surface is, in essence, "amplified" to two or more functional groups:

   (3)

where R is an alkyl group, such as methyl, $R^2$ is a linking group between silicon and $X^2$, $X^2$ is a reactive group or a protected reactive group and n is an integer between 2 and 50, and more preferably between 2 and 20.

Similar amplifying molecules are also of use in those embodiments wherein the substrate is at least partially a metal film. In these embodiments the group which reacts with the metal surface comprises a thiol, sulfide or disulfide such as in Formula (4):

   (4)

As discussed above, $R^2$ is a linking group between sulfur and $X^2$ and $X^2$ is a reactive group or a protected reactive group. $X^2$ can also be a recognition moiety. Y is a member selected from the group consisting of H, $R^3$ and $R^3$—S—, wherein $R^2$ and $R^3$ are independently selected.

R groups of use for $R^1$, $R^2$ and $R^3$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups.

In each of Formulae 1-4, above, each of $R^1$, $R^2$ and $R^3$ are either stable or they can be cleaved by chemical or photochemical reactions. For example, R groups comprising ester or disulfide bonds can be cleaved by hydrolysis and reduction, respectively. Also within the scope of the present invention is the use of R groups that are cleaved by light such as, for example, nitrobenzyl derivatives, phenacyl groups, benzoin esters, etc. Other such cleaveable groups are well-known to those of skill in the art.

In another preferred embodiment, the organosulfur compound is partially or entirely halogenated. An example of compounds useful in this embodiment include:

   (5)

wherein, $X^1$ is a member selected from the group consisting of H, halogen reactive groups and protected reactive groups. Reactive groups can also be recognition moieties as discussed below. Q, $Q^1$ and $Q^2$ are independently members selected from the group consisting of H and halogen. $Z^1$ is a member selected from the group consisting of $-CQ_2-$, $-CQ^1_2-$, $-CQ^2_2-$, $-O-$, $-S-$, $NR^4-$, $-C(O) NR^4$ and $R^4NC$ (O0-, in which $R^4$ is a member selected from the group consisting of H, alkyl, substituted alkyl, aryl, substituted aryl, heteroaryl and heterocyclic groups and m and n are independently a number between 0 and 40.

In yet another preferred embodiment, the organic layer comprises a compound according to Formula 5 above, in which Q, $Q^1$ and $Q^2$ are independently members selected from the group consisting of H and fluorine. In a still further preferred embodiment, the organic layer comprises compounds having a structure according to Formulae (6) and (7):

$$CF_3(CF_2)_mZ^1(CH_2)_nSH \qquad (6)$$

$$CF_3(CF_2)_oZ^2(CH_2)_pSH \qquad (7)$$

wherein, $Z^1$ and $Z^2$ are members independently selected from the group consisting of $-CH_2-$, $-O-$, $-S-$, $NR^4$, $-C(O)NR^4$ and $R^4NC(O)-$ in which $R^4$ is a member selected from the group consisting of H, alkyl, substituted alkyl, aryl, substituted aryl, heteroaryl and heterocyclic groups. In a presently preferred embodiment, the Z groups of adjacent molecules participate in either an attractive (e.g., hydrogen bonding) or repulsive (e.g., van der Waals) interaction.

In Formulae 6 and 7, m is a number between 0 and 40, n is a number between 0 and 40, o is a number between 0 and 40 and p is a number between 0 and 40.

In a further preferred embodiment, the compounds of Formulae 6 and 7 are used in conjunction with an organosulfur compound, either halogenated or unhalogenated, that bears a recognition moiety.

When the organic layer is formed from a halogenated organosulfur compound, the organic layer can comprise a single halogenated compound or more than one halogenated compound having different structures. Additionally, these layers can comprise a non-halogenated organosulfur compound.

The reactive functional groups ($X^1$ and $X^2$) are, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc; and (j) epoxides which can react with, for example, amines and hydroxyl compounds. The reactive moieties can also be recognition moieties. The nature of these groups is discussed in greater detail below.

The reactive functional groups can be chosen such that they do not participate in, or interfere with, the reaction controlling the attachment of the functionalized SAM component onto the substrate's surface. Alternatively, the reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

In a preferred embodiment, the SAM component bearing the recognition moiety is attached directly and essentially irreversibly via a "stable bond" to the surface of the substrate. A "stable bond", as used herein, is a bond that maintains its chemical integrity over a wide range of conditions (e.g., amide, carbamate, carbon-carbon, ether, etc.). La another preferred embodiment, the SAM component bearing the recognition moiety is attached to the substrate surface by a "cleaveable bond". A "cleaveable bond", as used herein, is a bond that is designed to undergo scission under conditions which do not degrade other bonds in the recognition moiety-analyte complex. Cleaveable bonds include, but are not limited to, disulfide, imine, carbonate and ester bonds.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the recognition moiety can be controlled. Properties that are usefully controlled include, for example, hydrophobicity, hydrophilicity, surface-activity and the distance of the recognition moiety from the plane of the substrate and/or the SAM. For example, in a SAM composed of alkanethiols, the recognition moiety can be attached to the substrate or the surface of the SAM via an amine terminated poly(ethyleneglycol). Numerous other combinations of spacer arms and SAMs are accessible to those of skill in the art.

The hydrophilicity of the substrate surface can be enhanced by reaction with polar molecules such as amine-, hydroxyl- and polyhydroxyl containing molecules. Representative examples include, but are not limited to, polylysine, polyethyleneimine, poly(ethyleneglycol) and poly(propyleneglycol). Suitable functionalization chemistries and strategies for these compounds are known in the art (See, for example, Dunn, R. L., et al., Eds. POLYMERIC DRUGS AND DRUG DELIVERY SYSTEMS, ACS Symposium Series Vol. 469, American Chemical Society, Washington, D.C. 1991).

The hydrophobicity of the substrate surface can be modulated by using a hydrophobic spacer arm such as, for example, long chain diamines, long chain thiols, α, ω-amino acids, etc. Representative hydrophobic spacers include, but are not limited to, 1,6-hexanediamine, 1,8-octanediamine, 6-aminohexanoic acid and 8-aminooctanoic acid.

The substrate surface can also be made surface-active by attaching to the substrate surface a spacer that has surfactant properties. Compounds useful for this purpose include, for example, aminated or hydroxylated detergent molecules such as, for example, 1-aminododecanoic acid.

In another embodiment, the spacer serves to distance the recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

In another embodiment, the physicochemical characteristics (e.g., hydrophobicity, hydrophilicity, surface activity, conformation) of the substrate surface and/or SAM are altered by attaching a monovalent moiety which is different in composition than the constituents of the bulk SAM and which does not bear a recognition moiety. As used herein, "monovalent moiety" refers to organic molecules with only one reactive functional group. This functional group attaches the molecule to the substrate. "Monovalent moieties" are to be contrasted with the bifunctional "spacer" groups described above. Such monovalent groups are used to modify the hydrophilicity, hydrophobicity, binding characteristics, etc. of the substrate surface. Examples of groups useful for this purpose include long chain alcohols, amines, fatty acids, fatty acid derivatives, poly(ethyleneglycol)monomethyl ethers, etc.

When two or more structurally distinct moieties are used as components of the SAMs, the components can be contacted with the substrate as a mixture of SAM components or, alternatively, the components can be added individually. In those embodiments in which the SAM components are added as a mixture, the mole ratio of a mixture of the components in solution results in the same ratio in the mixed SAM. Depending on the manner in which the SAM is assembled, the two components do not phase segregate into islands (See, Bain and Whitesides, *J. Am. Chem. Soc.* 111:7164 (1989)). This feature of SAMs can be used to immobilize recognition moieties or bulky modifying groups in such a manner that certain interactions, such as steric hindrance, between these molecules is minimized.

The individual components of the SAMs can also be bound to the substrate in a sequential manner. Thus, in one embodiment, a first SAM component is attached to the substrate's surface by "underlabeling" the surface functional groups with less than a stoichiometric equivalent of the first component. The first component can be a SAM component liked to a terminal reactive group or recognition group, a spacer arm or a monovalent moiety. Subsequently, the second component is contacted with the substrate. This second component can either be added in stoichiometric equivalence, stoichiometric excess or can again be used to underlabel to leave sites open for a third component.

III. Recognition Moieties

In some embodiments of the present invention, a "recognition moiety" attached to or associated with the substrate is utilized to bind to or otherwise interact with another molecule or molecules (e.g., analytes) or a cell. For example, in some embodiments, recognition moieties are attached to either ω-functionalized spacer arms or ω-functionalized SAM components that are in turn attached to or associated with the substrate. Furthermore, a recognition moiety can be presented by a polymer surface (e.g., a rubbed polymer surface).

In some preferred embodiments, the recognition moiety comprises an organic functional group. In presently preferred embodiments, the organic functional group is a member selected from the group consisting of amines, carboxylic acids, drugs, chelating agents, crown ethers, cyclodextrins or a combination thereof.

In another preferred embodiment, the recognition moiety is a biomolecule. In still further preferred embodiments, the biomolecule is a polypeptide or protein (e.g., specific receptors or cell receptor recognition sequences [e.g., RGD]), antigen binding protein, peptide, nucleic acid (e.g., single nucleotides or nucleosides, oligonucleotides, polynucleotides and single- and higher-stranded nucleic acids), lipids, phospholipids, or a combination thereof. In a presently preferred embodiment, the recognition moiety is biotin. In some embodiments of the present invention, the recognition moiety is an antigen binding protein. Such antigen binding proteins include, but are not limited to polyclonal, monoclonal, chimeric, single chain, Fab fragments, and Fab expression libraries. In particularly preferred embodiments, the protein and polypeptide recognition moieties comprise proteins and peptide sequences normally found in the extracellular matrix that support cell attachment and function (e.g., collagens including types I, II, III and IV, laminins, fibronectin, vitronectin). In some embodiments, peptide sequences are attached as short functional sequences (e.g., RGD) or the functional sequences may be contained within longer peptide sequences (e.g., x-RGD-x). Examples of peptide sequences include, but are not limited to, all of the known integrin binding sequences, including RGD, EILDV, LDV, LDVP, IDAP, PHSRN, SLDVP, and IDSP.

Various procedures known in the art may be used for the production of polyclonal antibodies. For the production of antibody, various host animals, including but not limited to rabbits, mice, rats, sheep, goats, etc., can be immunized by injection with the peptide corresponding to an epitope. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In addition, it is contemplated that techniques described for the production of single chain antibodies (U.S. Pat. No. 4,946,778; herein incorporated by reference) will find use in producing specific single chain antibodies that serve as recognition moieties. Furthermore, it is contemplated that any technique suitable for producing antibody fragments will find use in generating antibody fragments that are useful recognition moieties. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent. In still further embodiments, the recognition moiety comprises a phage displaying an antigen binding protein.

In some embodiments where the recognition moiety is a polynucleotide or polypeptide, a plurality of recognition moieties are arrayed on the substrates using photo activated chemistry, microcontact printing, and ink-jet printing. In particularly preferred embodiments, photolithography is utilized (See e.g., U.S. Pat. Nos. 6,045,996; 5,925,525; and 5,858,659; each of which is herein incorporated by reference). Using a series of photolithographic masks to define substrate exposure sites, followed by specific chemical synthesis steps, the process constructs high-density arrays of oligonucleotides, with each probe in a predefined position in the array. Multiple probe arrays are synthesized simultaneously on, for example, a large glass wafer. The wafers are then diced, and individual probe arrays are packaged in injection-molded plastic cartridges, which protect them from the environment and serve as chambers for hybridization.

In other embodiments, nucleic acid recognition moieties are electronically captured on a suitable substrate (See e.g., U.S. Pat. Nos. 6,017,696; 6,068,818; and 6,051,380; each of which are herein incorporated by reference). Through the use of microelectronics, this technology enables the active movement and concentration of charged molecules to and from designated test sites on its semiconductor microchip. DNA capture probes unique to a given target are electronically placed at, or "addressed" to, specific sites on the microchip. Since DNA has a strong negative charge, it can be electronically moved to an area of positive charge.

In still further embodiments, recognition moieties are arrayed on a suitable substrate by utilizing differences in surface tension (See e.g., U.S. Pat. Nos. 6,001,311; 5,985,551; and 5,474,796; each of which is herein incorporated by reference). This technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

In still further embodiments, recognition moieties are spotted onto a suitable substrate. Such spotting can be done by hand with a capillary tube or micropipette, or by an automated spotting apparatus such as those available from Affymetrix and Gilson (See e.g., U.S. Pat. Nos. 5,601,980; 6,242,266; 6,040,193; and 5,700,637; each of which is incorporated herein by reference).

When the recognition moiety is an amine, in preferred embodiments, the recognition moiety will interact with a structure on the analyte that reacts by binding to the amine (e.g., carbonyl groups, alkylhalo groups). In another preferred embodiment, the amine is protonated by an acidic moiety on the analyte of interest (e.g., carboxylic acid, sulfonic acid).

In certain preferred embodiments, when the recognition moiety is a carboxylic acid, the recognition moiety will interact with the analyte by complexation (e.g., metal ions). In still other preferred embodiments, the carboxylic acid will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds that are being screened for their ability to interact with an analyte of choice. As such, drug moieties that are useful in practicing the instant invention include drugs from a broad range of drug classes having a variety of pharmacological activities.

Classes of useful agents include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniranune, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); P-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole; pentamidine, gentamycin, kanamycin, lineomycin, methacycline, methenamine, minocycline, neomycin, netilmycin, paromomycin, streptomycin, tobramycin, miconazole, and amanfadine, anti-microbial peptides including but not limited to alpha and beta defensins, magainins, cecropins, bactenecins and indolicidin.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, a-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin, thyrotropin releasing hormone, angiotensin II, other small peptide hormones, as well as phospholipic hormones such as Lysophosphatidic acid, platelet activating factor and eicosanoids); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triameinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

When the recognition moiety is a chelating agent, crown ether or cyclodextrin, host-guest chemistry will dominate the interaction between the recognition moiety and the analyte. The use of host-guest chemistry allows a great degree of recognition-moiety-analyte specificity to be engineered into a device of the invention. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279-312; Lindoy, L. F., THE CHEMISTRY OF MACROCYCLIC LIGAND COMPLEXES; Cambridge University Press, Cambridge, 1989; Dugas, H., BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, R. E., Whitaker, 1. R., Eds., American Chemical Society, Washington, D.C., 1982, pp. 370-387; Kasina et al. *Bioconjugate Chem.* 9:108-117 (1998); Song et al., *Bioconjugate Chem.* 8:249-255 (1997).

In a presently preferred embodiment, the recognition moiety is a polyaminocarboxylate chelating agent such as ethylenediaminetetraacetic acid (EDTA) or diethylenetriaminepentaacetic acid (DTPA). These recognition moieties can be attached to any amine-terminated component of a SAM or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, phospholipid fatty acid derivative, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies, structural proteins, transcription factors and receptors. Antibodies can be either polyclonal or monoclonal. Peptides, lipids, carbohydrates and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the e-amine groups of lysine residues. Furthermore, these molecules can be adsorbed onto the surface of the substrate or SAM by non-specific interactions (e.g., chemisorption, physisorption).

Recognition moieties that are antibodies can be used to recognize analytes that are proteins, peptides, nucleic acids, lipids, phoshpolipids, lipopolysaccharides, saccharides or small molecules such as drugs, herbicides, pesticides, infectious agents, industrial chemicals and agents of war. Methods of raising antibodies for specific molecules are well-known to those of skill in the art. See, U.S. Pat. Nos. 5,147,786; 5,334, 528; 5,686,237; 5,573,922; each of which is incorporated herein by reference. Methods for attaching antibodies to surfaces are also art-known (See, Delamarche et al. *Langmuir* 12:1944-1946 (1996)).

Peptides and nucleic acids can be attached to a SAM component or spacer arm. Both naturally-derived and synthetic peptides and nucleic acids are of use in conjunction with the present invention. These molecules can be attached to a SAM component or spacer arm by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). Polysaccharides, phospholipids, fatty acid derivatives and other lipids can be attached via hydroxyl groups on the sugar moiety or the lipid portion as well as via free carboxyl or amino groups. The peptide and nucleic acid chains can be further derivatized at one or more sites to allow for the attachment of appropriate reactive groups onto the chain (See, Chrisey et al. *Nucleic Acids Res.* 24:3031-3039 (1996)).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art (See, for example, THE PEPTIDES: ANALYSIS, SYNTHESIS, BIOLOGY, Vol. 2: "Special Methods in Peptide Synthesis," Gross, E. and Melenhofer, J., Eds., Academic Press, New York (1980)). Many useful monomers are commercially available (Bachem, Sigma, etc.). This masked group can then be unmasked following the synthesis, at which time it becomes available for reaction with a SAM component or a spacer arm.

In other preferred embodiments, the peptide is attached directly to the substrate (See, Frey et al. *Anal. Chem.* 68:3187-3193 (1996)). In a particularly preferred embodiment, the peptide is attached to a gold substrate through a sulfhydryl group on a cysteine residue. In another preferred embodiment, the peptide is attached through a thiol to a spacer arm that terminates in, for example, an iodoacetamide, chloroacetamide, benzyl iodide, benzyl bromide, alkyl iodide or alkyl bromide. Similar immobilization techniques are known to those of skill in the art (See, for example, Zull et al. *J. Ind Microbiol.* 13:137-143 (1994)).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure that has a basket-like shape. This shape allows cyclodextrins to include many kinds of molecules into their internal cavity (See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978).

Cyclodextrins are able to form inclusion complexes with an array of organic molecules including, for example, drugs, pesticides, herbicides and agents of war (See, Tenjarla et al., *J. Pharm. Sci.* 87:425-429 (1998); Zughul et al., *Pharm. Dev. Technol.* 3:43-53 (1998); and Albers et al., *Crit. Rev. Ther. Drug Carrier Syst.* 12:311-337 (1995)). Importantly, cyclodextrins are able to discriminate between enantiomers of compounds in their inclusion complexes. Thus, in one preferred embodiment, the invention provides for the detection of a particular enantiomer in a mixture of enantiomers (See, Koppenhoefer et al. *J. Chromatogr. A* 793:153-164 (1998)).

The cyclodextrin recognition moiety can be attached to a SAM component, through a spacer arm or directly to the substrate (See, Yamamoto et al., *J. Phys. Chem. B* 101:6855-6860 (1997)). Methods to attach cyclodextrins to other molecules are well known to those of skill in the chromatographic and pharmaceutical arts (See, Sreenivasan, *Appl. Polym. Sci.* 60:2245-2249 (1996)).

IV. Mesogenic Layer

Any compound or mixture of compounds that forms a mesogenic layer can be used in conjunction with the present invention. The mesogens can form thermotropic or lyotropic liquid crystals. The mesogenic layer can be either continuous or it can be patterned.

Both the thermotropic and lyotropic liquid crystals can exist in a number of forms including nematic, chiral nematic, smectic, polar smectic, chiral smectic, frustrated phases and discotic phases.

TABLE 1

| Molecular structure of mesogens suitable for use in Liquid Crystal Assay Devices | |
|---|---|
| Mesogen | Structure |
| Anisaldazine | 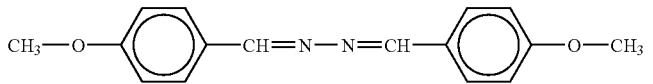 |
| NCB | 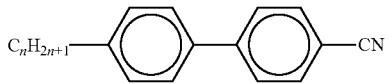 |
| CBOOA | 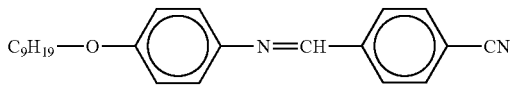 |
| Comp A | 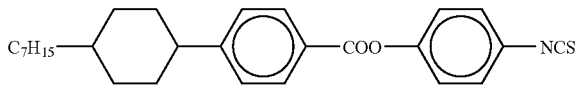 |
| Comp B | 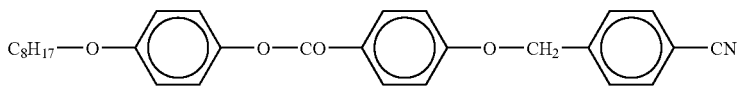 |
| DB$_7$NO$_2$ | 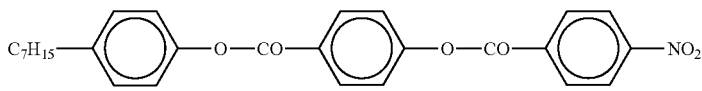 |
| DOBAMBC | 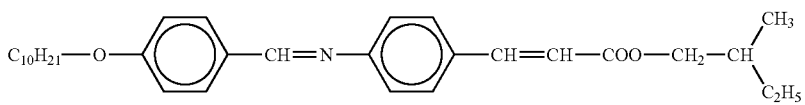 |

TABLE 1-continued

Molecular structure of mesogens suitable for use in Liquid Crystal Assay Devices

| Mesogen | Structure |
| --- | --- |
| $n$O$m$<br>$n = 1, m = 4$: MBBA<br>$n = 2, m = 4$: EBBA | $C_nH_{2n+1}$—O—⟨phenyl⟩—CH=N—⟨phenyl⟩—$C_mH_{2m+1}$ |
| $n$OBA<br>$n = 8$: OOBA<br>$n = 9$: NOBA | $C_nH_{2n+1}$—O—⟨phenyl⟩—COOH |
| $nm$OBC | $C_nH_{2n+1}$—O—CO—⟨phenyl⟩—⟨phenyl⟩—O—$C_mH_{2m+1}$ |
| $n$OCB | $C_nH_{2n+1}$—O—⟨phenyl⟩—⟨phenyl⟩—CN |
| $n$OSI | $C_nH_{2n+1}$—O—⟨phenyl⟩—⟨phenyl⟩—COO—⟨phenyl⟩—CH$_2$—CH(CH$_3$)(C$_2$H$_5$) |
| 98P | $C_3H_7$—[CH$_2$(CH$_3$)]$_5$—O—⟨phenyl⟩—⟨pyrimidine⟩—$C_8H_{17}$ |
| PAA | CH$_3$—O—⟨phenyl⟩—N=N(O)—⟨phenyl⟩—O—CH$_3$ |
| PYP906 | $C_9H_{19}$—⟨pyrimidine⟩—⟨phenyl⟩—O—$C_6H_{13}$ |
| $\overline{n}$S$m$ | $C_nH_{2n+1}$—O—⟨phenyl⟩—CO—S—⟨phenyl⟩—$C_mH_{2m+1}$ |

Presently preferred mesogens are displayed in Table 1. In a particularly preferred embodiment, the mesogen is a member selected from the group consisting of 4-cyano-4'-pentylbiphenyl, N-(4methoxybenzylidene)-4-butlyaniline and combinations thereof.

The mesogenic layer can be a substantially pure compound, or it can contain other compounds that enhance or alter characteristics of the mesogen. Thus, in one preferred embodiment, the mesogenic layer further comprises a second compound, for example an alkane, which expands the temperature range over which the nematic and isotropic phases exist. Use of devices having mesogenic layers of this composition allows for detection of the analyte recognition moiety interaction over a greater temperature range.

In some preferred embodiments, the mesogenic layer further comprises a dichroic dye or fluorescent compound. Examples of dichroic dyes and fluorescent compounds useful in the present invention include, but are not limited to, azobenzene, BTBP, polyazocompounds, anthraquinone, perylene dyes, and the like. In particularly preferred embodiments, a dichroic dye of fluorescent compound is selected that complements the orientation dependence of the liquid crystal so that polarized light is not required to read the assay. In some preferred embodiments, if the absorbance of the liquid crystal is in the visible range, then changes in orientation can be observed using ambient light without crossed polars. In other preferred embodiments, the dichroic dye or fluorescent compound is used in combination with a fluorimeter and the changes in fluorescence are used to detect changes in orientation of the liquid crystal.

In another preferred embodiment, the analyte first interacts with the recognition moiety and the mesogenic layer is introduced in its isotropic phase. The mesogenic layer is subsequently cooled to form the liquid crystalline phase. The presence of the analyte within regions of the mesogenic layer will disturb the equilibrium between the nematic and isotropic phases leading to different rates and magnitudes of nucleation at those sites. The differences between the nematic and isotropic regions are clearly detectable.

V. Patterned (Ordered) Liquid Crystals

One approach to the patterning of the mesogenic layer on flat and curved surfaces is based on the use of patterned SAMs of molecules to direct both the polar (away from the surface) and azimuthal (in the plane of the surface) orientations of the mesogenic layer. This method is simple and flexible, and any of the recently established procedures for patterning SAMs on surfaces (for example, microcontact printing or photo-patterning) (Talov et al., J. Am. Chem. Soc. 115: 5305 (1993); Kumar et al., Acc. Chem. Res. 28: 219 (1995), and references therein; Xia et al., J. Am. Chem. Soc. 117: 3274 (1995), and references therein can be used; Jackman et al., Science 269: 664 (1995)). Using any of these methods, SAMs which pattern liquid crystals can be easily extended to sizes ranging from hundreds of nanometers (Xia et al., J. Am. Chem. Soc. 117: 3274 (1995), and references therein) to millimeters and permit both planar (parallel to the surface) and homeotropic perpendicular to the surface) orientation of mesogenic layers; methods based on the rubbing of polymer films mainly provide manipulation of the in-plane alignment of mesogenic layers and cannot homeotropically align mesogenic layers. One class of useful SAMs has surface energies (~19 mJ/m$^2$) about half those of films of polyimides used for alignment of liquid crystals; low-energy surfaces are less prone to contamination by molecular adsorbates and dust particles than are high-energy ones. Because SAMs can also be patterned on non-planar surfaces (Jackman et al., Science 269: 664 (1995)), patterned mesogenic structures formed with SAMs can be replicated on curved surfaces.

The capacity to pattern mesogenic layer orientations on nonplanar surfaces provides procedures for the fabrication of tunable hybrid diffractive-refractive devices. For example, devices based on combinations of diffractive and refractive optical processes permit aplanatic or chromatic correction in lenses, spectral dispersion, imaging from a single optical element, and other manipulations of light (Resler et al., Opt. Lett. 21, 689 (1996); S. M. Ebstein, ibid., p. 1454; M. B. Stem, Microelectron. Eng. 32, 369 (1996): Goto et al., Jpn. J. Appl. Phys. 31, 1586 (1992); Magiera et al., Soc. Photo-Opt. Instrum. Eng., 2774, 204 (1996)). The capability to pattern mesogenic layers on curved surfaces also provides routes for the fabrication of displays with wide viewing angles.

In a presently preferred embodiment, the tunable hybrid device permits the manipulation of light. In a further preferred embodiment, the device is a refractive-diffractive device. In a still further preferred embodiment, the device permits imaging from a single optical element. In yet another preferred embodiment, the device permits aplanatic or chromatic correction in lenses. In still another preferred embodiment, the device allows for spectral dispersion.

In another presently preferred embodiment, the SAM is layered on a material suitable for use as an electrode. In a preferred embodiment, the material is a metal film. In a further preferred embodiment, the metal film is a gold film.

The patterned mesogenic layers of the present invention can be tuned by the use of electric fields. In a preferred embodiment, the electric field is used to reversibly orient the mesogenic layer. In a still further preferred embodiment, the electric field is applied either perpendicular to, or in the plane of, the surface of the mesogenic layer. In another preferred embodiment, the oriented mesogenic layer modulates the intensity of light diffracted from the layer.

The discussion above, concerning SAM components, SAM components with reactive groups and SAM components bearing recognition moieties is equally applicable in the context of this aspect of the invention. Thus, the constituents of the SAM can be chosen from any of a wide variety of appropriate molecules. In a presently preferred embodiment, the SAM comprises mixtures of $R^{21}CH_2(CH_2)_{14}SH$ and $R^{31}CH_2(CH_2)_{15}SH$, where $R^{21}$ and $R^{31}$ are independently members elected from the group consisting of hydrogen, reactive groups and recognition groups, as discussed above.

VI. Analytical Devices

The device of the present invention can be of any configuration that allows for the contact of a mesogenic layer with an organic layer or inorganic layer (e.g., metal, metal salt or metal oxide). The only limitations on size and shape are those that arise from the situation in which the device is used or the purpose for which it is intended. The device can be planar or non-planar. Thus, it is within the scope of the present invention to use any number of polarizers, lenses, filters, lights, and the like to practice the present invention.

Although many changes in the mesogenic layer can be detected by visual observation under ambient light, any means for detecting the change in the mesogenic layer can be incorporated into, or used in conjunction with, the device. Thus, it is within the scope of the present invention to use lights of various sources, microscopes, spectrometry, electrical techniques and the like to aid in the detection of a change in the mesogenic layer.

In those embodiments utilizing light in the visible region of the spectrum, the light can be used to simply illuminate details of the mesogenic layer. Alternatively, the light can be passed through the mesogenic layer and the amount of light transmitted, absorbed or reflected can be measured. The device can utilize a backlighting device such as that described in U.S. Pat. No. 5,739,879, incorporated herein by reference. Light in the ultraviolet and infrared regions is also of use in the present invention.

Thus, in another aspect, the invention provides a method for varying the optical texture of a mesogenic layer comprising a haloorganosulfur. The optical texture of the mesogenic layer is controlled by selecting the halogen content of the haloorganosulfur. The following sections describe a number of novel devices according to the present invention.

A. Coated Slides

In some embodiments, the assay dev of the present invention are produced by coating the various assay formats herein on a substrate through which light can pass (e.g., transparent and opaque substrates). The present invention is not limited to the use of any particular type of substrate. Indeed, the use of a variety substrates is contemplated, including, but not limited to silica and quartz substrates. In some embodiments, the substrates have the same dimensions as commercially available slides (e.g., microscope slides), while in other embodiments, the dimensions of the substrates are varied to correspond to the end use or to the type of machine used to analyze the substrate (e.g., a plate reader).

In preferred embodiments, areas of anisotropic order (i.e., analytic zones) are created on the slide prior to or after coating of the assay format on the slide. In either case, the area of anisotropic order orients liquid crystals. In preferred embodiments, the area of anisotropic order occupies substantially all of the substrate surface, while in other embodiments, discreet areas of anisotropy are formed. Methods of creating such areas, which are described in more detail elsewhere herein, include, but are not limited to, oblique deposition of metals such as gold, rubbing the substrate surface with a soft material such a cloth or an abrasive material, nano-abrasion with a gas stream containing abrasive particles (e.g., silica), etching with liquid, and immobilization of proteins on the substrate following by rubbing.

The present invention is not limited to any particular number of areas of anisotropic order. Indeed, the number of such areas, or analytic zones, can vary from 1 to a plurality zones (e.g., from 1 to 1534 zones). In some embodiments, the analytic zones correspond to the dimensions and spatial distribution of standard commercial multiwell plates. It is contemplated that this distribution of analytic zones allows analysis with commercial multiwell plate readers. In other embodiments, the analytic zones can be smaller or larger than the dimensions of wells in standard multiwell plates. In further embodiments, the analytic zones correspond to dimensions at least equal to the field of view of a microscope objective (e.g., a 5×, 10×, or 20× objective). It is contemplated that this configuration facilitates integration with automated microscopy systems.

In some preferred, embodiments, substrates upon which areas of anisotropy have been created are coated with a coating material. In some embodiments, the coating is accomplished through use of commercially known procedures such as silk screen printing, flexographic printing, microcontact printing, seriagraphic printing, ink-jet printing, intaligo printing, off-set printing, Heidelberg press printing, and thermal laser printing. The present invention is not limited to the use of any particular coating material. Indeed, the use of a variety of coating materials is contemplated, including hydrophobic coating materials, hydrophilic coating materials, coating materials containing electroconductive elements, and coating materials containing electroinsulating materials. Specific examples of such materials include, but are not limited to, polyurethane, polyethylene, GORTEX (polytetrafluoroethylene), DACRON (polyethylene tetraphthalate), TEFLON (polytetrafluoroethylene), PVDF (polyvinylidene difluoride), proteins such as BSA, latex, polystyrene, silicone, cellulose, and nitrocellulose. In preferred embodiments, the coating material is applied to form the assay formats described in more detail elsewhere herein. In still further embodiments, the coating material is applied so as to create microfluidic channels (see, e.g., U.S. Pat. No. 6,509,085, which is hereby incorporated by reference). Where necessary, the coating material is cured (e.g., by UV irradiation or infrared radiation) following application to the substrate.

The thickness of the coating material applied can vary. In some preferred embodiments, the thickness is from about 1 micrometer to about 100 micrometers, in more preferred embodiments, the thickness is from about 5 micrometer to about 35 micrometers, and in most preferred embodiments, the thickness is from about 20 micrometers to about 25 micrometers.

In further preferred embodiments, a pigment is included in the coating material so that non-coated areas transmit light while coated areas substantially block the transmission of light. The present invention is not limited to the use of any particular pigment. Indeed, the use of a variety of pigments is contemplated, including black, red and blue pigments.

In some embodiments, a second untreated or treated substrate (e.g., a glass slide) is placed on the coated slide prior to curing. Pressure is then applied to the substrates so that upon curing, the two substrates adhere to one another. In some embodiments, the pressure is applied by transporting the paired substrates through a roller. The paired substrates are then cured to produce an optical cell.

In still further embodiments, the coating material comprises a pressure sensitive adhesive. In some embodiments, the coating material comprising a pressure sensitive adhesive defines one to a plurality of analytic zones. In some embodiments, the coating material comprising a pressure sensitive adhesive further comprises a pigment. In preferred embodiments, the pigment is black. In still further embodiments, the coating material comprising a pressure sensitive adhesive comprises a polymeric coating material (e.g., acrylic or TEFLON polymer) to provide a hybrid coating material. In some preferred embodiments, the pressure sensitive adhesive is low tack.

In other embodiments, the pressure sensitive adhesive is printed onto the substrate after printing with another coating material. The pattern of pressure sensitive adhesive printed onto the substrate can have a variety of configurations. For example, in some embodiments, the pressure sensitive adhesive is printed in a rectangular outline around an analytic zone. In other embodiments, the pressure sensitive adhesive is applied in a plurality of points on the perimeter of the substrate. In still other embodiments, the pressure sensitive adhesive is applied only to the second untreated substrate that is used to cover the first substrate comprising the analytic zone(s). In some embodiments, the pressure sensitive adhesive is a double-sided tape comprises a removable backing that can be removed prior to assembly of the optical cell. In other embodiments, the double sided tape does not comprise a removable backing.

As described above, in preferred embodiments the coating material is applied to create microfluidic channels. In some embodiments, the microfluidic channels allow the fluidic movement of samples placed in an entry port on the substrate to an analytic zone. In some preferred embodiments, the top substrate comprises reservoirs for receiving samples, rinse solutions, or liquid crystal solutions. The microfluidic channels are in fluid communication with the reservoirs and terminate in outlet ports. In preferred embodiments, the microfluidic channels are of a dimension such that small variations in chamber pressure will not appreciably effect flow rates.

Motive force for delivery of fluids (e.g., samples, wash solution, or liquid crystals) via the microfluidic channels is supplied in a variety of ways, including, but not limited to, syringe pumps, disposable Medicell pumps, placement of wicking materials at the outlet port, drop pumping (i.e., movement from small drop to large drop), placement over a fluid column over an inlet port, placement of positive atmospheric pressure at inlet ports and/or placement of negative atmospheric pressure at outlet ports. It is contemplated that positive pressure can be delivered via use of a substantially sealed chamber in conjunction with an air pump or bottled gas (e.g., nitrogen gas). Likewise, negative pressure can be delivered via use of a substantially sealed chamber in conjunction with a vacuum pump. A vacuum may be applied by a variety of methods, including, but not limited to, use of running water and a venturi valve, AC or DC pumps, spring loaded negative syringe pump or deformable sphere with elasticity such as a bulb syringe pipettor.

In some embodiments, assay devices comprising a substrate having at least one microchannel therein are utilized to quantify the amount of an analyte in a sample. It must be noted that these embodiments are not limited to assay devices fabricated in any particular manner. For example, in some embodiments, the assay devices comprising microchannels are fabricated by printing, while in other embodiments, the assay devices comprising microchannels are fabricated by micromolding or lithography. In some embodiments, the microchannel comprises at least one surface that orients a liquid crystal. Such surfaces may be fabricated by a variety means, including, but not limited to, nanoabrasion, rubbing, and oblique deposition of metals. In further preferred embodiments, the microchannel, including the surface that orients a liquid crystal, is decorated with a recognition moiety. Methods for attaching recognition moieties are describes in detail above. As needed, the substrate also preferably includes reservoirs and ports for introducing samples, assay reagents (e.g., mesogens) and wash solutions into the microchannel. In each case, the reservoir or port is fluidically connected to the relevant microchannel.

In operation, a sample suspected of containing an analyte is allowed to flow through the microchannel under conditions where analytes present in the sample can bind to the recognition moiety. Mesogens are then applied to microchannel and the substrate is analyzed for the presece or absence of liquid crystal ordering. Analysis of the liquid crystal can be be conducted by any of the means described in more detail herein, including, but not limited to, a microscope equipped with polarizing lenses and a plate reader. It is contemplated that areas where there is recognition moiety-substrate binding will be identified by a lack of order in the liquid crystal, while areas in which there is no binding will be identifiable by the presence of an ordered liquid crystal. Moreover, because the sample is allowed to flow along the length of the microfluidic channel, binding is greater at the point entry into the channel as opposed to the distal end of the channel. In other words, the amount of analyte in the sample is depleted as the sample flows along the channel. This effect may be used to quantify the amount of analyte in the sample, which is proportional the to length of the microchannel over which liquid crystal order is disrupted.

In some embodiments, the substrate comprises a plurality of microchannels so that serial dilutions of the sample may be applied in parallel to provide accurate quantitation of the amount of analyte in a sample. In other embodiments, test samples are compared to control samples by running the samples in parallel in separate microfluidic channels. The difference in areas of the microchannels over which liquid crystal disorder is disrupted is proportional to the amount of analyte in the test sample. Example 5 provides an example of this method.

B. Plate Readers

The present invention contemplates the use of plate readers to detect changes in the orientation of mesogens upon binding of an analyte. The plate readers may be used in conjunction with the LC assay devices described herein and also with the lyotropic LC assays described in U.S. Pat. No. 6,171,802, incorporated herein by reference. In particular, the present invention includes methods and processes for the quantification of light transmission through films of liquid crystals based on quantification of transmitted or reflected light.

The present invention is not limited to any particular mechanism of action. Indeed, an understanding of the mechanism of action is not required to practice the present invention. Nevertheless, it is contemplated that ordered nanostructured substrates impart order to thin films of liquid crystal placed onto their surface. These ordered films of liquid crystal preserve the plane of polarized light passed through them. If the liquid crystal possesses a well-defined distortion—such as a 90 degree twist distortion—then the liquid crystal will change the polarization of the transmitted light in a well-defined and predictable manner. It is further contemplated that ordered films of liquid crystal differentially absorb (relative to randomly ordered films of liquid crystal) specific wavelengths of light.

In some embodiments of the present invention, the amount of target molecule or molecules bound to a sensing surface of an LC assay device (i.e., a surface decorated with a recognition moiety) increases with the concentration/amount of target molecule present in a sample in contact with a sensing surface. In preferred embodiments, the amount of bound target molecule changes the degree of disorder introduced into a thin film of liquid crystal that is ordered by nature of the underlying nanostructured sensing substrate. In some embodiments, the degree of order present in a thin film of liquid crystal determines the amount of light transmitted through the film when viewed through crossed polars. In other embodiments, the degree of order present in a thin film of liquid crystal determines the amount of light transmitted through the film when viewed using specific wavelengths of light. In still other embodiments, the reflectivity of an interface to a liquid crystal can change with the orientation of the liquid crystal. Therefore, in some embodiments, oblique illumination of the LC assay device is utilized with collection and analysis of reflected light being performed.

Accordingly, the present invention contemplates the use of plate readers to detect light transmission through an LC assay device when viewed through cross or parallel polars, the transmission of light through an LC assay device illuminated with a suitable wavelength of light, or reflection of light (i.e., polarized light or non-polarized light of specific wavelengths) from the surface of an LC assay device. In particularly preferred embodiments, plate readers are provided that are designed to be used in conjunction with LC assays. Other embodiments of the present invention provide modified commercially available readers such as ELISA readers and fluorometric readers adapted to read LC assays.

Non-limiting examples of the plate readers adapted for use in the present invention may be found in WO 03/019,191, which is herein incorporated by reference. In preferred embodiments, two polarizing filters are placed in the optical pathway of the plate reader in a crossed or parallel polar configuration. One filter is placed on the emission side of the light path prior to passing through the sample while a second polarizing filter is placed on the analyzing side of the light path after light has passed through the sample but before it is collected by a sensing devise such as a photodiode, a photomultiplier or a CCD. An ordered liquid crystal in the LC assay device preserves the plane of polarization and the amount of light reaching the light gathering and sensing device is markedly attenuated when viewed through cross polars or markedly accentuated when viewed through parallel polars. Random organization of the liquid crystal of the LC assay device does not preserve the plane of polarization and the amount of light, passing through crossed polars, reaching the light collecting and sensing device is relatively unaffected. Accordingly, in preferred embodiments, the binding of target molecules by the recognition moieties in an LC assay device introduces disorder into the overlying thin film of LC that increases with the amount of bound target molecule. In other preferred embodiments, the presence of a cell on an ordered region introduces disorder into the overlying LC. In other embodiments, specific bandpass filters are placed on the excitation side of the light path before light encounters the sample as well as on the emission side of the light path (after light has passed through or is reflected by the sample but before reaching the light collecting and sensing device (e.g., photodiode, photomultiplier or CCD). This configuration is useful for quantifying both reflected and transmitted light.

The present invention also provides LC assay devices configured for use in the plate reader. In preferred embodiments, the LC assay device is formatted or arrayed according to the dimensions of standard commercially available plates (e.g., 24, 96, 384 and 1536 well plates). In some embodiments, the LC assay device comprises a surface (e.g., a substrate with recognition moieties attached) that is of proper external dimensions to be accurately fit into a given commercial reader. In some embodiments, the substrate contains uniform topography across its surface, in other embodiments, the substrate contains a gradient of topographies across its surface whereas in yet other embodiments regions of topography are limited to discrete regions that correspond to areas read out by commercial plate readers. The recognition moieties may be arrayed on the substrate surface in any appropriate configuration. For example, in some embodiments, a single binding antibody, polypeptide or protein, phospholipid, polynucleotide, or carbohydrate is evenly distributed across the surface. In other embodiments, a single binding antibody, polypeptide or protein, phospholipid, polynucleotide, or carbohydrate is distributed across the surface in a gradient. In still other embodiments, a single binding antibody, polypeptide or protein, phospholipid, polynucleotide, or carbohydrate is arrayed in discrete spots that are in proper alignment to be read by the commercial reader. In still further embodiments, a variety of different single binding antibodies, polypeptides or proteins, phospholipids, polynucleotides, or carbohydrates are arrayed in spots that are in proper alignment to read by the commercial reader. In still other embodiments, a variety of different single binding antibodies, polypeptides or proteins, phospholipids, polynucleotides, or carbohydrates are arrayed in zones along the surface. Each zone contains a different polypeptide or protein, cell receptor or binding sequence. The plate is read at predetermined points (e.g., spots corresponding to the location of the wells in a 96 well plate). By designing the zones to the configuration of the plate reader it will be known which "well" readings correspond to each zone. In other embodiments, specifically designed well inserts (to be used with commercially available 6, 12, 24, 96, 384 or 1536 well plates) containing the nanostructured sensing surface will be used in conjunction with commercially available multiwell plates for performing the LC assays.

In some embodiments, plate readers are utilized to identify a reaction front in a microfluidic channel. In these embodiments, a substrate is provided in which the position of one or more microfluidic channels in the substrate corresponds to the position of a row of wells in a commercial multiwell plate. The plate reader is then utilized to read discreet areas along the microfluidic channel. It is contemplated that this method will allow detection of how far along a microchannel that a given reaction (i.e., binding of an analyte to a recognition moiety) occurs. The distance of the reaction can then be used to quantify the amount of analyte present. It will be recognized that the spatial resolution of the readout can be increased by reading more areas along the microfluidic channel. This can be accomplished by utilizing plate readers configured to read out 1534 well plates.

Additionally, some microplate readers have a scanning mode wherein the reading element performs a scan of assigned diagnostic regions corresponding to well locations in a multiwell plate. The present invention contemplates the use of such readers to read out multiple locations along a microfluidic channel so that a reaction front is identified. Alternatively, the scanning reader is utilized to scan the length of a microfluidic channel to identify a reaction front. Likewise, a plate reader can be used to measure a linear area of response on the surface of a substrate exposed to an analyte. In this embodiment, the reaction is not confined to a microfluidic channel, but instead is allowed to proceed across one or more areas on a substrate surface. Multiple analytic zones programmed into the plate reader are then read out to determine the extent of the one or more areas over which a reaction (e.g., disruption of liquid crystal order by migration of cells) has occurred. Software can be modified to optimize both the location and movement of the sensing elements of the plate reader as well as subsequent analysis of the biophotonic output. For example, the sensing elements are programmed to obtain multiple discreet readings or continuous linear scans from predetermined analytic zones currently employed by commercial plate readers (e.g., corresponding to well locations of 24, 96, 384 or 1536 plates) or could be programmed to obtain readings front novel locations that correspond to novel plate designs for use with the assays described in detail in this document. It will be recognized that these devices and methods are not limited to use with liquid crystal assays, but instead are broadly applicable to different assays such a fluorescent, calorimetric, and densitometric assays.

In some embodiments (for example, cell migration or movement assays), the plate reading device is configured to sample multiple regions within in a given assay region. For example, the plate reader can be configured to provide multiple circular readouts within a circular region defined by a well of a multiwell plate. Thus, the presence of cells can be detected in regions that are remote from a central cell seeding area. As another example, the plate reader is configured to provides readouts in concentric circles originating from a central cell seeding region. In this embodiment, the number of cells within each successive concentric circle provides information as to the extent of migration (for example, in response to a test compound). The area under the curve for the signal from each successive concentric circle can be measured and plotted (signal vs. zone) to provide an analysis of strength of response to a test compound.

In other embodiments, the plate reading device is configured asymmetrically sample a well or other assay region, for example, the right or left side of a central cell seeding zone. It is contemplated that such asymmetric sampling will yield data that distinguished chemotaxis from chemokinesis. For example, if the number of cells in the right and left regions is equal, the compound is chemokinetic. If the cell signal is strongest in the region with the highest amount test compound, then the compound is chemotactic. It will also be recognized that the plate reader can be configured as described above so that the multiple discrete regions are read within a given assay region. Chemokinesis is indicated by randomly distributed cells, while chemotaxis is indicated by an increased number of cells in sample areas oriented closer to a test compound source as opposed to areas more remote from a test compound source.

It will also be recognized that the present invention provides an assay system comprising a plate reading device and an LC assay device, wherein the plate reading device and LC assay device are configured so that light provided from the plate reading device which is passed through or reflected from at least one surface of the LC assay device is detected by a detection unit of the plate reading device. Suitable detecting units include CCDs, photodiodes and photomultiplier tubes.

In other embodiments, imaging systems (e.g., array reading systems and gel readers) may be utilized that image the entire plate or a portion thereof (e.g., individual wells) at once. The data obtained from such systems is then processed to provide information on individual assay areas with the plates or wells. Such imaging systems can preferably utilize optical imaging devices such as CCDs or other imaging devices such as magnetic resonance imagers.

Commercially available plate readers that may be modified according to the present invention include, but are not limited, to those available from Nalge Nunc International Corporation (Rochester, N.Y.), Greiner America, Inc. (Lake Mary, Fla.), Akers Laboratories Inc., (Thorofare, N.J.), Alpha Diagnostic International, Inc. (San Antonio, Tex.), Biotek Instruments, Inc., (Winooski, Vt.), Tecan U.S. (Durham, N.C.), and Qiagen Inc. (Valencia, Calif.).

3. Substrate Holder for use with Multiwell Plate Readers

In some embodiments, the present invention provides substrate holders for use with multiwell plate readers. In preferred embodiments, the dimensions of the slide holder correspond to the dimensions of commercial multiwell plates so that the substrate (e.g., a slide or optical cell made from slides)

can be placed in the holder and the holder placed in a multiwell plate reader. In some embodiments, the substrate holder is configured to accept a plurality of substrates (e.g., 2-4 substrates). Once the substrate holder containing the substrate(s) is placed in plate reader, the analytical zones can be read by the plate reader. Accordingly, in preferred embodiments, the individual substrates are held in such a position such that the analytic zones of the substrates correspond to the spatial location of wells in commercial multiwell plates. The substrate holder can be constructed from a variety of materials, including, but not limited to, stainless steel, titanium, aluminum, aluminum alloys, polymeric materials such as plexiglass or polycarbonate, wood, and glass.

Figure 48:
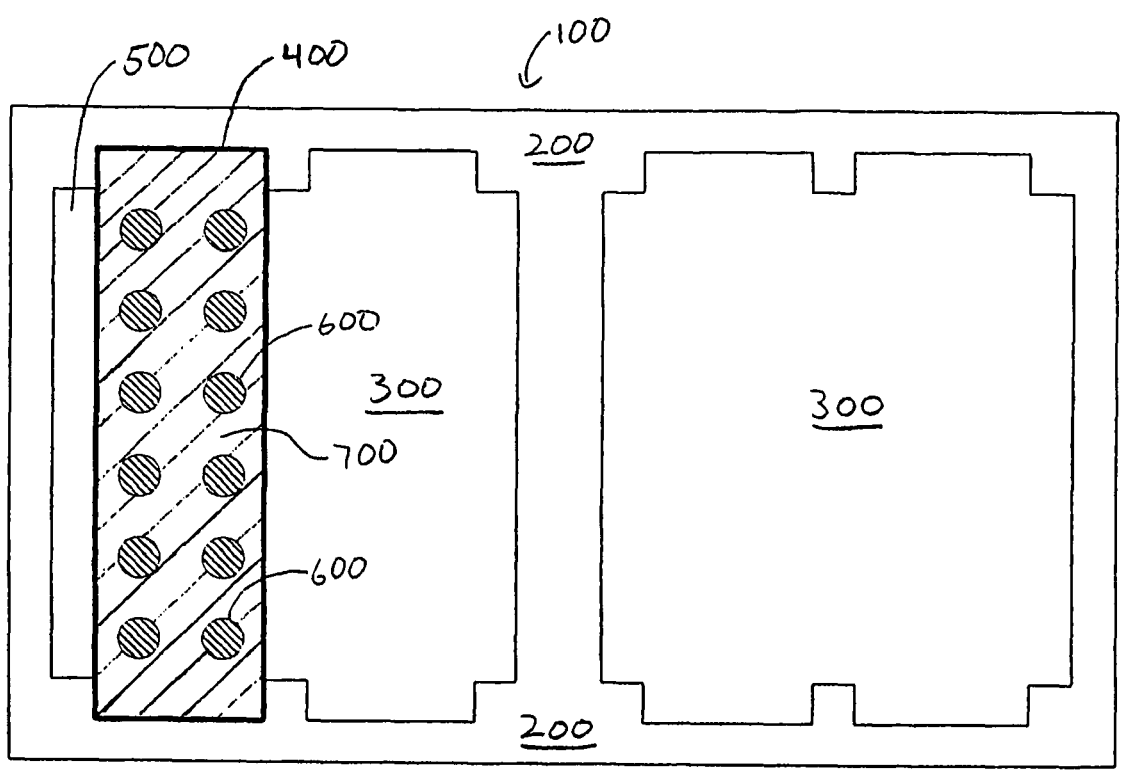
FIG. 48 is a schematic depiction of a substrate holder of the present invention.

One embodiment of an assay substrate holder (100) of the present invention is depicted in FIG. 48. The assay substrate holder (100) comprises a support surface (200). In preferred embodiments, the dimensions of the support surface (200) are substantially similar to the dimensions of a commercial multiwell plate. In other words, the footprint of the support surface (200) is substantially similar to the footprint of a commercial multiwell plate. In further preferred embodiments, the support surface (200) has at least one cutout (300) therein into which an assay substrate (400) can be inserted. In the embodiment shown, the assay substrate holder accommodates 4 assay substrates, one of which is shown inserted into the substrate holder. Preferably, the dimensions of the cutout are such that an open area (500) is provided along the side an inserted assay substrate (400) to facilitate easy insertion and removal of the assay substrate from the assay substrate holder. The assay substrate (400) shown in FIG. 48 is a printed liquid crystal assay substrate comprising a plurality of assay regions (600) that orient crystals which are defined by a coated surface (700)

It will be recognized that the substrate holder of the present invention is not limited to use with the liquid crystal devices of the present invention. Indeed, the substrate holder finds use in a variety of assay formats, including, but not limited to, colorimetric, fluorometric, and chemiluminescent assay formats. Thus, analytic zones of the substrate can be configured for use with each of these different assay formats.

4. Handheld Viewer for use with Liquid Crystal Assay Devices

In some embodiments, the present invention provides a handheld viewer for use in conjunction with the liquid crystal assay devices of the present invention. In preferred embodiments, the hand held viewer comprises an ocular loupe (e.g., an 8× or 10× loupe) with a holder that allows placement of the assay device at the focal point of the loupe. In some preferred embodiments, the slide holder further comprises a white diffusing screen that allows for uniform illumination of analytic zones on the substrate. In still further embodiments, the loupe comprises a reticule that allows the user to measure the distance of a reaction (e.g., the distance a reaction occurs along a microfluidic channel). In further preferred embodiments, the holder allows movement of the substrate under the focal point of the loupe so that different analytic zones can be viewed.

VII. Cell Assays

The following sections further describe various embodiments of the present invention. The present invention is not intended to be limited however to the following embodiments. Indeed, one skilled in the art will be readily able to apply and adapt the disclosed embodiments directed to detecting cell migration, adhesion, proliferation, and cytological features for use in applications in other fields and disciplines.

A. Cell Adhesion and Proliferation Assays

The present invention contemplates a number of embodiments useful for employing liquid crystals for determining the number of cells present on a substrate. It is contemplated that these embodiments will allow performing cell adhesion and cell proliferation assays. In preferred embodiments, the cell adhesion and cell proliferation assays are performed on nanostructured substrates or substrates onto which structure is introduced by the seeding or decoration of the surface with nano- to micro-sized particles that order the LC layers applied thereto.

While not being limited to any particular mechanism or theory, the present invention contemplates that in these assays, the area occupied by a cell is roughly equivalent to a planar surface as it would not orient a LC placed over its surface. Therefore, the number of cells present on a substrate will be proportional to the surface area covered by the cells. It is contemplated that the exact relationship between surface area occupied by a given number of cells is dependent on the cell type and line used and the culture conditions employed.

In some preferred embodiments of the present invention, the area occupied by cells attached to an ordered substrate is characterized by a non-aligned (i.e., disordered) area of the liquid crystal. The area occupied by cells is thus quantifiable using a variety of methods. In preferred embodiments, the assay device is analyzed using cross polars in conjunction with a CCD, photodiode or photomultiplier. With this system, the increased amount of light transmitted through the disordered areas can be analyzed. In further preferred embodiments, specific wavelengths of light are used in conjunction with thin films of liquid crystals to report the area occupied by cells.

In still other preferred embodiments of the invention, a liquid crystalline substrate is prepared such that the presence of a cell attached to the surface of the liquid crystalline substrate leads to a change in the optical appearance of the substrate.

Substrates suitable for the cell adhesion, quantification, proliferation and migration assays include, but are not limited to, substrates having rubbed protein surfaces, rubbed polymeric surfaces (e.g., tissue culture polystyrene), ordered polymeric substrates formed by micromolding of lithographically created masters, oblique deposition of gold films, and nano- to micro-sized particles seeded onto the surface that are ordered upon initial deposition using a nanostamper or negative nanostamper or particulate matter that is randomly seeded onto a surface and subsequently ordered by motive forces, exemplified by, but not limited to electric fields, magnetic fields and fluid flow. An additional substrate suitable for cell adhesion and proliferation assays is a liquid crystalline substrate. The liquid crystalline substrate is preferably prepared from a low molecular weight liquid crystal, a polymeric liquid crystal, a lyotropic or thermotropic liquid crystal, or a composite of liquid crystal and polymer, including biological polymers such as those that comprise the extracellular matrix.

In some particularly preferred embodiments, a biological moiety is covalently or noncovalently associated with the surface of the substrate. Suitable biological moieties include, but are not limited to, sugars, proteins (e.g., extracellular matrix proteins such as collagen, laminins, fibronectin, vitronectin, osteopontin, thromospondin, Intercellular adhesion molecule-1 (ICAM-1), ICAM-2, proteoglycans such as chondroitin sulfate, von Willebrand factor, entactin, fibrinogen, tenascin, Mucosal adressin cell adhesion molecule (MAdCAM-1), C3b, and MDC (metalloprotease/disintegrin/cysteine-rich) proteins), nucleic acids, specific receptors and cell receptor recognition sequences (e.g., cadherein, immunoglobulin superfamily, selectin, mucin and integrin binding sequences such as RGD, EILDV, LDV, LDVP, IDAP, PHSRN, SLDVP, GRGDAC, and IDSP)). In some embodiments, these biological moieties are associated with a substrate or surface that is ordered. In other embodiments, a surface or substrate with which biological moieties are associated is ordered by a method such as rubbing. It is contemplated that using rubbed protein/peptide substrate surfaces in the cell adhesion, migration, contraction and proliferation embodiments of the present invention allows researchers to investigate the impact of these constituents and to optimize assay conditions. For example, it is contemplated that the use of rubbed protein substrates will promote the adhesion of seeded cells and also promote cell function (e.g., such as adhesion, contraction, proliferation and migration). However, in some embodiments, it may be desirable to study cell function independent of the interaction of the rubbed protein substrates, thus, some embodiments employ polymeric substrates. Still other embodiments of the present invention provide substrates that combine attached protein/peptide moieties with non-biological forms of substrate functionalization and fabrication such as oblique deposition of gold and micromolded surfaces.

Some embodiments of the cell adhesion and proliferation assays of the present invention provide a plurality of distinct assay regions that allow for replicates of experimental conditions and controls to be run simultaneously. In still other preferred embodiments, the assay devices of the present invention are designed to have a footprint that is compatible with standard commercial plate readers (e.g., 24, 96, 384, 1536 etc., well plates). In still some other embodiments, simple nanostructured inserts are provided for use with commercial plates and plate readers.

Figure 52A:
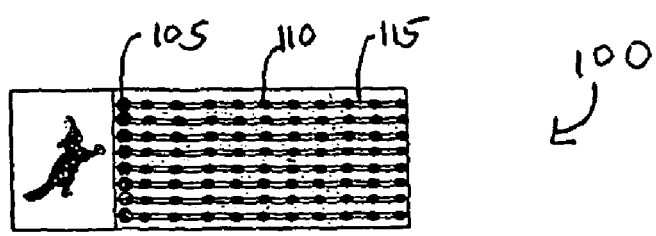
FIG. 52A is a schematic depiction of an assay device in slide format.
Figure 52B:
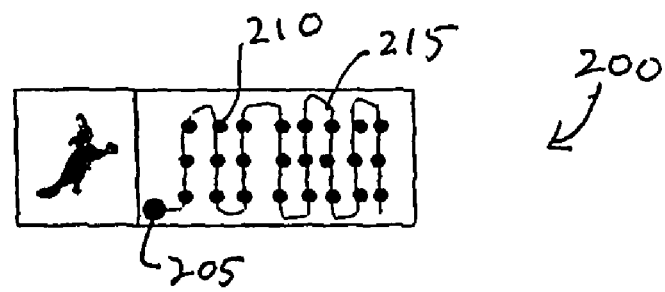
FIG. 52B is a schematic depiction of an assay device in slide format.
Figure 52C:
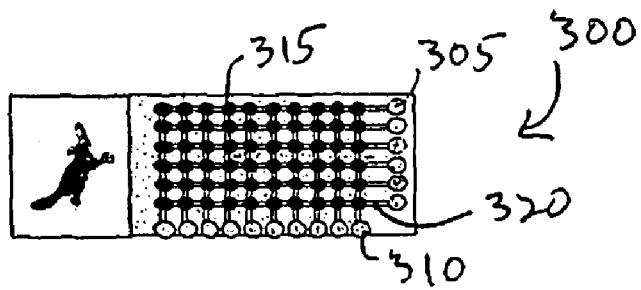
FIG. 52C is a schematic depiction of an assay device in slide format.

In still other embodiments, the assay formats of the present invention are integrated with microfluidics. Examples of such assays are provided in FIGS. 52a, b, and c. Referring to FIG. 52a, an assay device (100) in a slide format is provided. This assay device (100) comprises a plurality of reservoirs (105) that are fluidically connected with a series of discreet assay regions (110) via microchannels (115). The assay device 100 is configured so that assays may be run in parallel. Referring to FIG. 52b, another assay device (200) in a slide format is provided. This assay device (200) comprises at least one reservoir (205) that is fluidically connected to a series of assay regions (210) via a microchannel (215). It is contemplated that in this format a test compound introduced into the reservoir (205) will be present at higher concentrations in assay regions near the reservoir and lower concentrations in assay regions more remote from the reservoir (205). Referring to FIG. 52c, another assay device (300) in a slide format is provided. This assay device (300) comprises a first series of reservoirs (305) and a second series of reservoirs (310) that are fluidically connected to assay regions (315) via microchannels (320). This device (300) is therefore configured to assay the effect of gradients of two different test compounds, one test compound added in the first series of reservoirs (305) and the second test compound added to the second series of reservoirs (310).

B. Cell Migration Assays

Certain embodiments of the present invention provide assays for qualitatively and/or quantitatively determining the migration (e.g., random movement as well as attraction or repulsion) of cells on a substrate under control conditions and in response to one or more compounds of interest. In particular, the present invention contemplates, as described more fully below, a variety of assay formats optimized for distinguishing the positive, neutral or negative chemotactic and chemokinetic effects of one or more test compounds on cells of interest.

Figure 5:
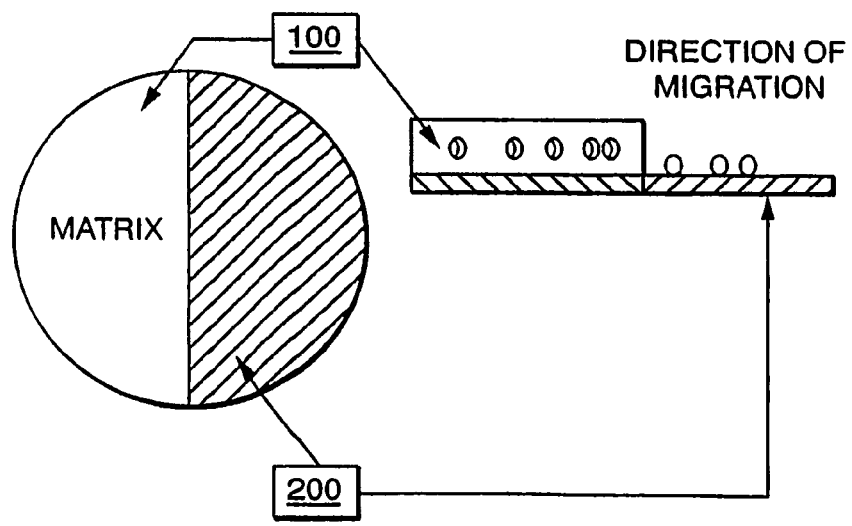
FIG. 5 is a schematic depiction of a device of the present invention that incorporates a matrix.

In some embodiments, the present invention provides cell invasion assays. It is contemplated that these assays are useful as an indication of neoplastic transformation and relative aggressiveness (invasiveness) of a tumor type. These in vitro assays are used to establish the effectiveness of therapeutic agents in preventing/minimizing invasion. Some preferred embodiments employ the use of nanostructured substrates in combination with extracellular matrices. FIG. 5 demonstrates a design whereby invasion of the matrix (100) results in a loss of cells from the adjacent nanopatterned region (200) that would report the relative number of cells present. The decrease in cell number on the patterned substrate is indicative of successful invasion of the adjacent matrix. In some embodiments, cells are first seeded and then overlayed with a suitable matrix material (e.g., Matrigel or agar).

In some preferred embodiments, the extent of invasion of the ECM by placement of the liquid crystals on the ECM is read out. The present invention is not limited to any particular mechanism of action. Indeed, an understanding of the mechanism of action is not necessary to practice the present invention. Nevertheless, the process of invasion of the cells into the ECM leads to a change in the structure of the ECM that is reflected in the orientations of liquid crystals placed on to the surface. In a still further preferred embodiment of the invention, the ECM is prepared with a slightly anisotropic structure such that it uniformly orients the LC in the absence of invasion of the ECM by cells. Changes to the structure of the ECM caused by the invaded cells, leads to a disruption of the uniform orientation of the LC. In other embodiments of the invention, the process of invasion of the cells into the ECM leads to the introduction of anisotropic structure that is reflected in an increase in the order of LC placed onto the surface.

Figure 6:
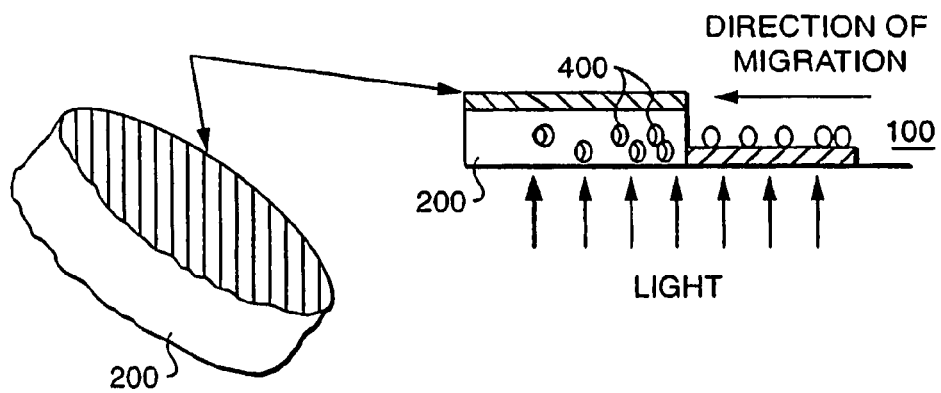
FIG. 6 is a schematic depiction of a device of the present invention that incorporates a matrix.

In still other embodiments of the present invention, extracellular matrices with nanopatterned surfaces that align liquid crystal films are provided. Referring to FIG. 6, cells are seeded onto the right hand surface only (100). Invasion of the ECM (200) (that is rubbed, stamped, molded or decorated with aligned nano- to micro-sized particles on its surface such that it aligns LC placed on its surface (300)) by cells (400) results in a change in light transmission through a LC film placed on its surface in the test areas (e.g., where cells are initially seeded and in the ECM). In FIG. 6 it can be appreciated that invasion of the ECM (200) will cause changes in the alignment of LC mesogens in both the initial seeding region (100) and in the ECM (100). Changes in the initial seeding region (100) occur due to a decrease in cells on its surface thus providing a greater surface area for aligning LC mesogens. Changes in LC mesogen orientation in the ECM (200) occur due to subtle changes in the matrix caused by cell invasion that will be translated to the nanopatterned surface and subsequently in the mesogens contained in the thin film of LC placed on its surface.

It is contemplated that this embodiment may also be employed in studies of cell biomechanics where subtle changes in surface mechanics caused by processes exemplified by, but not limited to, cell adhesion, migration and contraction are reported by alterations in LC orientation that are observable by viewing with polarized light and the appropriate use of filters and by the use of certain wavelengths of light.

In another embodiment of the invention, hybrid three-dimensional matrices composed of ordered LC and of extracellular matrix (ECM) constituents are provided that would support cell function upon or within the matrix. In preferred embodiments, the hybrid matrix is formed by gelling an admixture of constituents (singly or together) exemplified by, but not limited to, mesogens, sugars, proteins (e.g., extracellular matrix proteins such as collagen, laminin, fibronectin, vitronectin, osteopontin, thromospondin, Intercellular adhesion molecule-1 (ICAM-1), ICAM-2, proteoglycans such as chondroitin sulfate, von Willebrand factor, entactin, fibrinogen, tenascin, Mucosal adressin cell adhesion molecule (MAdCAM-1), C3b, and MDC (metalloprotease/disintegrin/cysteine-rich) proteins), nucleic acids, specific receptors or cell receptor recognition sequences (e.g., cadherein, immunoglobulin superfamily, selectin, mucin and integrin binding sequences such as RGD, EILDV, LDV, LDVP, IDAP, PHSRN, SLDVP, GRGDAC, and IDSP). In preferred embodiments, the gel process is conducted while applying an orienting electric field. This results in a matrix with aligned mesogens that are stable after gelling. It is contemplated that this gelling procedure also orients the other matrix constituents (depending on their relative charge and asymmetry of charge distribution).) The oriented hybrid composite can be prepared by using electric fields, magnetic fields, or by mechanical shearing of the composite. In some embodiments, commercially available basement membrane-like complexes (e.g., Matrigel™, which is harvested from a transformed cell line (EHS)) are used as the ECM constituent admixed with the liquid crystalline species. The liquid crystals can be thermotropic or lyotropic liquid crystals. If lyotropic liquid crystals, then preferred mesogens include non-membrane disrupting surfactants, and discotic mesogens that are not membrane disrupting.

In some preferred embodiments, cells are seeded adjacent to the matrix as illustrated in FIG. 6 or cells are seeded on the surface of the matrix and invasion of the matrix by the cells is indicated by a change in LC orientation.

In a preferred embodiment of the invention, a matrix is prepared such that it possesses an anisotropic structure. This anisotropic structure is induced by one of a number of methods that will be evident to those skilled in the art, including but not limited to mechanical shear, and the use of electric and magnetic fields. The presence of the anisotropic structure will lead to anisotropic optical properties of the matrix. These anisotropic optical properties can include birefringence and dichroism. The presence of invaded cells is detected by a change in the anisotropic optical properties of the matrix. These can be determined by using polarized light and an analyzer or monochromatic and/or polarized light.

Referring again to FIG. 7, in some embodiments cells are seeded on the right initially. The loss of cells from this surface as they invade the matrix would be evident as well as their invasion causing a change in LC orientation in the hybrid (LC-ECM) matrix on the left. This hybrid matrix could also be used in conjunction with a planar (i.e., non-orienting) or opaque substrate.

Figure 7:
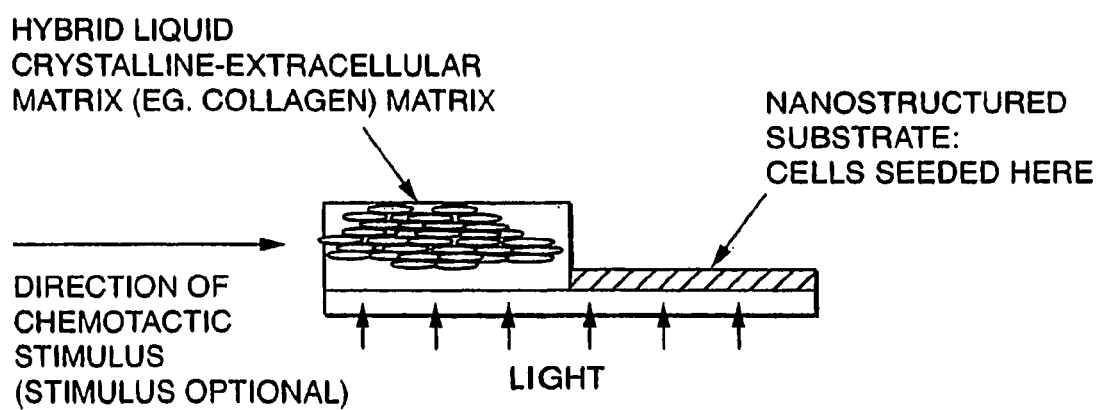
FIG. 7 is a schematic depiction of a device of the present invention that incorporates a matrix.

In the embodiment depicted in FIG. 7, the cells are seeded on the substrate on the right and a change in the hybrid matrix on the left will occur with invasion of cells that will manifest as a change in mesogen orientation embedded within the matrix. It can be seen that the region in which cells are initially seeded is a nanostructured substrate that aligns mesogens in the LC film and will therefore report the presence and relative number of cells. As the cells invade the hybrid matrix on the left a decrease in cell number on the right will be reported simultaneous with a change in the hybrid matrix caused by the cellular invasion. In some embodiments a chemotactic gradient will be supplied to the cells.

Figure 8:
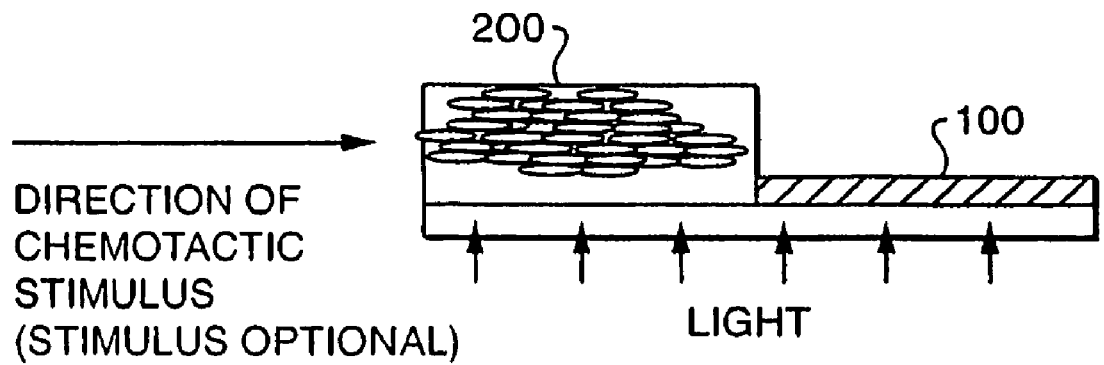
FIG. 8 is a schematic depiction of a device of the present invention that incorporates a matrix.

In other embodiments (depicted in FIG. 8) the cell seeding region comprises a substrate that is opaque to light or is simply not structured as to cause alignment of liquid crystal mesogens. In this embodiment, the presence of cells and their subsequent decrease in number on the initial seeding region (100) will not be reported but their successful invasion of the hybrid matrix will.

Figure 9:
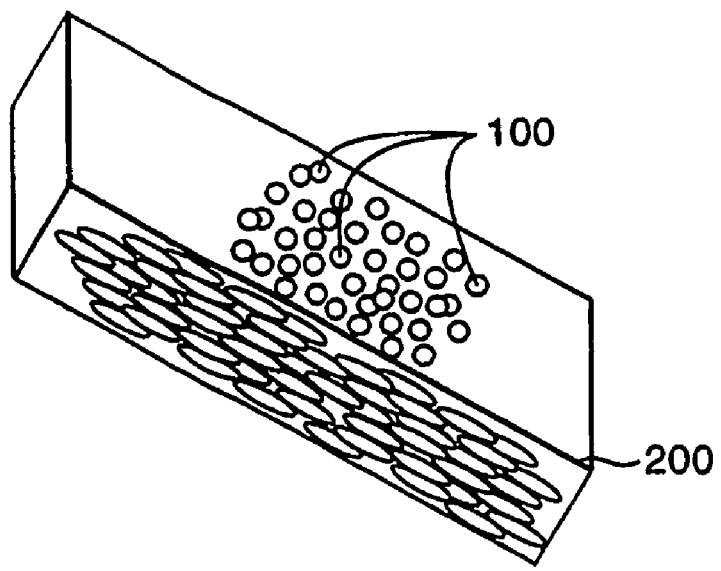
FIG. 9 is a schematic depiction of a device of the present invention that incorporates a matrix.

In some embodiments (depicted in FIG. 9), cells (100) are seeded onto the surface of the hybrid ECM-LC matrix (200) and invasion of the matrix occurs from the surface. Invasion is detected as an alteration in mesogen orientation. The versatility of this unique hybrid matrix is evident in its ability to be used in assays investigating the dynamics of cell adhesion, cell contraction and cell invasion. The present invention is not limited to any particular mechanism of action. Indeed, an understanding of the mechanism of action is not necessary to practice the present invention. Nevertheless, it is contemplated that the alignment of the mesogens is disrupted by minute forces exerted upon (cells seeded on the surface) or into (cells invading the matrix) the matrix. In preferred embodiments, the change in mesogen alignment is reported by the alteration in the passage of polarized light or other specific wavelengths or combinations of wavelengths of light. In still further preferred embodiments, the present invention provides mesogen-decorated matrices, preferably mesogen-decorated ECMs. Mesogens are attached to the matrix (e.g., ECM) by using the primary amines, carboxylic acids, and thiols that are available for reaction on the components of the matrix (e.g., ECM).

Figure 10:
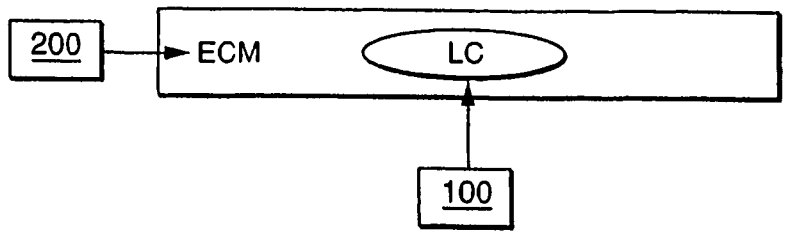
FIG. 10 is a schematic depiction of a device of the present invention that incorporates a matrix.

In other embodiments, matrices incorporating mesogens are prepared by embedding a pre-aligned LC matrix (100) within a larger extracellular matrix (ECM:200) that is allowed to gel (see, e.g., FIG. 10). The present invention is not limited to any particular mechanism of action. Indeed, an understanding of the mechanism of action is not necessary to practice the present invention. Nevertheless, it is contemplated that changes in the ECM are translated to the LC matrix. In other embodiments, the ECM is dissolved into the mesogens when they are in their isotropic state, and then the mesogens are transformed into the liquid crystalline state. The transformation of state can be achieved by change of temperature and/or the evaporation of a solvent. This procedure leads to the formation of a liquid crystal/ECM composite, which has the properties of a liquid crystal gel. Liquid crystal gels are known by those skilled in the art to be prepared by using low molecular weight and high molecular weight gelators. In some preferred embodiments, the ECM is the commercially available MATRIGEL (See, e.g., Monvoisin A. Bisson C. Si-Tayeb K. Balabaud C. Desmouliere A. Rosenbaum J.; Involvement of matrix metalloproteinase type-3 in hepatocyte growth factor-induced invasion of human hepatocellular carcinoma cells; International Journal of Cancer 97(2):157-62, 2002).

In other preferred embodiments, the hybrid mesogen/matrices comprise type I collagen and/or porcine submucosal matrix (See, e.g., Rosenthal et al., The mucosal invasion model: a novel in vitro model for evaluating the invasive behavior of mucocutaneous malignancies. Archives of Otolaryngology—Head & Neck Surgery. 127(12):1467-70, 2001. Galvez et al., Membrane type 1-matrix metalloproteinase is activated during migration of human endothelial cells and modulates endothelial motility and matrix remodeling. Journal of Biological Chemistry. 276(40):37491-500, 2001) While these matrices are the most widely used matrices for invasion assays, the present invention is not limited to their use. Indeed, the use of other matrices is contemplated, including, but not limited to, Amgel-derived from human amniotic membranes (See, e.g., Siegal et al. Development of a novel human extracellular matrix for quantitation of invasiveness of human cells. Cancer letters 69: 123-32. 1993).

It is contemplated that the hybrid LC-matrices have numerous other uses in addition to invasion assays. The LC-matrices find use in studies of cell biomechanics where subtle changes in the matrix caused by processes (e.g., cell adhesion, cell migration and cell contraction) are reported by alterations in LC orientation. In preferred embodiments, such alterations are detected by viewing the LC-matrix with filtered polarized light. Additionally, since the orientation of LC is very sensitive to temperature shifts, the LC-matrices are useful for reporting changes in metabolic activity of individual and populations of cells. In preferred embodiments, liquid crystalline substrates can also be used to report stresses imparted to substrates by cells adhered to surfaces. In this embodiment of the invention, the cells are supported on the surface of the liquid crystalline substrate. The substrates can be decorated with ECM.

Similarly, an ECM that has a patterned surface (FIG. 6) can be used to report changes induced in the surface (adjacent to the surface occupied by cells) caused by events exemplified by but not limited to adhesion, migration and contraction. These changes are then reported by a LC film placed on its surface and subsequently viewed with polarized light or specific wavelengths of light.

In still further embodiments, the substrates and hybrid matrices of the present also find use in contraction assays. The most common form of contraction assays for which the substrates and hybrid matrices are useful are gel contraction assays (See, e.g., Fireman et al., Morphological and biochemical properties of alveolar fibroblasts in interstitial lung diseases. *Lung.* 179(2):105-17, 2001; Ballas et al., Delayed wound healing in aged rats is associated with increased collagen gel remodeling and contraction by skin fibroblasts, not with differences in apoptotic or myofibroblast cell populations. *Wound Repair Regeneration.* 9(3):223-37, 2001; Roy et al., Exertion of tractional force requires the coordinated up-regulation of cell contractility and adhesion. *Cell Motility & the Cytoskeleton.* 43(1):23-34, 1999; and Lee et al., Extracellular matrix; and pulmonary hypertension: control of vascular smooth muscle cell contractility. *American Journal of Physiology.* 274(1 Pt 2):H76-82, 1998.

Single cell contraction is also sometimes evaluated by measuring cross sectional area after contraction is maximally stimulated in vitro. (See, e.g., Pang et al., Single-cell contraction assay for human ciliary muscle cells. Effect of carbachol. *Investigative Ophthalmology & Visual Science.* 34(5):1876-9, 1993. Another assay describes the forces exerted by individual cells calculated from time-lapse videomicroscopic recordings of the 2-D elastic distortion of the matrix. See, e.g., Roy et al. An in vitro force measurement assay to study the early mechanical interaction between corneal fibroblasts and collagen matrix. *Experimental Cell Research.* 232(1): 106-17, 1997.

The present invention also provides methods and compositions for reporting biomechanical transduction events in cells of interest. For example, in certain embodiments, suitable liquid crystal membranes are used to nonspecifically report biomechanical transduction events associated with cell adhesion, migration and contraction. While not being limited to any particular mechanism or theory, the present invention contemplates that in these embodiments, the detectable event is the change in the order of the crystalline membrane itself. A number of non-limiting embodiments of contemplated cell transduction assays are presented in the following examples. In one example, a film of liquid crystal is associated with a phospholipid which is subsequently spontaneously adsorbed by the cell of interest. In another example, an elastomeric liquid crystalline material is used and contacted to the cells of interest. In yet another example, a polymer-stabilized or polymer-dispersed liquid crystal is used and contacted to the cells of interest. In another example, a liquid crystalline gel is used and contacted with the cells of interest. In still another example, a collagen gel that has been micromolded such that it aligns liquid crystals is used and contacted to the cells of interest. In this embodiment, the cells of interest are allowed to attach to a collagen gel and then incubated for a period of time which is dictated by experimental design, cell type and culture conditions. Changes in stress imparted by cell contraction create detectable changes in the liquid crystal layers. Yet other embodiments described below utilize a novel hybrid extracellular matrix-liquid crystalline composite for the reporting of biomechanical transduction events.

Figure 11:
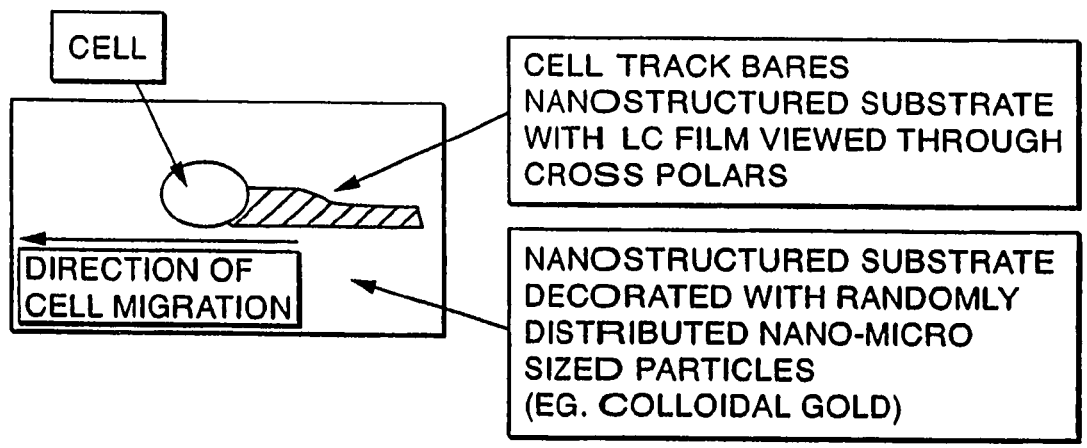
FIG. 11 is a schematic depiction of a device of the present invention that incorporates particles on a substrate.
Figure 12:
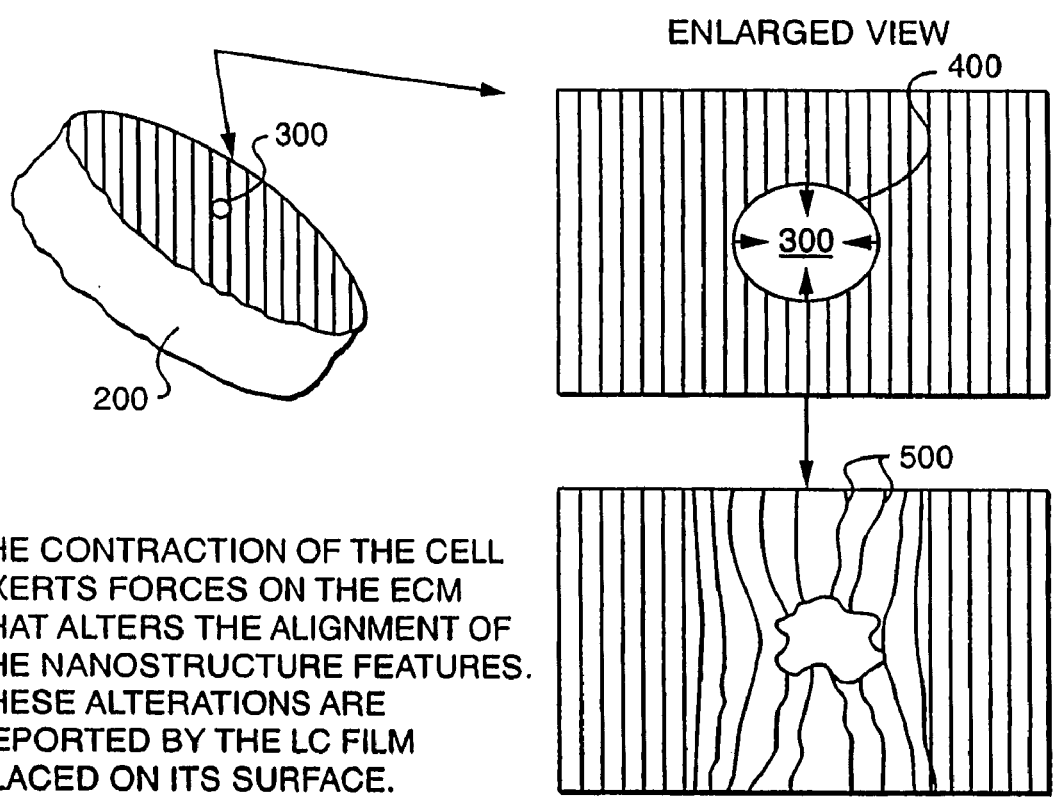
FIG. 12 is a schematic depiction of a device of the present invention that incorporates a matrix.

FIG. 11 demonstrates an embodiment of the invention that allows the evaluation of contractile forces by large populations of cells as well as by individual cells. Cells (300) are seeded on a nanostructured surface (100) of extracellular matrix (200) that aligns liquid crystal mesogens placed on its surface. The contraction of a cell (400) results in altering the regular array of the nanostructured surface (500) which in turn is reported by alterations in the alignment of LC mesogens. Cells may be imaged simultaneously as interpretation of LC alignment changes by staining the cells with vital or non-vital dyes (fluorometric and non-fluorometric). Dual exposure (with and without polarized light) allows localization of individual cells and correlating their location and appearance with observed changes in LC alignment.

Additionally, the use of these matrix-LC interactions and hybrid matrices allows for examining the forces of individual cells seeded onto their surfaces, which provides insight into the dynamics of cell adhesion, migration and contraction.

The present invention contemplates that cells migrating across a substrate produce nanomechanical forces that either disorder an ordered surface or order a disordered surface. In both cases, the change in surface order created by the passage of cells is detected and reported by liquid crystal films. Migrating cells also sweep ordered surface particles out of their path during migrations and introduce disorder in the LC film placed on top subsequent to migration. Another variation is the use of a nanostructured substrate with randomly distributed (seeded) and randomly oriented (relative to the long axis) nano- to micro-sized particles across its surface. This creates closely spaced regions that introduce disorder into the LC film effectively partially masking the ordering influence of the underlying nanostructured substrate. The seeding densities are such that many particles are present on the surface relative to the size of a single cell. The migration of cells unmasks the underlying nanostructured substrate and creates tracks of purely ordered mesogens. The particles can be any nano- to micro-sized inert material including but not limited to colloidal gold, other metals, pumice, graphite, silica, and glass beads. It is contemplated that the particles decorating the surface can be made more resistant to displacement during the flow of LC over the surface (i.e., to prevent the particles from being washed off) by the adjunctive use of stabilizing forces exemplified by, but not limited to, the use of externally applied electric fields (with charged particles), magnetic fields (with magnetic particles), or chemical and physical treatment of the surfaces of the particles to make them adherent to the substrates The assay devices of the present invention are designed to detect these changes in order or disorder. Accordingly, in some embodiments, a substrate is provided that has at least one assay region that either orients or does not orient a liquid crystal. In some preferred embodiments, the assay region is associated with one or more biological moieties as described in more detail below. However, the assay regions need not be necessarily associated with a biological moiety. In further preferred embodiments, the assay regions are arranged in an array. In some particularly preferred embodiments, the array is aligned with readout zones of a plate reading device. In some embodiments of the present invention, the assay devices are further provided with a number of topological features. For example, in some embodiments, an assay region of the device has a depression or well formed in the substrate for containing cells, media, or test compounds.

In other preferred embodiments the assay devices further comprise a test compound region or plurality of test compound regions separate from the assay regions. These regions are useful for providing one or more test compounds for use in the assays and causing delivery of the one or more test compounds to the assay regions. In some embodiments, the test compound regions are peripherally located on the assay device as compared to the assay regions, while in other embodiments, the test compound regions are centrally located as compared to the assay regions, while in still further embodiments, the test compound regions are interspersed with the assay regions. Various combinations of these layouts are also contemplated by the present invention.

In some embodiments, the test compound regions are arranged to provide a gradient (e.g., a concentration gradient) of at least one test compound to the assay region. The gradients for two or more test compounds can be in the same direction or in different directions. In other embodiments, the test compound regions are arranged to deliver a relatively constant amount of at least one test compound to assay region(s). In some particularly preferred embodiments, the test compound regions are designed to provide an analysis of whether a cellular response to a particular test compound placed in a reservoir is chemotactic or chemokinetic in nature. In some preferred embodiments, the test compound regions are channels, microchannels, or wells formed in the substrate.

In other preferred embodiments, the test compound regions are in the form a porous or nonporous material that releases a given test compound into the assay device. Suitable test compounds but are not limited to, small organic compounds, amino acids, vitamins and peptides and polypeptides, including, but not limited to, magainin (e.g., magainin I, magainin II, xenopsin, xenopsin precursor fragment, caerulein precursor fragment), magainin I and II analogs (PGLa, magainin A, magainin G, pexiganin, Z-12, pexigainin acetate, D35, MSI-78A, MG0 [K10E, K11E, F12W-magainin 2], MG2+ [K10E, F12W-magainin-2], MG4+ [F12W-magainin 2], MG6+ [f12W, E19Q-magainin 2 amide], MSI-238, reversed magainin II analogs [e.g., 53D, 87-ISM, and A87-ISM], Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME (1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 [(±) 1-(4-aminobutyl)-6-benzylindane], PM2c [(±)-6-benzyl-1-(3-carboxypropyl)indane], PM3 [(±)1-benzyl-6-(4-aminobutyl)indane], tachyplesin, buforin I or II, misgurin, melittin, PR-39, PR-26, 9-phenyl-nonylamine, (KLAKKLA)n, (KLAKLAK)n, where n=1, 2, or 3, (KALKALK)3, KLGKKLG)n, and KAAKKAA)n, wherein N=1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG1, 1bAMP, snakin, lipid transfer proteins, Insulin, Insulin like Growth Factors such as IGF-I, IGF-II, and IGF-BP; Epidermal Growth Factors such as α-EGF and β-EGF; EGF-like molecules such as Keratinocyte-derived growth factor (which is identical to KAF, KDGF, and amphiregulin) and vaccinia virus growth factor (VVGF); Fibroblast Growth Factors such as FGF-1 (Basic FGF Protein), FGF-2 (Acidic FGF Protein), FGF-3 (Int-2), FGF-4 (Hst-1), FGF-5, FGF-6, and FGF-7 (identical to KGF); FGF-Related Growth Factors such as Endothelial Cell Growth Factors (e.g., ECGF-α and ECGF-β); FGF- and ECGF-Related Growth Factors such as Endothelial cell stimulating angiogenesis factor and Tumor angiogenesis factor, Retina-Derived Growth Factor (RDGF), Vascular endothelium growth factor (VEGF), Brain-Derived Growth Factor (BDGF A- and -B), Astroglial Growth Factors (AGF 1 and 2), Omentum-derived factor (ODF), Fibroblast-Stimulating factor (FSF), and Embryonal Carcinoma-Derived Growth Factor; Neurotrophic Growth Factors such as α-NGF, β-NGF, γ-NGF, Brain-Derived Neurotrophic Factor (BDNF), Neurotrophin-3, Neurotrophin-4, and Ciliary Nuerotrophic Factor (CNTF); Glial Growth Factors such as GGF-I, GGF-II, GGF-III, Glia Maturation Factor (GMF), and Glial-Derived Nuerotrophic Factor (GDNF); Organ-Specific Growth Factors such as Liver Growth Factors (e.g., Hepatopoietin A, Hepatopoietin B, and Hepatocyte Growth Factors (HCGF or HGF), Prostate Growth Factors (e.g., Prostate-Derived Growth Factors [PGF] and Bone Marrow-Derived Prostate Growth Factor), Mammary Growth Factors (e.g., Mammary-Derived Growth Factor 1 [MDGF-1] and Mammary Tumor-Derived Factor [MTGF]), and Heart Growth Factors (e.g., Nonmyocyte-Derived Growth Factor [NMDGF]); Cell-Specific Growth Factors such as Melanocyte Growth Factors (e.g., Melanocyte-Stimulating Hormone [α-, β-, and γ-MSH] and Melanoma Growth-Stimulating Activity [MGSA]), Angiogenic Factors (e.g., Angiogenin, Angiotropin, Platelet-Derived ECGF, VEGF, and Pleiotrophin), Transforming Growth Factors (e.g., TGF-α, TGF-β, and TGF-like Growth Factors such as TGF-$\beta_2$, TGF-$\beta_3$, TGF-e, GDF-1, CDGF and Tumor-Derived TGF-β-like Factors), ND-TGF, and Human epithelial transforming factor [h-TGFe]); Regulatory Peptides with Growth Factor-like Properties such as Bombesin and Bombesin-like peptides (e.g., Ranatensin, and Litorin), Angiotensin, Endothelin, Atrial Natriuretic Factor, Vasoactive Intestinal Peptide, and Bradykinin; Cytokines such as the interleukins IL-1 (e.g., Osteoclast-activating factor [OAF], Lymphocyte-activating factor [LAF], Hepatocyte-stimulating factor [HSF], Fibroblast-activating factor [FAF], B-cell-activating factor [BAF], Tumor inhibitory factor 2 [TIF-2], Keratinocyte-derived T-cell growth factor [KD-TCGF]), IL-2 (T-cell growth factor [TCGF], T-cell mitogenic factor [TCMF]), IL-3 (e.g., Hematopoietin, Multipotential colony-stimulating factor [multi-CSF], Multilineage colony-stimulating activity [multi-CSA], Mast cell growth factor [MCGF], Erythroid burst-promoting activity [BPA-E], IL-4 (e.g., B-cell growth factor I [BCGF-I], B-cell stimulatory factor 1 [BSF-1]), IL-5 (e.g., B-cell growth factor II [BCGF-II], Eosinophil colony-stimulating factor [Eo-CSF], Immunoglobulin A-enhancing factor [IgA-EF], T-cell replacing factor [TCRF]), IL-6 (B-cell stimulatory factor 2 [BSF-2], B-cell hybridoma growth factor [BCHGF], Interferon $\beta_2$ [IFN-B], T-cell activating factor [TAF], IL-7 (e.g., Lymphopoietin 1 [LP-1], Pre-B-cell growth factor [pre-BCGF]), IL-8 Monocyte-derived neutrophil chemotactic factor [MDNCF], Granulocyte chemotatic factor [GCF], Neutrophil-activating peptide 1 [NAP-1], Leukocyte adhesion inhibitor [LAI], T-lymphocyte chemotactic factor [TLCF]), IL-9 (e.g., T-cell growth factor III [TCGF-III], Factor P40, MegaKaryoblast growth factor (MKBGF), Mast cell growth enhancing activity [MEA or MCGEA]), IL-10 (e.g., Cytokine synthesis inhibitory factor [CSIF]), IL-11 (e.g., Stromal cell-derived cytokine [SCDC]), IL-12 (e.g., Natural killer cell stimulating factor [NKCSF or NKSF], Cytotoxic lymphocyte maturation factor [CLMF]), TNF-α (Cachectin), TNF-β (Lymphotoxin), LIF (Differentiation-inducing factor [DIF], Differentiation-inducing activity [DIA], D factor, Human interleukin for DA cells [HILDA], Hepatocyte stimulating factor III [HSF-III], Cholinergic neuronal differentiation factor [CNDF], CSF-1 (Macrophage colony-stimulating factor [M-CSF]), CSF-2 (Granulocyte-macrophage colony-stimulating factor [GM-CSF]), CSF-3 (Granulocyte colony-stimulating factor [G-CSF]), and erythropoietin; Platelet-derived growth factors (e.g., PDGF-A, PDGF-B, PDGF-AB, p28-sis, and p26-cis), and Bone Morphogenetic protein (BMP), neuropeptides (e.g., Substance P, calcitonin gene-regulated peptide, and neuropeptide Y), and neurotransmitters (e.g., norepinephrine and acetylcholine).

Accordingly, in some embodiments, the present invention provides an assay apparatus comprising a surface having at least one discreet assay region thereon and wherein the assay region is associated with at least one test compound formulated for controlled release. In some embodiments, the test compound formulated for controlled release is provided in a matrix. In some embodiments, the matrix is a polymer. Various polymers that find use for controlled release applications, include, but are not limited to chitosan, chitosan-alginate, poly(N-isopropylacrylamide) hydrogels, lipid microspheres, copolymers of polylactic and polyglycolic acid, dextran hydrogels, and poly(ethylene glycol) hydrogels. (See, e.g., Zambito et al., Acta Technol. Et Legis Medicamenti 14(1):1-11 (2003); Bhopaktar et al., Advances Chitin Sci. 5:166-170 (2002); Zhuo et al., J. Polymer Sci. 41(1):152-159 (2002); Del Curto et al., Proceedings of the 28th Symposium on Controlled Release of Bioactive Materials, San Diego, Calif., 2:976-977 (2001); Hu et al., J. Drug Targeting 9(6):431-438 (2001); Lambert et al., J. Controlled Release 33(1):189-195 (1995); Hennink et al., J. Controlled Release 48(2,3):107-114 (1997); and Zhoa et al., J. Pharm. Sci. 87(11):1450-1458 (1998). In some embodiments, the matrix further comprises an extracellular matrix component (e.g., collagen, vitronectin, fibrionectin or laminin. A variety of test compounds may be provided in the matrix, including, but not limited to, polypeptides, carbohydrates, amino acids, and small organic compounds. These assay devices may be used with any of the read out and labeling methods described herein, including LC based assays, colorimetric assays, fluorimetric assays, optical density assays, and light scattering assays. In other embodiments, the assay devices are configured with a plurality assay regions corresponding spatially to the wells of 6, 12, 24, 36, 96, 384 or 1536 well plates. The matrix containing the test compound may be provided in a variety of orientations, for example on the bottom of a well or other assay region, on the side of a well, as a strip in the bottom or side of well or other assay region, or as a bead on an interior surface of a well or on an assay region.

In still further embodiments, the present invention provides kits comprising an assay apparatus comprising a surface having thereon at least one discreet assay region and unpolymerized matrix material. In some embodiments, the discreet assay region further comprises a cell seeding region. In some embodiments, the kits provide instructions for polymerizing the matrix material in the presence of at least one test compound, applying the matrix to an apparatus, and culturing cells in the apparatus. It is contemplated that foredoing apparatuses find use in assaying the response of cells to a stimulus from a test compound. The apparatuses may also be utilized in high-throughput settings to measure the effect of a panel or library of compounds on cells.

In still further embodiments, test compound regions are provided by the differential movement of materials (e.g., test compounds) by the manipulation of electrical fields, thermal gradients, and capillary action on the substrate surface. In other preferred embodiments of the invention, chemotactic or chemokinetic agents are immobilized on the surfaces. These agents can be presented in uniform concentration on a surface, they can be patterned on a surface or they can be present in a gradient in concentration across a surface. The agents immobilized on the surface may be released from the surface to make them available to the cells by using changes in the microenvironment of the surfaces caused by the cells to trigger the release of the agents, or externally controlled variables (such as illumination or applied electrical potentials) can be used to regulate the release of the agents from the surface. In other preferred embodiments of the invention, the agents are not released from the surface but interact with constituents of the membrane of the cell and thereby influence cell behavior.

In some further preferred embodiments, the assay regions of the devices are associated with a biological moiety. In some embodiments, a disordered (e.g., randomly ordered) substrate or assay region on a substrate appropriate for assays disclosed herein is created by attaching (e.g., covalently or noncovalently) one or more biologic moieties, (e.g., sugars, proteins (e.g., extracellular matrix proteins such as collagen, laminin, fibronectin, vitronectin, osteopontin, thromospondin, Intercellular adhesion molecule-1 (ICAM-1), ICAM-2, proteoglycans such as chondroitin sulfate, von Willebrand factor, entactin, fibrinogen, tenascin, Mucosal adressin cell adhesion molecule (MAdCAM-1), C3b, and MDC (metalloprotease/disintegrin/cysteine-rich) proteins), nucleic acids, specific receptors or cell receptor recognition sequences (e.g., cadherein, immunoglobulin superfamily, selectin, mucin and integrin binding sequences such as RGD, EILDV, LDV, LDVP, IDAP, PHSRN, SLDVP, GRGDAC, and IDSP)) onto a suitable substrate surface. In another embodiment, an ordered substrate or assay region on a substrate is created by covalently or noncovalently binding one or more or the previously described biological moieties to a polymeric surface and subsequently rubbing the surface to create order. The present invention is not intended to be limited by the order of steps taken in creating a suitable substrate surface. For example, in some embodiments, the substrate is ordered prior to the attachment of biological moieties. In other embodiments, the substrate is ordered after addition of biological moieties. Indeed, a number of processing events and steps are adaptable to producing suitable substrate compositions for use in the assays disclosed herein given the specific guidance provided and the skill of those in the art.

Figure 1B:
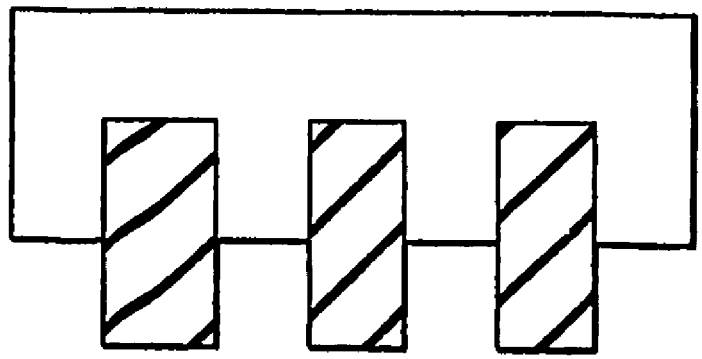
FIG. 1B is a schematic depiction of a negative nanostamper for use in the present invention.

In other embodiments, an ordered substrate is created by contacting a suitable surface with a plurality of evenly distributed particles (e.g., magnetic nanoparticles) that when aligned orient a mesogenic layer. As described in detail above, the particles may be applied to the surface (positive nanostamp) or removed from the surface (negative nanostamp) with nanostamping devices (ref. FIGS. 1A and 1B). In particularly preferred embodiments, the particles are magnetic nanoparticles that are aligned using a magnetic field. In another preferred embodiment, the metallic nanorods are small enough to be readily displaced by migrating cells.

In some embodiments of the present invention, the extent of overall cell movement in the assay device is determined by analyzing the proportion of the substrate on which surface order is altered (e.g., a change from ordered to disordered and vice versa). Preferred methods for analyzing the extent of areas of order and disorder are described in detail above and include the use of systems comprising two polarizers, CCDs, photomultipliers, photodiodes, plate reading devices, and analysis of the transmission of certain wavelengths of light. Other methods for analyzing the results of the assays are described below.

Figure 13:
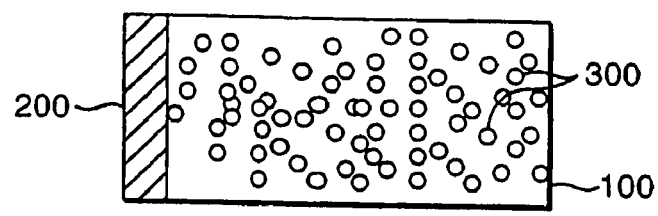
FIG. 13 is a depiction of a cell assay device of the present invention.

A number of particularly preferred assay devices and systems will now be described. It will be understood that the present invention is not limited to these particular embodiments. One embodiment of the present invention to distinguish chemotactic/chemokinetic effects is illustrated in the model assay depicted in FIG. 13. Element (100) represents a suitable substrate (either ordered or disordered). A test compound reservoir (200) is provided on the left edge of substrate (100). In some embodiments, reservoir (200) and substrate (100) are engineered so that the test compound is slowly transported or diffused across the substrate (100) and the assay region to contact cells (300) on the surface of the substrate. It is contemplated that convection can be minimized by using very thin films of liquid, by making the culture medium viscous through the addition of polymers, or by placing the whole system into a gel that quenches convection but permits movement of the cells. In other embodiments, these elements are engineered so that the test compound is more quickly dispersed into the media covering cells (300) via capillary action. In performance of the assay, cells of interest (300) are seeded onto the assay region on substrate (100). In one embodiment, the effects of a test compound on cell motility can be determined as follows. The test compound is placed in reservoir (200) and cells (300) are again seeded in the assay region or randomly distributed across the entire substrate.

Figure 14:
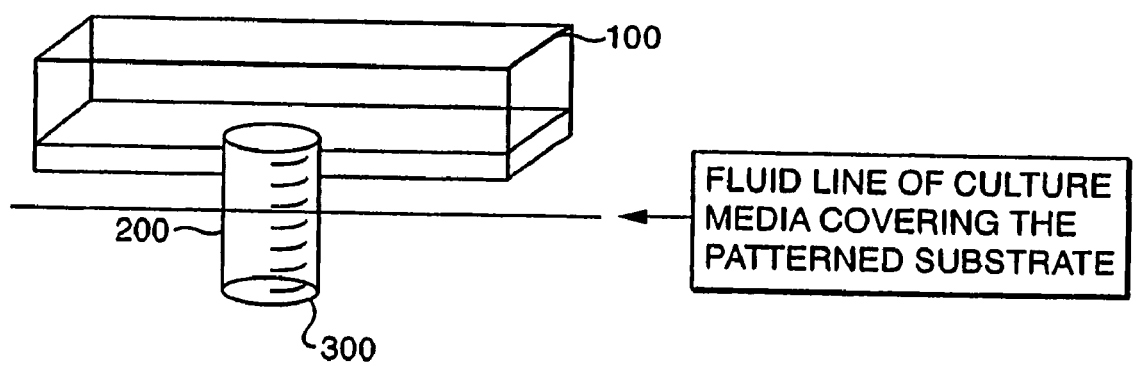
FIG. 14 is a schematic depiction of a cell culture device of the present invention.

In some embodiments, a specifically designed reservoir is utilized to provide a gradient of test compound(s) delivered through diffusion. FIG. 14 demonstrates one possible design whereby a test compound(s) is placed into a reservoir (100) and is allowed to diffuse along a thin tube (200) and exit from a small open port (300) in close proximity to the test substrate. The actual dimensions of the device are variable depending on the needs of the specific assay and the test surface area (and accompanying volume of media covering it) to which test compound is being delivered. The composition of the reservoir and the delivery tube can be of a variety of materials including but not limited to glass, polypropylene, polystyrene, and silicone.

The reservoir device may be incorporated into the intrinsic design of an assay device or may be provided as an insert for use with commercially available or custom designed multi-well plates. It will be recognized that this assay design is not limited to use with liquid crystal assays, but also finds use with calorimetric, fluorometric, densitometric, and other assay formats.

If the test compound is chemotactic, the cell pathways are substantially linear with the net migration being towards the reservoir port (300 in FIG. 14). Movement of cells within the assay region 300 creates areas of disorder (on an ordered substrate) or introduces order by mechanical movement of cells across the surface of a randomly ordered substrate that can be assayed as described above. In particularly preferred embodiments, image analysis software is used to determine the relative linearity of migration paths.

Is it also possible to formulate these test compounds into a "slow release tablet" that is placed at some location of the test surface. The gradual dissolution of the tablet generates a locally high concentration of the text compound. Some slow release tablets are placed under external control; for example; rates of dissolution are controlled by illumination of electrical potentials.

It will also be recognized that the device does not necessarily need to comprise the reservoir (200). As a non-limiting example of an assay not requiring the reservoir (200) the substrate (100) is prepared by seeding cells (300) in the assay region and providing the test compound in the accompanying cell media. A compound that increases cellular activity will have a positive effect on cell motility as compared to control compounds. In preferred embodiments, the assay region is ordered to orient liquid crystals. Movement of cells (300) within the assay region creates areas of disorder that can be assayed as described above. In some embodiments, the analysis of separate assays involving addition of a test compound to the test compound region or generally into the media can be used to differentiate the chemotactic and/or chemokinetic effects of the test compound.

Figure 15:
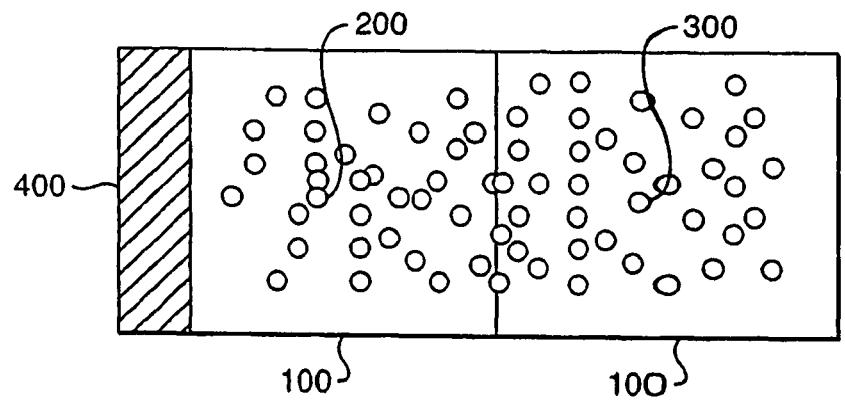
FIG. 15 is a schematic depiction of an assay device of the present invention.

FIG. 15 shows yet another assay system for studying the effects of a test compound on cell motility and migration. The substrate (100) comprises a first region 200 and a second region 300 having distinct surface order. In some embodiments, the first region (200) is ordered to orient liquid crystals while the second region (300) does not orient liquid crystals. In a preferred embodiment, substrate (100) also comprises a test compound reservoir (400).

One contemplated protocol using the assay system shown in FIG. 15 is as follows. The user seeds cells in a uniform fashion onto the first and second regions (200 and 300). A test compound is introduced to substrate (100) in the media accompanying the seeded cells, provided via the test compound region (400). Quantification of cell migration can be performed by measuring the number of cells present in the first region (200) by measuring the number of cells in the second region (300) or by comparing the cell numbers present in the first region (200) and second region (300). If the test compound is chemokinetic, there should not be a marked change (increase or decrease) in the number of cells in the first region (200) or in the second region (300). However, if the test compound is chemotactic there will be a marked increase in the number of cells in the first region (200) and a decrease in the cells present in the second region (300). If a compound has a negative effect on chemotaxis then there will be an increase in cell number in the second region (300) with a concomitant decrease in cell number in the first region (200).

Figure 16:
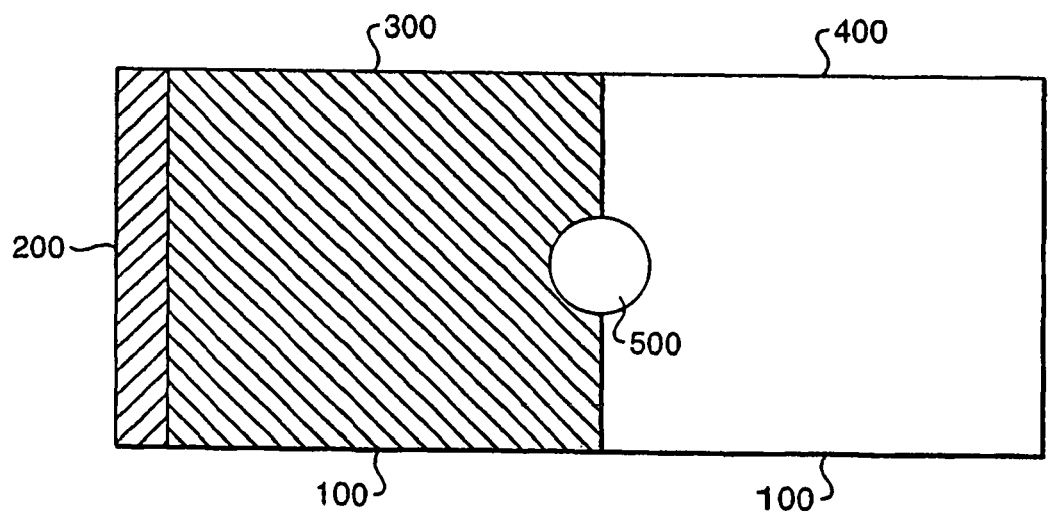
FIG. 16 is a schematic depiction of an assay device of the present invention.

In still another embodiment, as shown in FIG. 16, a substrate (100) is provided having a reservoir (200) and two separate regions (300 and 400) of distinct surface order. Accordingly, in certain embodiments, substrate (100) further provides a first region (300) of ordered substrate that aligns liquid crystals, and a second region (400) of substrate that does not align liquid crystals. In further embodiments, a cell seeding region (500) (exemplified by but not limited to a depression or well) is provided for seeding cells of interest on substrate (100). In some embodiments of the present invention, methods are provided wherein cells are seeded at the cell seeding region (500) on two separate substrates. Each group of seeded cells is allowed to attach and grow for a sufficient period of time (determined by cell type and culture conditions) usually from 1-24 hr. The media is then replaced on each substrate, and sufficient fresh media is added to cover each substrate. The test compound is then placed either in the media covering the substrate in a first instance, or in the reservoir (200) in a second instance. The cells on both substrates are allowed to incubate for a sufficient period of time (according to the cell type and culture conditions) in the presence of the test compound. The number of cells on the first region (300) is then determined. The present invention contemplates that by comparing results obtained from substrates having test compound added to the media and substrates having test compound added only to the reservoir (300), a determination can be made as to whether the test compound is chemotactic or chemokinetic. Chemokinetic activity will result in a net increase in cell number in both regions 300 and 400 region while chemotaxis will cause a marked increase (greater than in the case of chemokinesis) in cell number in the region closest to the reservoir release point of the test compound (300) and a negative chemotactic effect will cause an increase in cell number in the test region further away from the reservoir source (400) with a concomitant decrease in the patterned region that aligns liquid crystals (300). In preferred embodiments, appropriate controls of media only and media plus fetal bovine serum (FBS) are also run.

Figure 17:
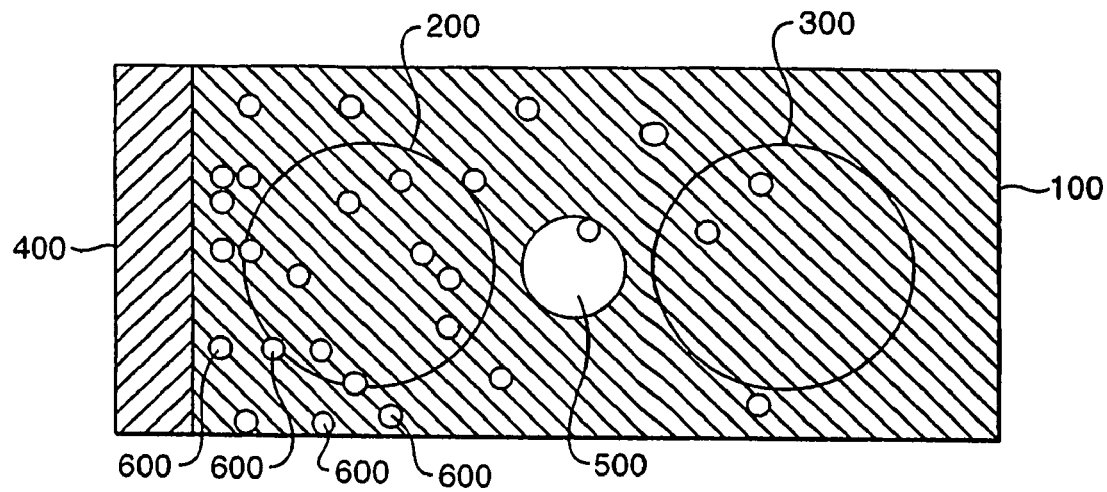
FIG. 17 is a schematic depiction of an assay device of the present invention.
Figure 18:
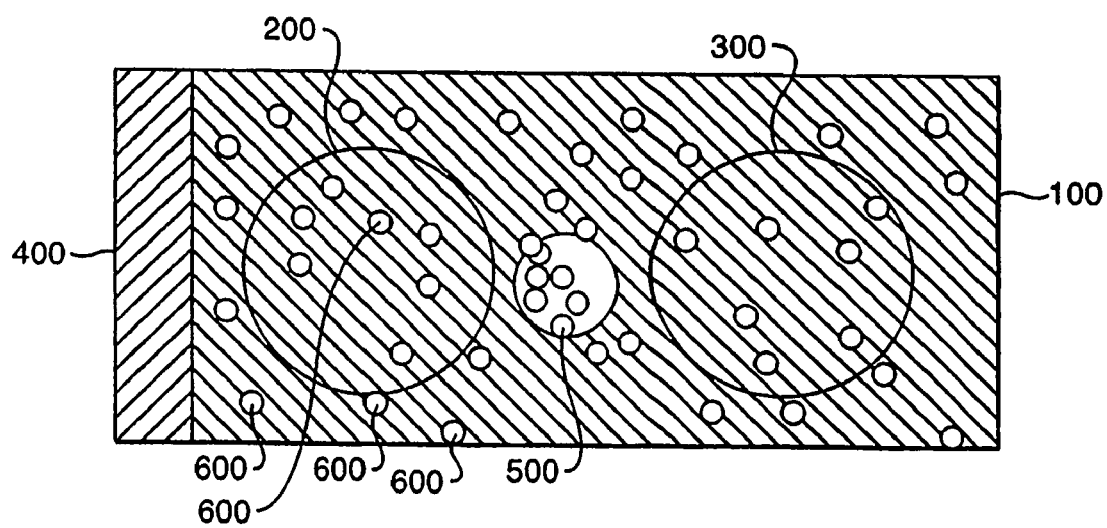
FIG. 18 is a schematic depiction of an assay device of the present invention.
Figure 19:
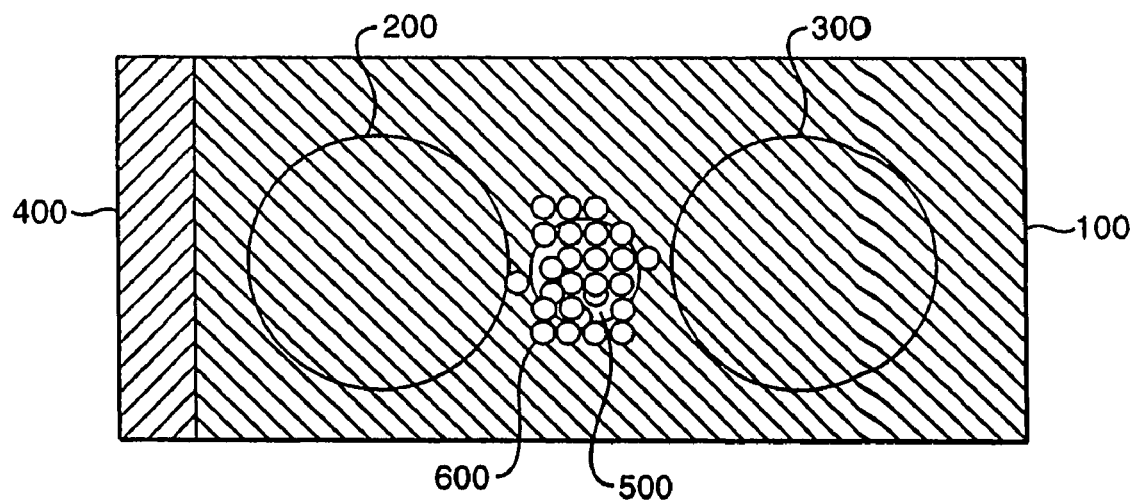
FIG. 19 is a schematic depiction of an assay device of the present invention.

In still further embodiments, the substrate described in FIG. 16 is modified so that the entire substrate (100) is configured to orient liquid crystal (See FIGS. 17, 18, and 19). In these embodiments, cells are seeded on the cell seeding region (500) and a test compound added to the reservoir (400). A test compound is chemotactic if the cells (600) are stimulated to move out of the cell seeding region and show a preferred orientation in migration towards the gradient of the stimulus. (See, FIG. 17). This effect can be determined by determining the cell number present in the first test region (200) and/or the second test region (300). The test regions do not have any differing physical characteristics. They are simply the zones used for data acquisition and may be configured to correspond to regions read out by commercially available plate readers.

A test compound is chemokinetic if the ratio of cells in the first region (100) to those in the second region (200) is close to 1, thus indicating the cells moved out of the cell seeding area but showed no preferred orientation in migration despite the gradient of the stimulus. (See, FIG. 18). A test compound that fails to induce any, or only a very few, cells to enter either Field A (200) or Field B (300) has little or no affect on cellular migration. (See, FIG. 19).

If a cell seeding region (500) is not incorporated into the design then cells uniformly distributed across the first (200) and second (300) test regions will not show a significant difference in cell number in the case of a compound that is purely chemokinetic (that is, does not promote proliferation). The use of such a design (i.e., cells evenly distributed rather than limited to a specific cell seeding region) would allow the determination of positive and negative chemotaxis but would not distinguish between no effect and positive chemokinesis.

Figure 20A:
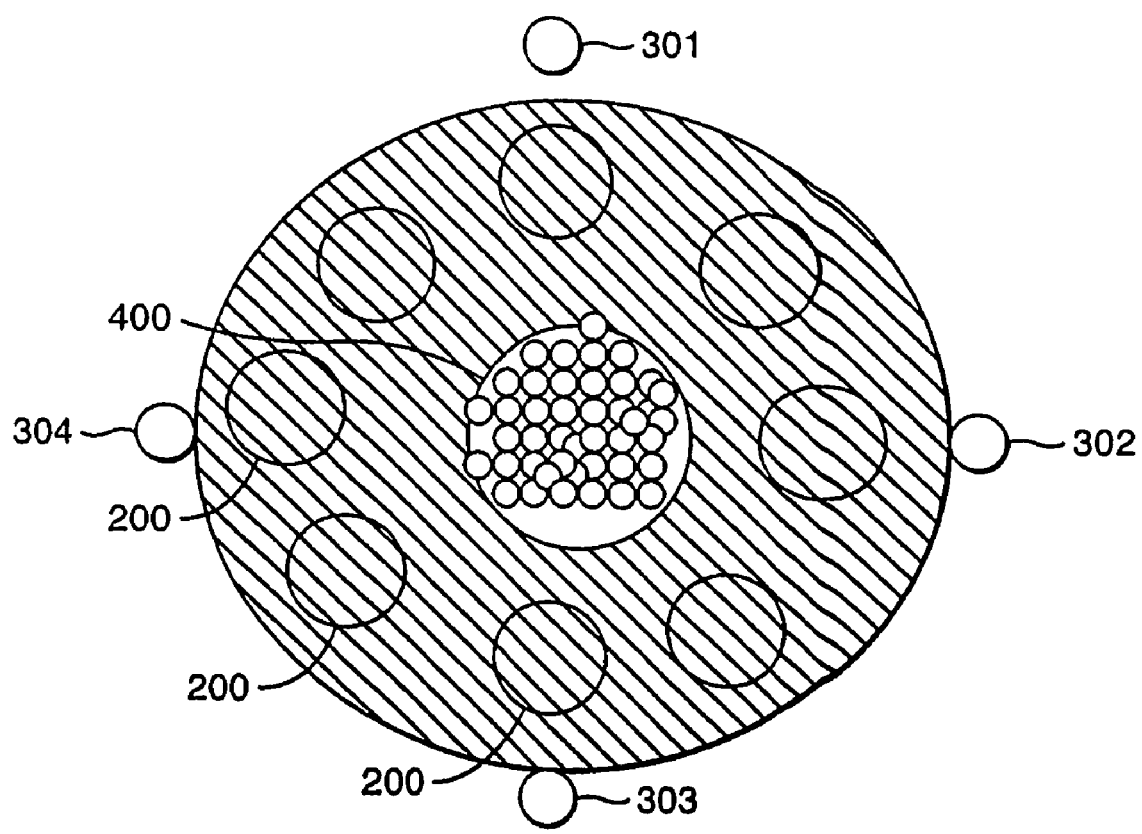
FIG. 20A is a schematic depiction of an assay device of the present invention in use.
Figure 20B:
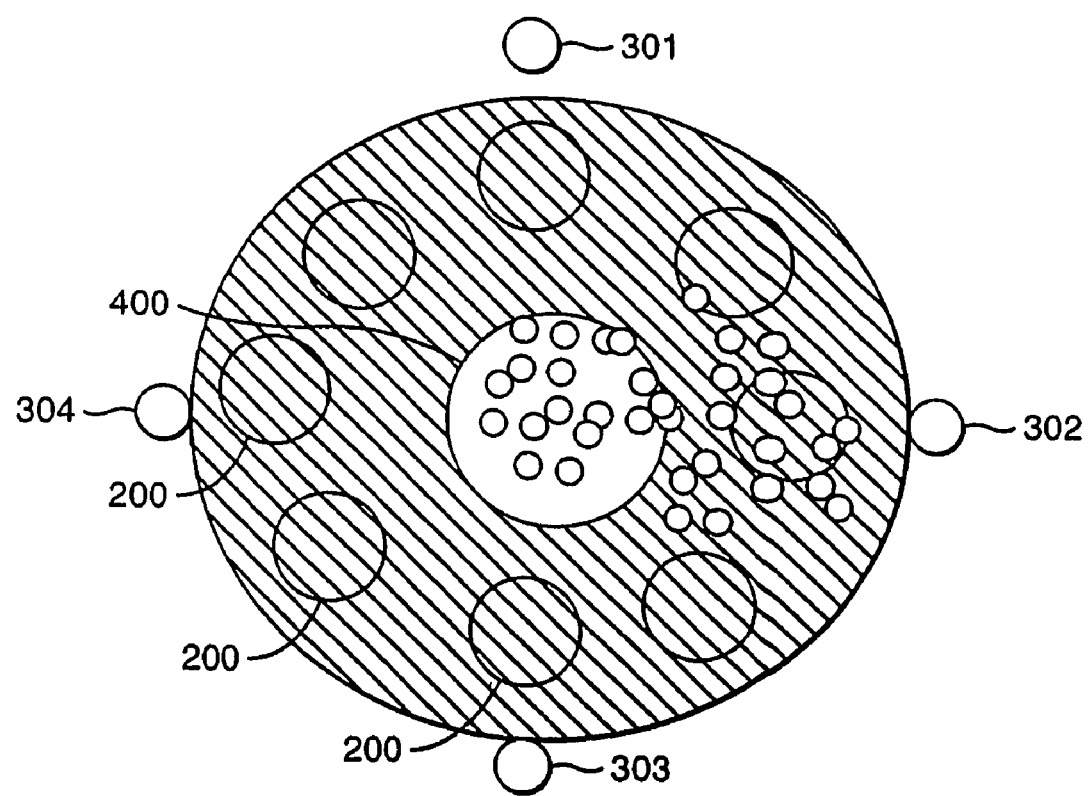
FIG. 20B is a schematic depiction of an assay device of the present invention in use.
Figure 20C:
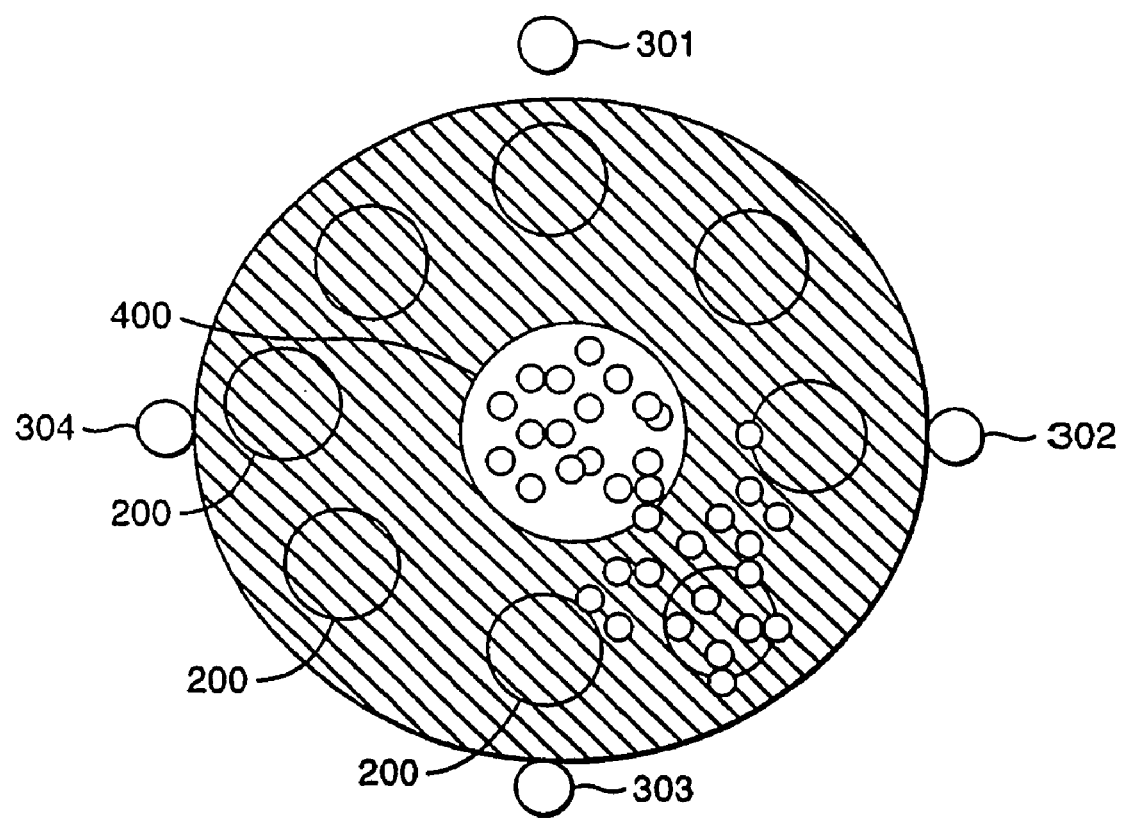
FIG. 20C is a schematic depiction of an assay device of the present invention in use.

In still other embodiments, the present invention provides assay materials and methods for determining the interactions of multiple test compounds on cell motility and migration. FIGS. 20A-C shows one contemplated assay configuration for determining the effects and potential interactions of three test compounds on cell migration. Briefly, FIGS. 20A-C provide a suitable substrate (100) having a plurality of assay regions (200) each providing a localized region of ordered substrate. In the embodiment depicted in FIGS. 20A-C, a plurality of assay regions (200) are arranged in a concentric circle around the perimeter of substrate (100), the present invention is not intended to be limited however to this configuration. A number of alternative arrangements are contemplated where the effects of the multiple test compounds can be determined (e.g., rows and columns of assay regions arrayed on substrate (100), or bands of assay regions radiating from a center point on substrate (100), etc.). In other embodiments, two or more types (e.g., local regions of ordered substrate, and/or local regions of disordered substrate) of assay regions are provided on a substrate. In a preferred embodiment, each of the assay regions (200) represent a zone of structured substrate surface that allows for the alignment of liquid crystals except where cells are located. In preferred embodiments, the various test compounds are provided on substrate (100) in test compound positions (301-304) as indicted in FIGS. 20A-C. In certain of these embodiments, each of positions (301-304) is a separate reservoir. The present invention is not intended to be limited however by the number or arrangement of positions (301-304) as currently shown in FIGS. 20A-C. Indeed, in some embodiments, greater or fewer than four positions are provided, and/or the arrangement of the positions on substrate (100) is altered (e.g., rows and, or positions radiating from a center point on substrate (100), etc.). In the example provide in FIGS. 20A-C, position 301 is contacted with test compound A, position (302) is contacted with test compound B, position (303) is again contacted with test compound A, and position (304) is contacted with test compound C. In the embodiment depicted in FIGS. 20A-C, substrate (100) also provides a cell seeding region (e.g., a depression) (400) for seeding cells. Additional embodiments provide for alternative arrangements of one or more positions for seeding cells (400). Additionally, it is possible to uniformly seed cells across the test substrate (100) encompassing all test regions (200). After incubation, (time dependent on cell type, cell line and culture conditions) positive chemotactic effects will be manifested by accumulation of cells in proximity to factors (positions 301-304) having a positive effect.

One contemplated cell migration assay protocol using the substrate shown in FIG. 20A is described below. Briefly, the cells are seeded at position (400) and allowed to attach for a suitable period of time (depending on cell type and culture conditions) usually from 1-24 hrs. After this attachment period, cell media containing test compounds are placed at positions (301-304). An additional incubation period (determined by cell type and culture conditions) is provided to allow for the seeded cells to be contacted by the test compounds. The number of cells present in each of the assay regions (200) is determined by using the methods and compositions described herein. For example, if a test compound acted alone and failed to display synergism with other compounds, then the greatest number of cells would be present in the assay region (200) directly aligned with the position (301-304) where that compound was respectively contacted to the substrate (100). If a positive interaction occurs between test compound A (positions 301 and 303) and either of test compounds B (position 302) or C (position 304) then the greatest number of cells would be located at positions intermediate between the respective positions (301-304) where these test compounds were contacted to substrate (100). FIG. 20B demonstrates a positive chemotactic effect for the test compound located at position 302 (Compound B) that is manifested by an increased number of cells being located in the test region (200) in closest proximity to test compound reservoir position 302. FIG. 20C demonstrates the anticipated results from a synergistic interaction on cell migration being observed between two different test compound (Factor A positions 301 and 303 and Factor B position 302).

In other embodiments, substrates are engineered to provide from one or more assay zones. In some of these embodiments, a single substrate is fabricated to provide multiple distinct assay zones to allow for running replicate determinations with multiple controls. In preferred embodiments, each of these assay zones is configured to correspond to the substrates depicted in FIGS. 11-20 (e.g., to comprise a plurality of the substrate formats described above). In particularly preferred embodiments, these substrates are configured for use with commercially available plate readers (e.g., assay substrates are engineered to provide distinct zones that spatially correspond to test positions recognized by commercial plate readers [e.g., 24, 96, 384, 1536 well plate formats]). In further preferred embodiments, assay substrates are provided that are configured to be inserted into wells of commercial plates and plate readers.

Figure 21:
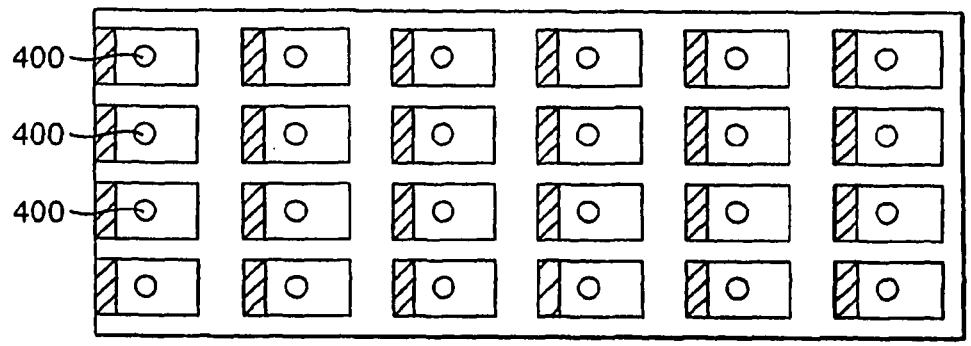
FIG. 21 is a schematic depiction of an assay device of the present invention.

FIG. 21 shows one embodiment where the disclosed assay substrates are engineered for compatibility with commercially available 24 well plate readers. FIG. 21 represents a substrate comprising a standard 6×4 arrangement of 24 individual assay surfaces.

Figure 22:
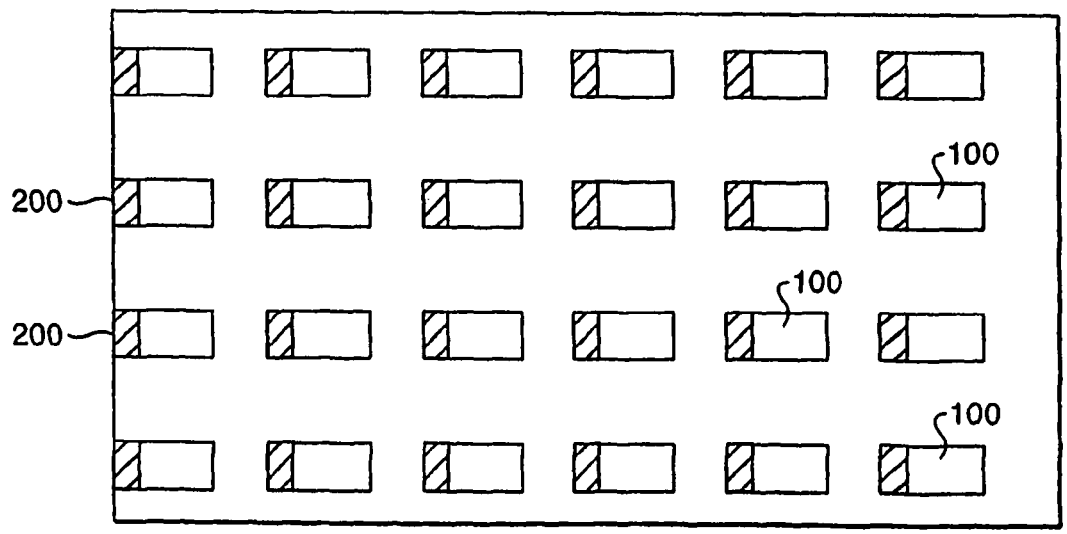
FIG. 22 is a schematic depiction of an assay device of the present invention.

Briefly, in each of the 24 assay surfaces represented, an assay region (100) and a reservoir (200) for contacting a various test compounds of interest. In preferred particularly embodiments, the plate configuration depicted in FIG. 21 utilizes a reservoir system, described in greater detail herein, that allows for differentiating chemotactic and chemokinetic cell migration. In yet another embodiment, FIG. 22 shows an adaptation of the assay plate configuration shown in FIG. 21, wherein each of the individual assay zones further provides a cell seeding region (400) (e.g., depression) for seeding cells.

Figure 23:
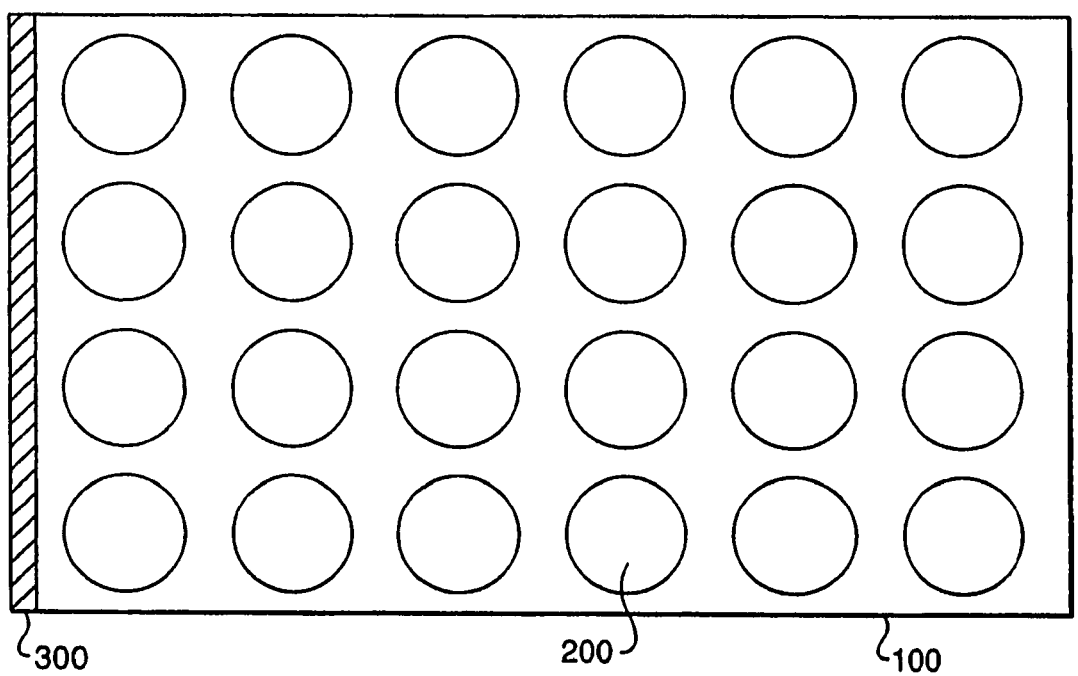
FIG. 23 is a schematic depiction of an assay device of the present invention.

Additional embodiments provide assay substrates designed to be read by commercially available plate readers (e.g., 24, 96, 384, 1536 well formats) that employ a single substrate surface and single reservoir. For example, FIG. 23 shows one contemplated embodiment where a single substrate surface (100) is engineered to provide an array of from between 24 to 1536 assay regions (200). In some of these embodiments, the substrate (100) is further configured to provide one or more test compound reservoirs (300).

In some embodiments, the substrates shown in FIG. 23 are utilized by seeding cells evenly across the across a first and a second substrate. The user then allows the seeded cells a sufficient amount of time (depending on cell type and culture media), usually from 1-24 hours, to attach to the respective substrates. The first substrate is contacted with a test compound added to the cell media. The second substrate is contacted with a test compound added to the reservoir (300). The respective substrates are then incubated for an appropriate period of time (depending on the cell line and culture conditions) to allow the test compounds to act on the seeded cells. At the end of the incubation period, the media covering the cells is removed and a thin film of liquid crystal is placed on the surface of the substrate with attached cells. The number of cells in each of the assay regions of the respective substrates is then determined by visual inspection or by using an automated plate reader. If a compound is chemotactic, then the assay regions (200) closer to the reservoir (300) would have increased number of cells and the assay regions (200) further from the reservoir (300) would have decreased number of cells when compared to control substrates (100) and compared to assays in which the test factor(s) have been added to the media covering the cells.

Figure 24:
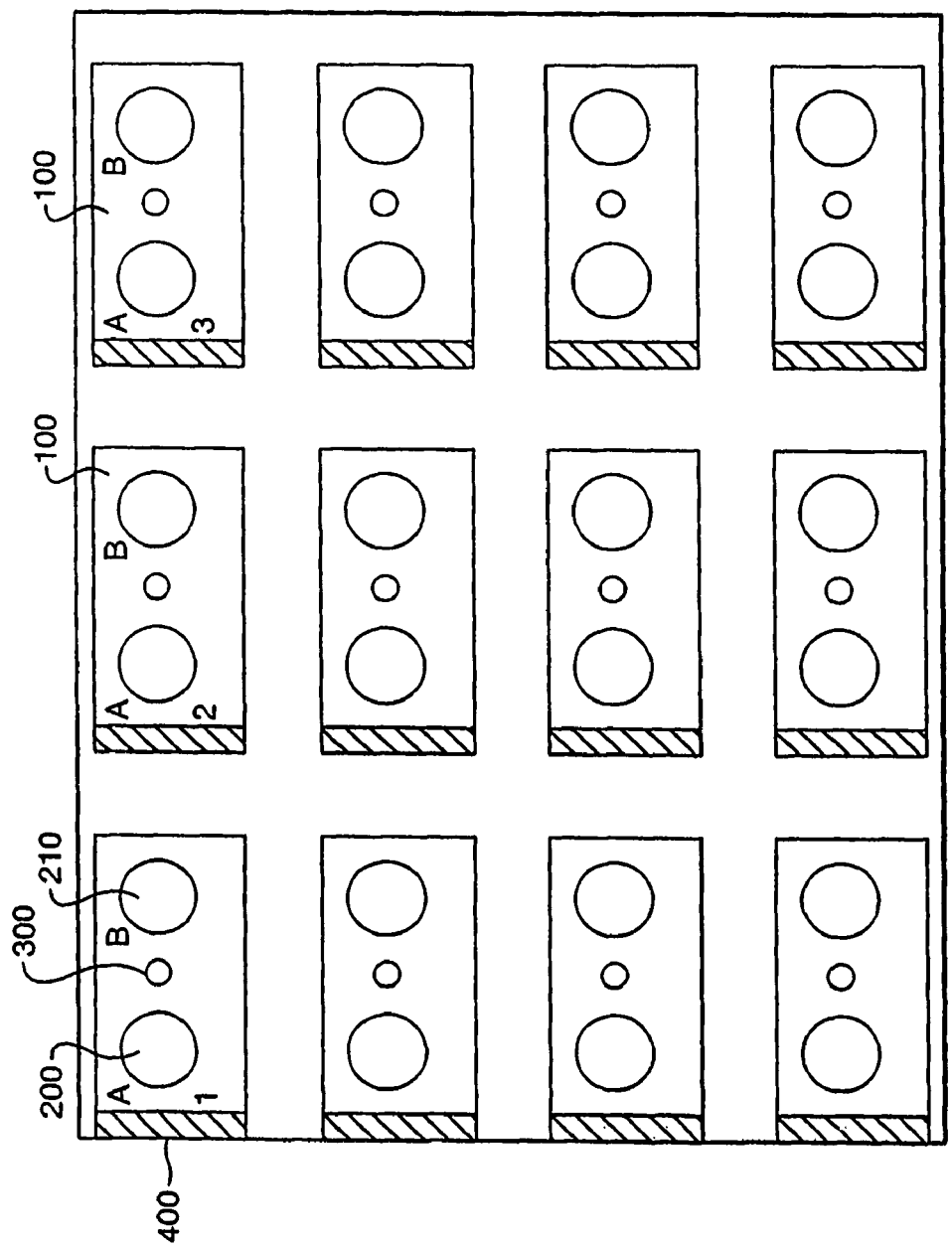
FIG. 24 is a schematic depiction of an assay device of the present invention.

In still another embodiment, the present invention provides assay materials for determining the effect on cell migration of multiple test compounds on a single substrate. In preferred embodiments, these substrates are engineered to have size and shape (e.g., 24, 96, 384, 1536, well format) compatible with commercially available plate readers. FIG. 24 shows one contemplated multiple test compound assay substrate. The assay substrate (100) shown in FIG. 21, provides 24 distinct assay regions (200). In the format depicted in FIG. 24, the assay system allows for the testing of up to 12 different compounds of interest at a time. The present invention is not intended to be limited however to a 24 well format. Indeed, other embodiments of the present invention provide from 96, 384, and 1536 well formats, these formats are easily adaptable to commercial plate readers and would provide, respectively, for the simultaneous testing of from 48, 192, to 768 compounds of interest. Briefly, FIG. 24 represents a multiple assay region formatted assay plate, wherein each of the 12 test zones (100) comprises two suitable assay regions (200 and 210), an optional cell seeding region (300) (e.g., a depression) for seeding cells, and a reservoir (400) for contacting a test compound of interest to the substrate (100). In certain embodiments, the assay regions (200) provide a localized area of ordered substrate that can anchor liquid crystals. In other embodiments, the entire plate is engineered to provide a suitable assay substrate (e.g., the entire surface can anchor liquid crystals. In some embodiments, the assay regions (200 and 210) are discreet zones, while in other embodiments, the assay regions (200 and 210) are simply the area that will be read by the plate reader. A test zone can comprise one, two, or more areas that are read by a plate reader. In FIG. 24, the test zone (100) comprises two regions (200 and 210) that are read by a plate reader. The present invention contemplates that the configuration shown in FIG. 24 is particularly well suited for differentiating the effects on cellular migration of multiple test compounds (e.g., chemotaxis versus chemokinesis).

FIG. 24 depicts use of a 24 well format that allows the running of 12 distinct assays on a single plate. This design allows for separation of chemotaxis from chemokinesis. In FIG. 24 it can be seen that cells can be seeded in region 300 and allowed to attach. Test compound or appropriate control media is placed into the designated reservoir regions (400). If a compound is chemokinetic, there will be a stimulation of cell migration but no directional preference will be evidenced by the cells and both regions 200 and 210 will evidence higher cell numbers compared to appropriate controls. If a test compound is chemotactic the increase in cell numbers will be greatest in the readout region closest to the reservoir (200) surpassing that found in the region further away from the reservoir (210).

In some embodiments, the substrate shown in FIG. 24 is utilized by evenly seeding cells in each region (that in FIG. 24 are illustrated as being restricted to the cell seeding positions) (300) across the assay plate (100) The uniformly distributed cells are allowed a sufficient amount of time (depending on cell type and culture conditions) to attach to the substrate (100). Test compound or appropriate control media is then added to reservoirs (400). After an appropriate incubation time (e.g., determined by cell type and culture conditions) the plate is read. In operation, a test compound is added to the reservoirs in the wells. If zone A (position 200) consistently indicates a greater number of cells than zone B (position 210), then a chemotactic effect of the test compound is indicated. It will be recognized that these plate formats find use with other biophotonic detection techniques, including fluorimetric, calorimetric, and densitometric techniques.

Figure 25:
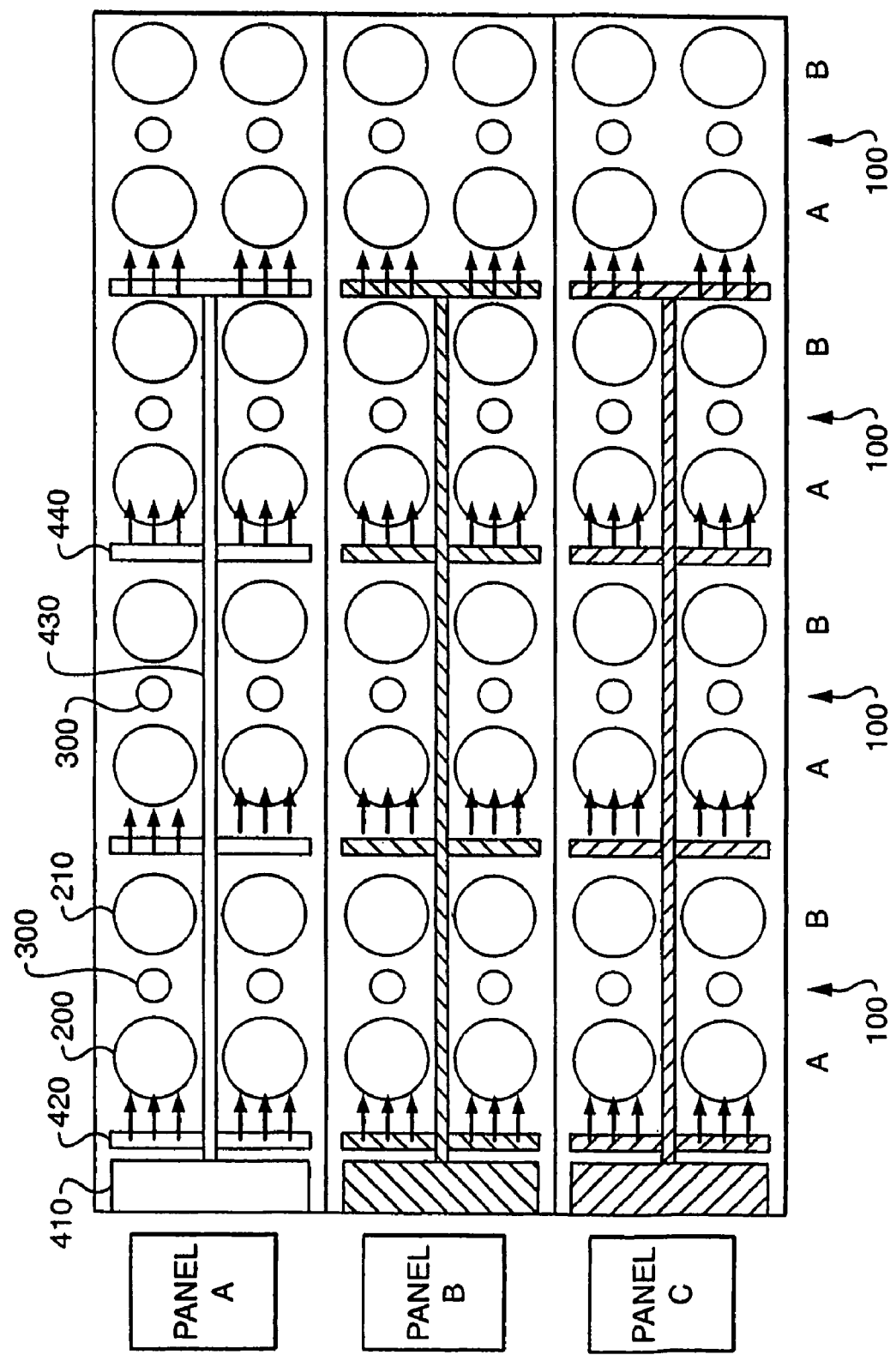
FIG. 25 is a schematic depiction of an assay device of the present invention.

In still other embodiments of the present invention, the substrates are engineered to include two or more microfluidic channels for producing uniform gradients of one or more test compounds over a plurality of assay regions. For example, FIG. 25, shows one contemplated embodiment of present invention that employs three microfluidic channels that allow for the simultaneous testing of three different compounds of interest on a single assay plate with a plurality of assay regions for each compound. Briefly, FIG. 25 shows a 48 well assay plate which has been divided into top, middle, and bottom panels, A, B, and C respectively. Each of panels A, B, and C presents 8 individual cell motility and migration test regions on a single assay plate. Thus, in preferred embodiments, the effects of each of three test compounds on cellular motility and migration can be probed in octuplicate. The present invention is not intended to be limited however to the assay configuration presented in FIG. 25. Indeed, the present invention contemplates embodiments of multiples of other commercially recognized well formats. For example, the present invention specifically contemplates embodiments using a 96 well assay plate format. Such an assay format would allow for the simultaneous testing of 8 test compounds in dodecatuplicate, or 12 test compounds in octotuplicate, etc. In regard to panel A of FIG. 25, each test region (100) comprises, two suitably ordered assay regions (200 and 210) and a cell seeding region (e.g., a depression) for seeding cells (300), and a network of reservoirs and microfluidic channels (400) configured to deliver a test compound to the test regions. The network (400) comprises a main reservoir (410) in fluidic contact with a plurality of test zone reservoirs (e.g. 420 and 440) via communicating microfluidic channels (e.g. 430). In some embodiments, the assay regions (200 and 210) are discreet zones, while in other embodiments, the assay regions (200 and 210) are simply the areas that will be read by the plate reader. A test region can comprise one, two, or more areas that are read by a plate reader. Referring to FIG. 25, the assay regions (200) are aligned in vertical columns A and B for each replicate (100) shown. In preferred embodiments, a reservoir and microfluidic channel (400) horizontally bisect each panel and form the left edge of each replicate. It can also be appreciated that the flexibility of this design allows for the testing of a single compound or of multiple compounds simultaneously if admixed in the initial reservoir (410) or supplied in different reservoirs in separate plate designs (e.g., see FIG. 26).

One contemplated cell migration and motility assay using the assay plate and shown in FIG. 25 is described below. Briefly, cells are seeded into each cell seeding region (300) for panels A, B, and C. The cells are allowed a sufficient period of time (depending upon the cell type and the culture conditions) to attach to respective positions (300). A different (or identical) test compound is added to each of the main reservoirs (410) in panels A, B, and C, respectively, so that the test compound is delivered via the network to each test region reservoir (e.g., 420 and 440). The respective test compounds are allowed a sufficient period of time (depending upon cell type and culture conditions) to act on the cells in each test region. Each test region is analyzed (e.g., using a suitably modified commercial plate reader and appropriate software or visually with a microscope) to determine ("read") the number of cells in each replicate that migrated into assay zones aligned in columns A and B, respectively. In preferred embodiments, the "reading" step is performed by overlaying the substrate with liquid crystals as described in detail above. In some embodiments this plate design and principles are used in conjunction with colorimetric and fluorimetric plate readers using standard staining protocols for imaging of cells or of indirect indicators of cell viability such as intrinsic enzyme activity.

Figure 26:
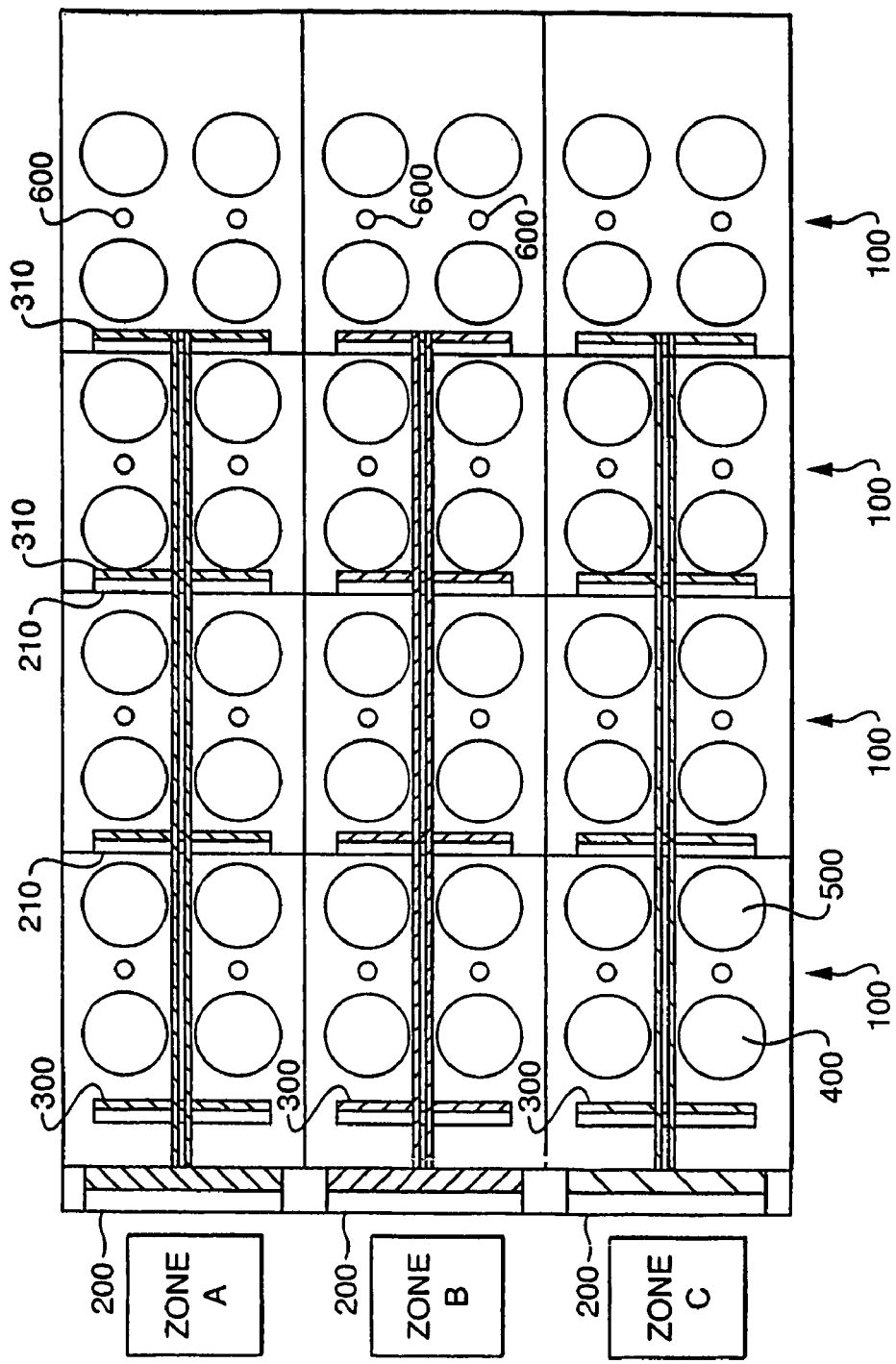
FIG. 26 is a schematic depiction of an assay device of the present invention.

In still other embodiments of the present invention, assays are provided for determining inhibitory, additive, or synergistic effects of test compounds on cellular motility and migration. For example, in regard to the preferred embodiment shown in FIG. 26, a suitably ordered assay plate (100) is configured with an array of assay regions (400 and 500) arranged to be compatible with standard commercial plate readers, and two or more separate reservoirs (200 and 300). Referring to FIG. 26, it can be seen that this embodiment is designed to provide 3 distinct test zones labeled zone A, zone B and zone C. In use, a first compound known to be chemotactic for a particular cell type is placed in one of the reservoirs (200) and a second test compound is added to the other of the reservoirs (300). This plate design allows the evaluation of two test compounds and comparison to control media Cells are seeded on the substrate in optional cell seeding areas (600) and allowed to attach as described in the embodiments above. Test compound A is placed in test reservoir (300) in zone A, test compound B is placed in test reservoir (300) in zone B and control media is placed in test reservoir (300) in zone C. Communicating microfluidic channels provide the known chemotactic agent (210) and test compound (310) to local test region reservoirs that deliver these agents to the cells on the test substrate in a gradient. Presence of cells in the assay regions (400 and 500) is preferably assayed by overlaying the substrate with liquid crystals as described above. A simple determination of the effects of the test compound can be made by comparing the results with control assays. The known chemotactic agent will stimulate cells to move into the assay region closest to the local reservoirs containing this compound (210). If a test compound (in zones A and B, deposited into reservoir 300 and delivered to local reservoirs 310) is able to inhibit chemotaxis incited by a known chemotactic agent then fewer cells will be localized to the test region closest to the test reservoirs (500) compared to controls (in zone C). Additionally, if a test agent is synergistic or additive in stimulating chemotaxis then more cells will be located in zone 500 compared to controls. If a compound completely inhibits migration of cells in the presence of a known chemotactic agent then fewer cells will be located in both assay regions 500 and 600 compared to controls. In certain embodiments it is anticipated that this design will be used in conjunction with colorimetric and fluorimetric assays. In preferred embodiments the detection of cell number will employ placing a thin film of liquid crystal overt the test substrate (with assay zones that align liquid crystal mesogens) and any attached cells. As previously described, the presence of cells will mask the nanostructured substrate locally thus prevent the LC from gaining access to the ordering influence of the substrate. In preferred embodiments, this is detected and quantified using polarized light, specific wavelengths or combinations of wavelengths of light.

Additional embodiments use this design of multiple reservoirs and microfluidic channels to create separate test zones for use in cell invasion assays described previously (See, e.g., FIGS. 5-9). This allows for the determination of the ability of a test compound to prevent cell invasion, which is often used as an indication of probable therapeutic efficacy in the development of anti-neoplastic compounds.

Additional embodiments and variations of the disclosed assay configurations are within the scope of the present invention. In some embodiments, the cells seeded onto the assay substrates described herein are labeled on their surfaces with one or more fluorescent molecules, radioisotopes, and the like. It is contemplated that in some embodiments, labeling will increase the detectability and sensitivity of the signals generated by the disclosed assay systems. For example, in certain embodiments, a standard commercial plate reader (adapted to handle the LC assay formats described herein) is used to analyze areas of disorder and order in a liquid crystal and then determine cell number by analyzing fluorescence. The art is well acquainted with cell labeling technologies and with detecting labeled cells.

In other preferred embodiments of the present invention, asymmetrically (e.g., partially transparent and partially opaque) patterned substrates are provided that are useful for conducting cell migration assays that employ liquid crystal, fluorometric, colorimetric or densitometric readout methods. In the liquid crystal assay embodiments, the asymmetrically patterned substrates are configured to provide regions of order that orientate mesogens or to provide regions of disorder (e.g., random patterning) that do not orientate mesogens. The present invention contemplates that certain embodiments employing asymmetric substrates are useful for determining the effects of a test compound on cell migration by providing a tool for distinguishing chemokinetic from chemotactic cell migration. The underlying principle behind the embodiments employing asymmetric substrates and the various liquid crystal based assay configurations disclosed herein is basically identical. However, fluorometric, calorimetric, or densitometric based methods find use in these embodiments when the cells of interest are vitally, colorimetrically (e.g., for assays of dead cells) or fluorescently stained or otherwise labeled when the substrate provided is asymmetrically patterned with both optically transparent and optically opaque regions.

In preferred embodiments, cells (e.g., at least one cell) are seeded on the optically opaque portion of the assay substrate. In some of these embodiments, the cells are seeded in a cell seeding region (e.g., a depression in the assay substrate). In other embodiments, the cells are simply evenly distributed across the substrate and allowed sufficient time under appropriate conditions for attachment. The test region, encompassing both optically transparent and optically opaque (or patterned and non-patterned regions; the patterned regions of which orient LC mesogens) can be configured to correspond to the assay regions read out by commercial plate readers.

In certain embodiments disclosed herein, test compounds are placed in one or more reservoirs and the assays are conducted using protocols similar to those used in the liquid crystal based assays described above. In other embodiments, the asymmetrically patterned assay substrate further provides at least one microfluidic channel fluidically connecting at least one reservoir and the optically opaque and the optically transparent regions of the substrate.

The present invention contemplates detecting cells that migrate onto the transparent regions, or regions that are patterned to align liquid crystals of the asymmetric substrate. Cells that migrate onto the opaque regions or regions that don't align liquid crystals of the asymmetric substrate are hidden from detection.

Figure 27:
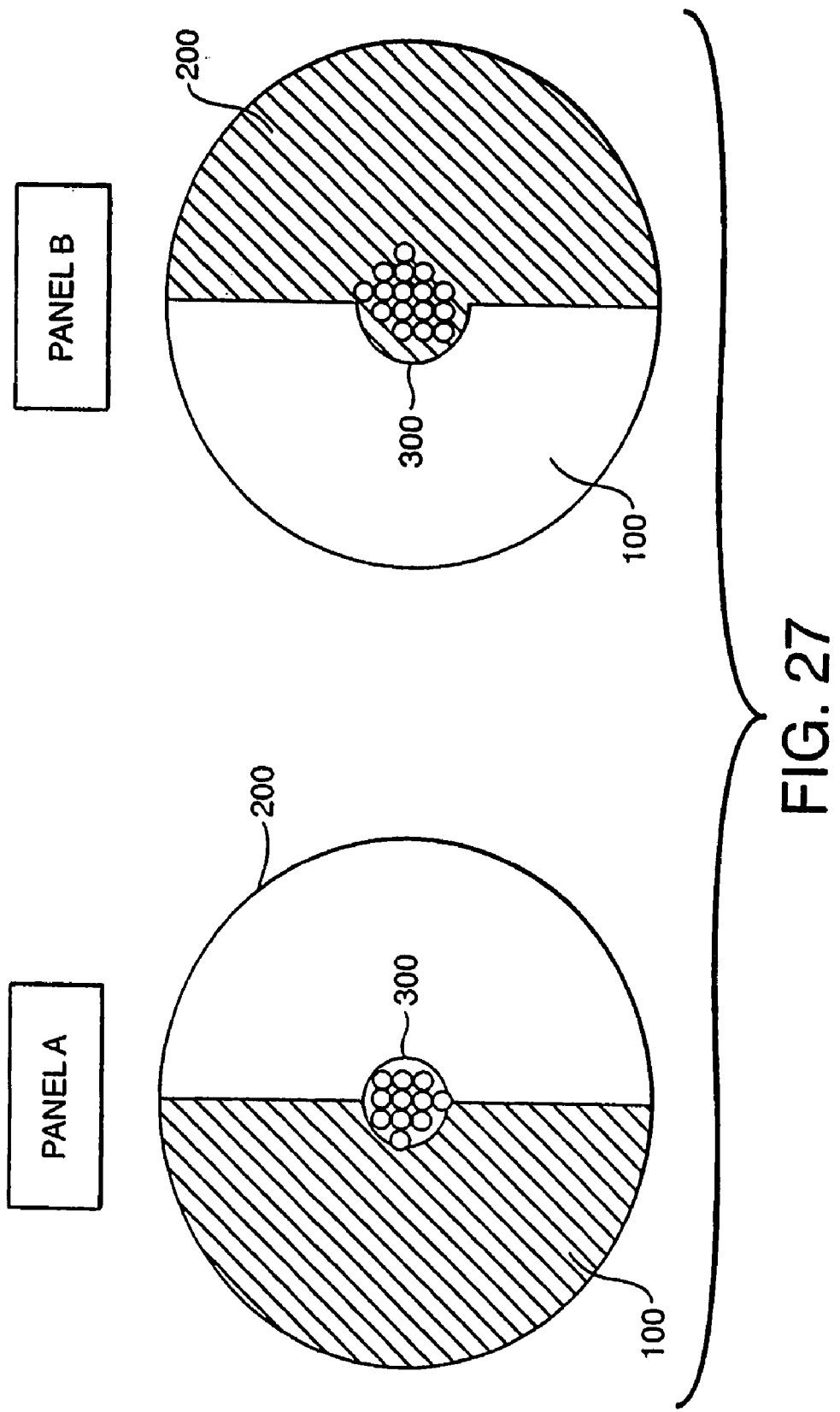
FIG. 27 is a schematic depiction of an assay device of the present invention.

FIG. 27 shows one embodiment of a contemplated asymmetric assay configuration. Referring to FIG. 27, Panel A depicts the use of an asymmetrically patterned nanostructured substrate for use with liquid crystal assays and Panel B depicts the design of an asymmetrically opaque substrate for use with colorimetric, fluorimetric, radiometric and other assays that detect the presence of cells. The assay substrate comprises a first region (100) which is patterned to align liquid crystal mesogens (panel A) or is substantially transparent for use with other assays of cell detection (panel B) and a second region (200) that does not orient liquid crystals and thus will not report the presence of cells with liquid crystal assays (Panel A) or is substantially opaque and will not report the presence of cells using other assays (exemplified by but not limited to colorimetric and fluorimetric assays) of cell detection (panel B). In certain embodiments, at the center of regions (100) and (200) is a position (e.g., depression) provided for seeding cells (300). The regions in FIG. 27 are depicted as semicircles. However, it will be understood that the substantially transparent and substantially opaque regions may be different in size and shape depending on the nature of the assay and detection equipment used. In some embodiments, protocols for using asymmetric embodiments of the present invention are substantially the same as those for using the conventional LC assay configurations described above.

Figure 28:
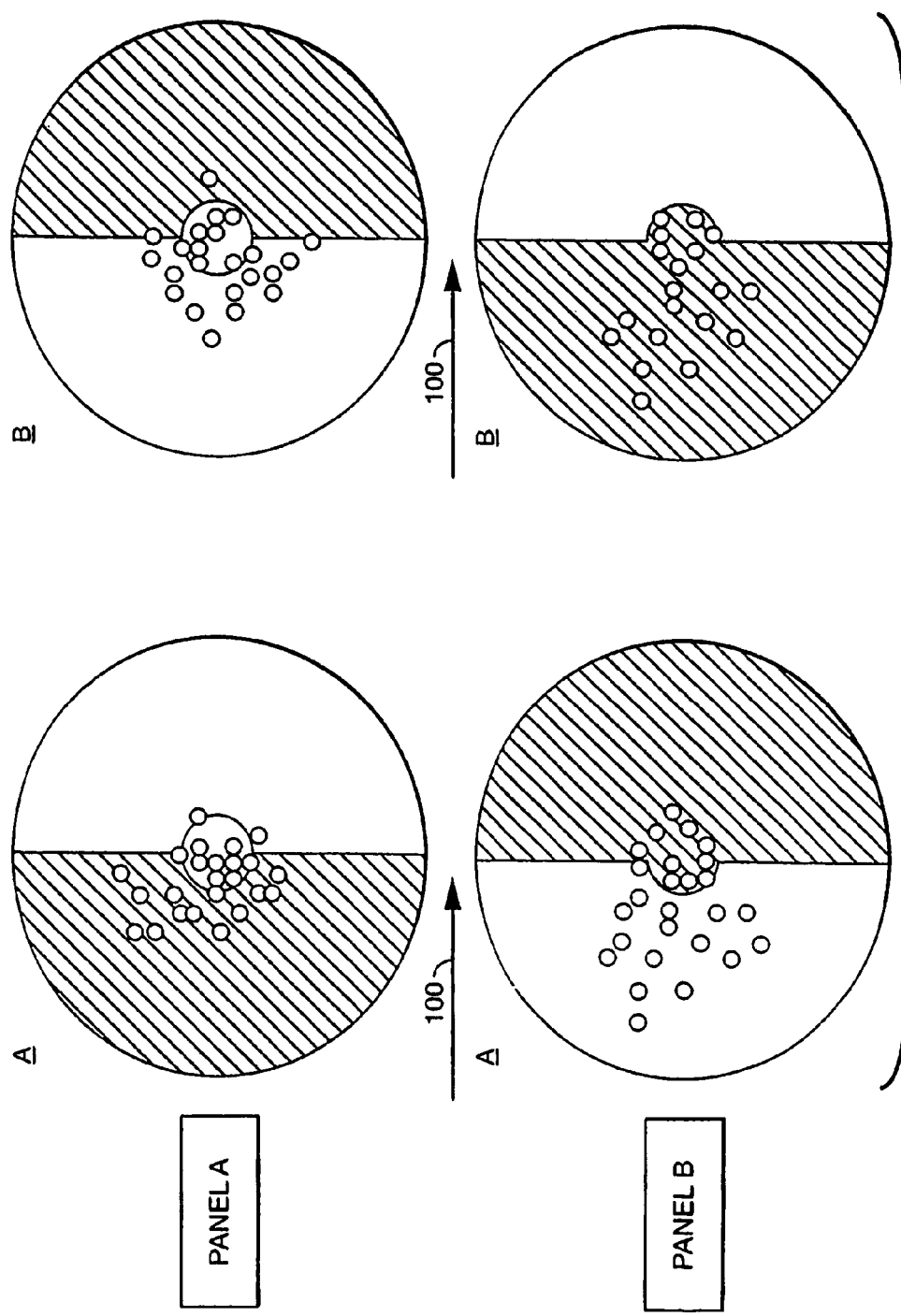
FIG. 28 is a schematic depiction of an assay device of the present invention in use.

FIG. 28 shows the expected effects of a test compound that exerts a chemotactic effect on cell migration. The arrows (100) indicate that a chemotactic gradient is originating from the left hand side. Panel A depicts the use of asymmetric substrates for use with liquid crystal assays. The presence of cells is only reported when they are located on regions that are nanotextured as to align liquid crystal mesogens (left hand side of substrate A in panel A and right hand side of substrate B in panel A). It is contemplated that by using paired asymmetrically patterned substrates that are oriented differently (see substrates A vs. substrates B in Panels A and B) in regards to the direction of a chemotactic signal and comparing the results, the user of the device is able to sort out whether a given test compound has no effect, or whether it induces chemotaxis or chemokinesis. With chemotactic stimuli, the cells move towards the origin of the chemotactic signal (100). A marked increase in the number of cells is detected when the patterned substrate is oriented on the left (substrate A of panel A).

Panel B of FIG. 28 demonstrates the use of asymmetrically patterned substrates for use with colorimetric or fluorimetric plate readers of other imaging devices that assay for cell number. Similar to the liquid crystal assay substrates, only one-half of the substrate allows for the determination of cell number (the left hand portion of substrate A and the right hand portion of substrate B in panel B).

Figure 29:
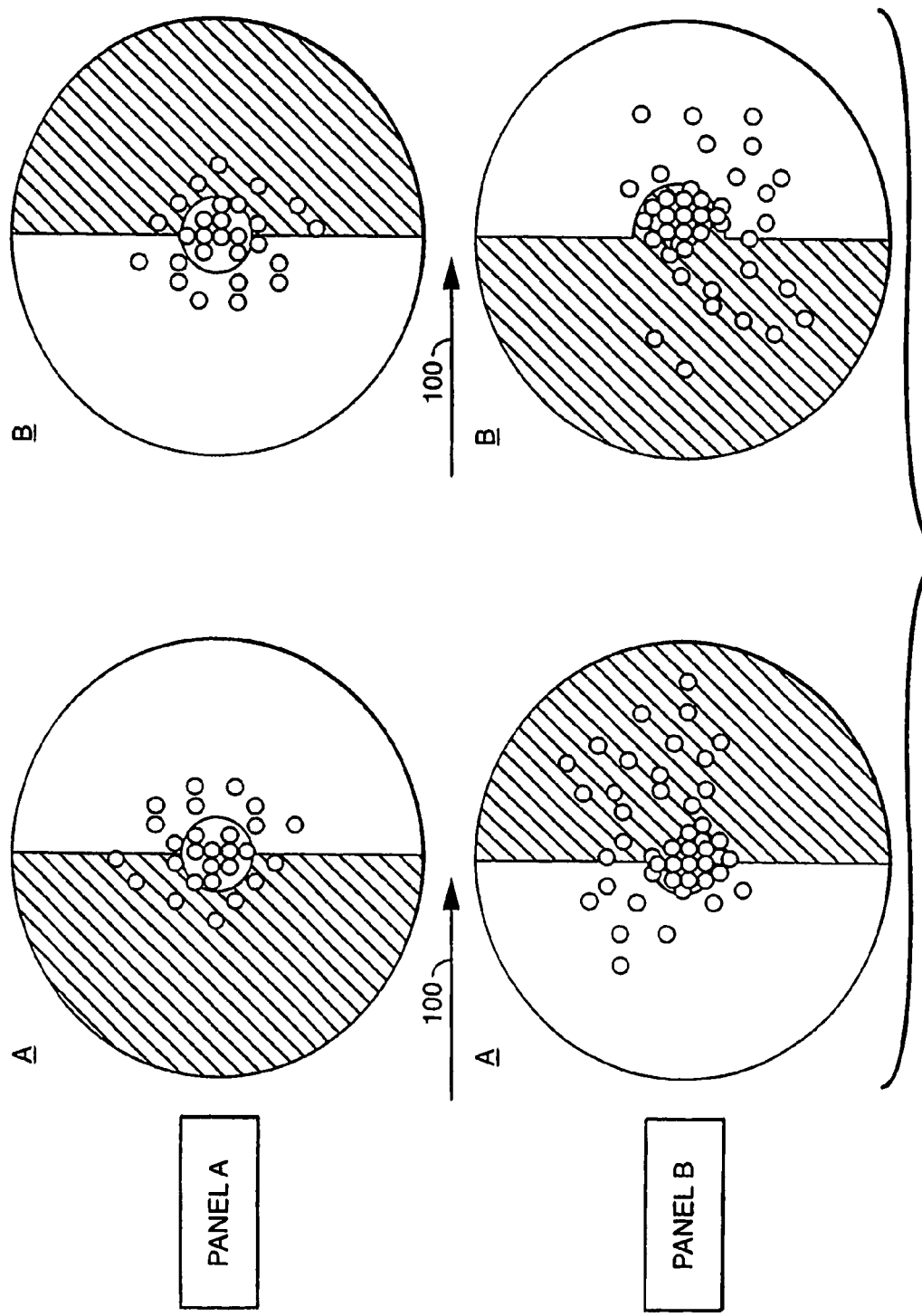
FIG. 29 is a schematic depiction of an assay device of the present invention in use.

FIG. 29 demonstrates the anticipated results for a test compound that stimulates chemokinesis (e.g., by demonstrating an increase in cell migration without a directional vector as regards the stimulus). The test compound gradient is originating from the left hand side (100). Panel A (substrates A and B) illustrates the results expected with liquid crystal assays and Panel B illustrates the results expected using colorimetric or fluorimetric assays. A greater number of cells are detected compared to controls (e.g., no chemotactic stimulus provided) and an equivalent number of cells are detected regardless of whether the substrate portion that can detect the presence of cells is oriented on the left (substrates A) or on the right (substrates B) relative to the direction of test compound gradient (100—originating from the left).

It is important to note that the asymmetric substrate embodiments present one adaptation of the general schemes and embodiments disclosed herein for conducting cell migration and motility assays. Thus, the present invention specifically contemplates that the substrates may comprise one or more microchannels and one or more reservoirs as described in detail above. Similarly, asymmetrically patterned embodiments are equally adaptable to multiple assay region microarray and plate reader sizes and formats (e.g., conforming to standard 24, 96, 384, 1536 well plate reader formats).

Figure 30:
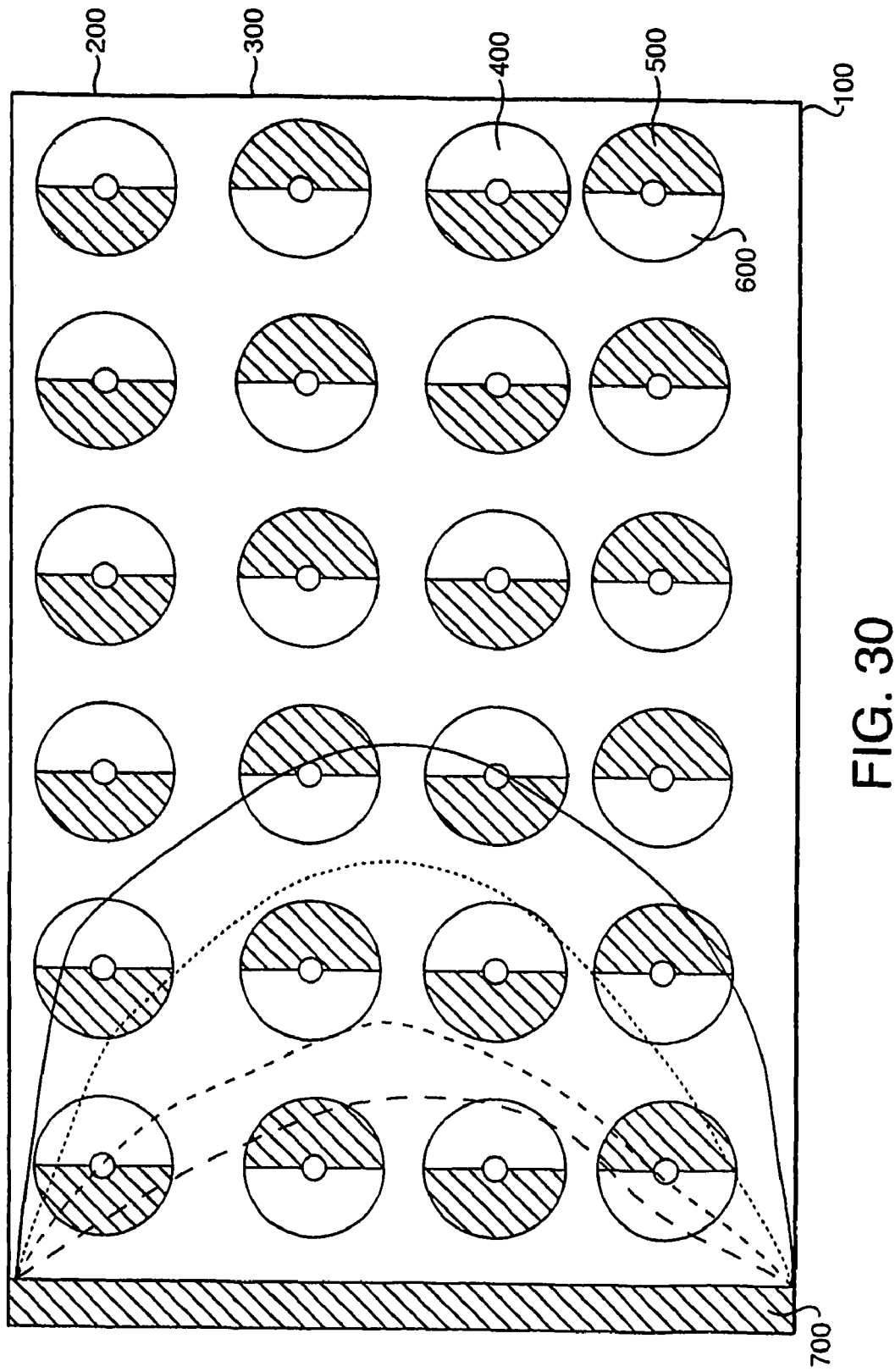
FIG. 30 is a schematic depiction of an assay device of the present invention.
Figure 31:
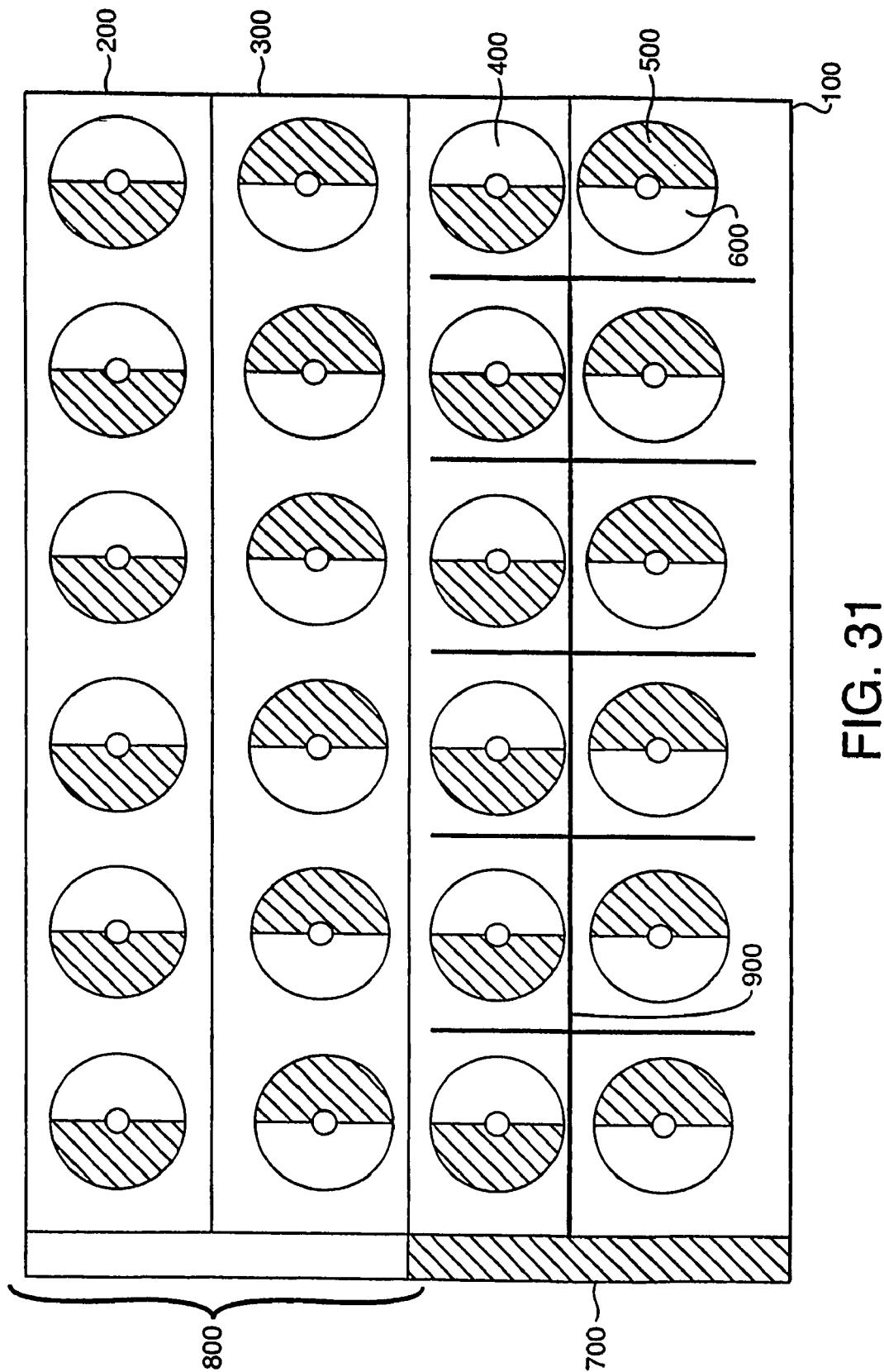
FIG. 31 is a schematic depiction of an assay device of the present invention.
Figure 32:
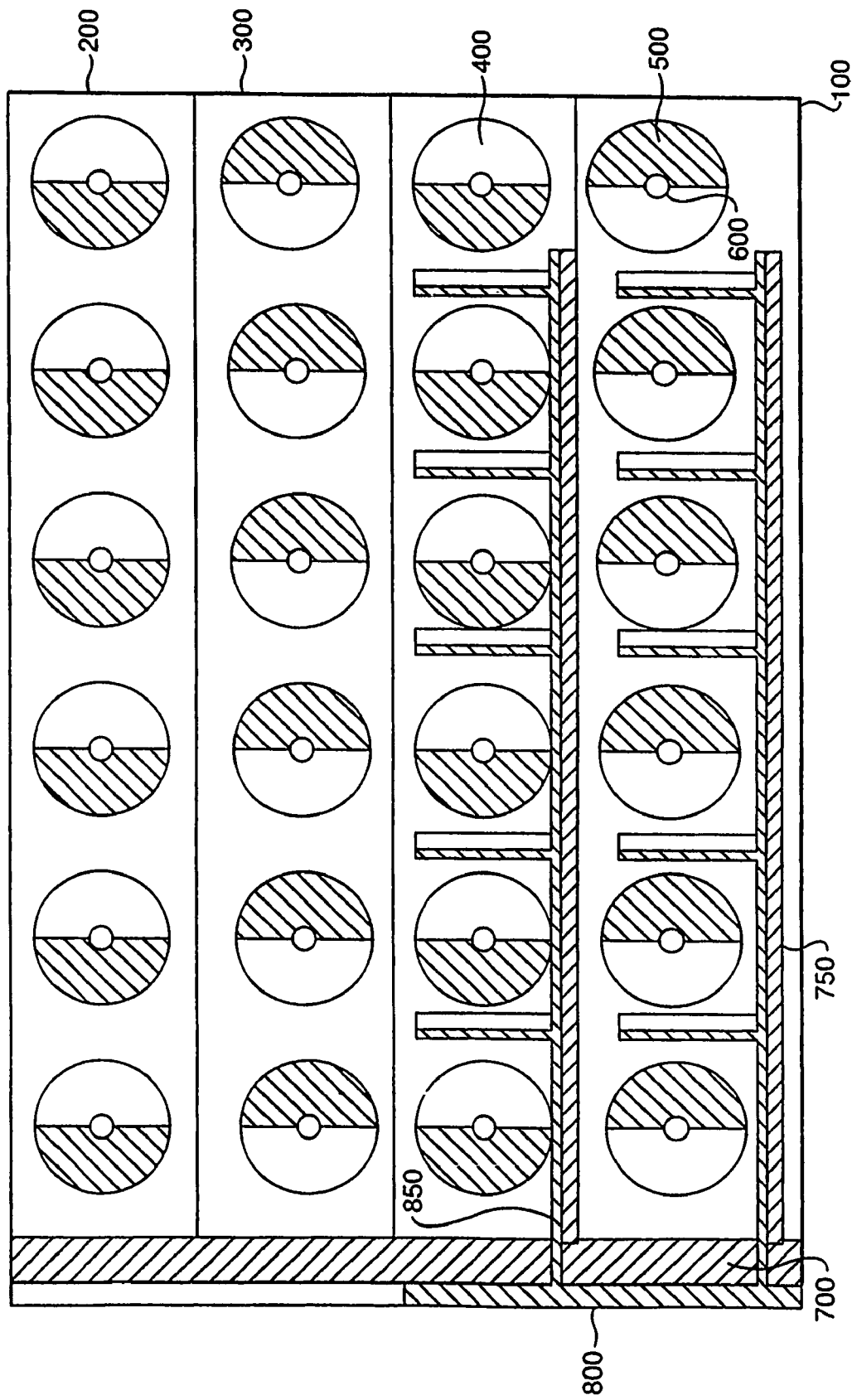
FIG. 32 is a schematic depiction of an assay device of the present invention.

In some preferred embodiments, the assays comprise a plurality (e.g., 2, 4, 12, 24, 48, 96 or more) of asymmetrically patterned regions orientated in an array. In particularly preferred embodiments, adjacent (e.g., neighboring) asymmetric substrate regions are arranged to provide alternating (e.g., opposing) orientations for neighboring optically opaque and the optically transparent regions. FIGS. 30 through 32 illustrate several contemplated asymmetrically patterned assay configurations designed to determine the affects of a test compound (or several test compounds and known compounds) on cell migration.

Referring to FIG. 30, a plurality of asymmetrically patterned assay regions (200) and (300) are configured in an array format on substrate (100). While illustrations CC through EE depict the use of asymmetrically patterned substrates for use with liquid crystal assays, the principle of asymmetric sampling of a substrate surface in a multiarray format is applicable also for use with colorimetric or fluorimetric assays as detailed in FIGS. 27 through 29. Each asymmetrically patterned assay region (200) and (300) further provides a region that is patterned to align liquid crystal mesogens (400) and a planar region that does not align liquid crystal mesogens (500). The presence of cells would only be reported, after the addition of liquid crystal mesogens, on assay regions that are capable of aligning the mesogens. The neighboring asymmetrically patterned assay regions ((200) and (300)) are orientated in a opposing arrangement in regard to the respective planar regions (400) and patterned regions (500) and located orthogonally relative to the site of origin of a test compound gradient (700). In preferred embodiments, the patterned region (500) of each asymmetrically patterned assay region ((200) and (300)) provides a cell seeding position (e.g., a depression) (600). The embodiment depicted in FIG. 30 further provides a reservoir (700) at one edge of substrate (100) for holding and dispersing at least one test compound.

It is contemplated that the assay configuration illustrated in FIG. 30 provides an increasingly attenuated concentration (dashed lines) of test compound from reservoir (700) to the asymmetrically patterned assay regions ((200) and (300)) as the distance of the asymmetrically patterned assay regions ((200) and (300)) from reservoir (700) increases. Analysis of cell migration data obtained from asymmetrically patterned assay regions ((200) and (300)) provides information as to the relative potency of the test compound. For instance, a strongly chemotactic test compound more strongly stimulates the migration of cells towards the origin of the compound (700) in the asymmetrically patterned assay regions ((200) and (300)) distant to reservoir (700) at a given time point than would a weakly chemotactic test compound. In preferred embodiments, the asymmetrically patterned assay regions ((200) and (300)) are orientated on substrate (100) to provide for automated data acquisition and analysis (e.g., using a plate reader).

FIG. 31 represents another embodiment where substrate (100) provides one or more rows that serve as controls of asymmetrically patterned assay regions (800) that are prohibited from contacting a test compound. FIGS. 31 and 32 also illustrate assay configurations where one or more microfluidic channels. (e.g., 900 of FIG. 31 and 750 & 850 of FIG. 32) are provided to uniform delivery of test compounds across the substrate (100).

The present invention is not intended to be limited to the asymmetrically patterned assay configurations described above and in FIGS. 30 and 31. Indeed, a number of assay region configurations are possible when employing larger numbers (e.g., 48, 64, 96, 384, or 1536, or more) of asymmetrically patterned assay regions on a single substrate. FIG. 32 briefly illustrates an embodiment where a first reservoir (700) and accompanying microfluidic channels (750) containing a known chemotactic agent are positioned in proximity to a second reservoir (800), and accompanying microfluidic channels (850) containing a test compound. The other elements illustrated in the asymmetric assay configuration depicted in FIG. 32 are common to those described in FIGS. 30 and 31, respectively. It is contemplated that the model assay configuration illustrated in FIG. 32 provides for evaluating the ability of a test compound to affect (e.g., augment or inhibit) a known chemotactic agent.

In some embodiments of the use of asymmetric substrates with patterned surfaces, the assay region will be patterned over its entire surface, but asymmetric sampling will occur due to the asymmetric presence of an underlying opaque component that prevents the transmission of light. FIG. 33 demonstrates one such embodiment. In FIG. 33, panel A is a top-view of an assay region (100) and panel B is a cross sectional view of the same assay region. It can be seen that the assay region is asymmetric in its sampling capabilities, with light being transmitted through region 200 but not through region 300. The entire surface of the assay region is nanopatterned (600) to align liquid crystal mesogens. Underlying the nanopatterned surface however is an asymmetrically opaque substrate that is optically clear (400) underlying region 200 and optically opaque (500) underlying region 300. Thus, data are collected, as to the presence of cells on the surface (which disturb the orientation of liquid crystal mesogens placed on their surface) only in the portion of the substrate that is optically clear (200). This design has application to all of the embodiments described above that utilize asymmetrically patterned or asymmetrically opaque substrates (e.g. see FIGS. 27 through 32)

It is possible to use this strategy by programming a plate reader to take asymmetric readings within a single test area. Currently, many commercial plate readers take multiple readings within a single well and average the readings. A reader could be programmed to take readings asymmetrically within a test area and could therefore be used to determine chemotaxis and chemokinesis as outlined in previous descriptions. These embodiments are illustrated in FIG. 34.

In some preferred embodiments, a plate reader is programmed so that the sensing element(s) obtain multiple discreet readings within a single analytic zone or to scan an analytic zone to locate the perimeter and calculate the diameter of an outwardly spreading population of cells. In this embodiment, cells are seeded centrally onto a distinct cell seeding area. In some embodiments, the cells are seeded using a specifically designed cell seeding device described below that constrains the distribution of cells to a discrete location within the analytic zone (such as the center of a single well of a 24, 96, 384 or 1536 multiwell plate). After initial incubation in the cell seeding device to allow for cell attachment (time dependent on culture conditions and cell type), the cell seeding device is removed and nonattached cells gently removed by irrigation. The substrate with cells is then incubated again (time dependent on culture conditions and cell type) and the migration of cells outward from the initial cell seeding area determined using the programmed sensing elements and analytic software. If a factor is added to the media (such that no gradient of the factor is present in the media) that promotes cell migration then the outline of the outwardly migrating cells will roughly define a circle with the diameter of the circle being proportional to the potency of the factor to stimulate cell migration.

Similarly, this procedure could be used to evaluate compounds that inhibit cell migration. Such assays are important for screening of possible therapeutic compounds for the treatment of cancer. In some preferred embodiments, this procedure is used to assess the ability of test compounds to inhibit migration of vascular endothelial cells which is often used as a positive indicator for compounds used in cancer treatment. The programming of the mechanical drivers of the sensing element(s) and analytic software is easily accomplished by those of ordinary skill in the art. In some embodiments, the cell seeding area is optically opaque to avoid being read out as containing cells or it could be transparent and the perimeter of the cells seeded into a defined area recorded and their location determined. In other embodiments, the sensing element(s) are programmed to avoid obtaining readings from the initial cell seeding area.

Figure 35:
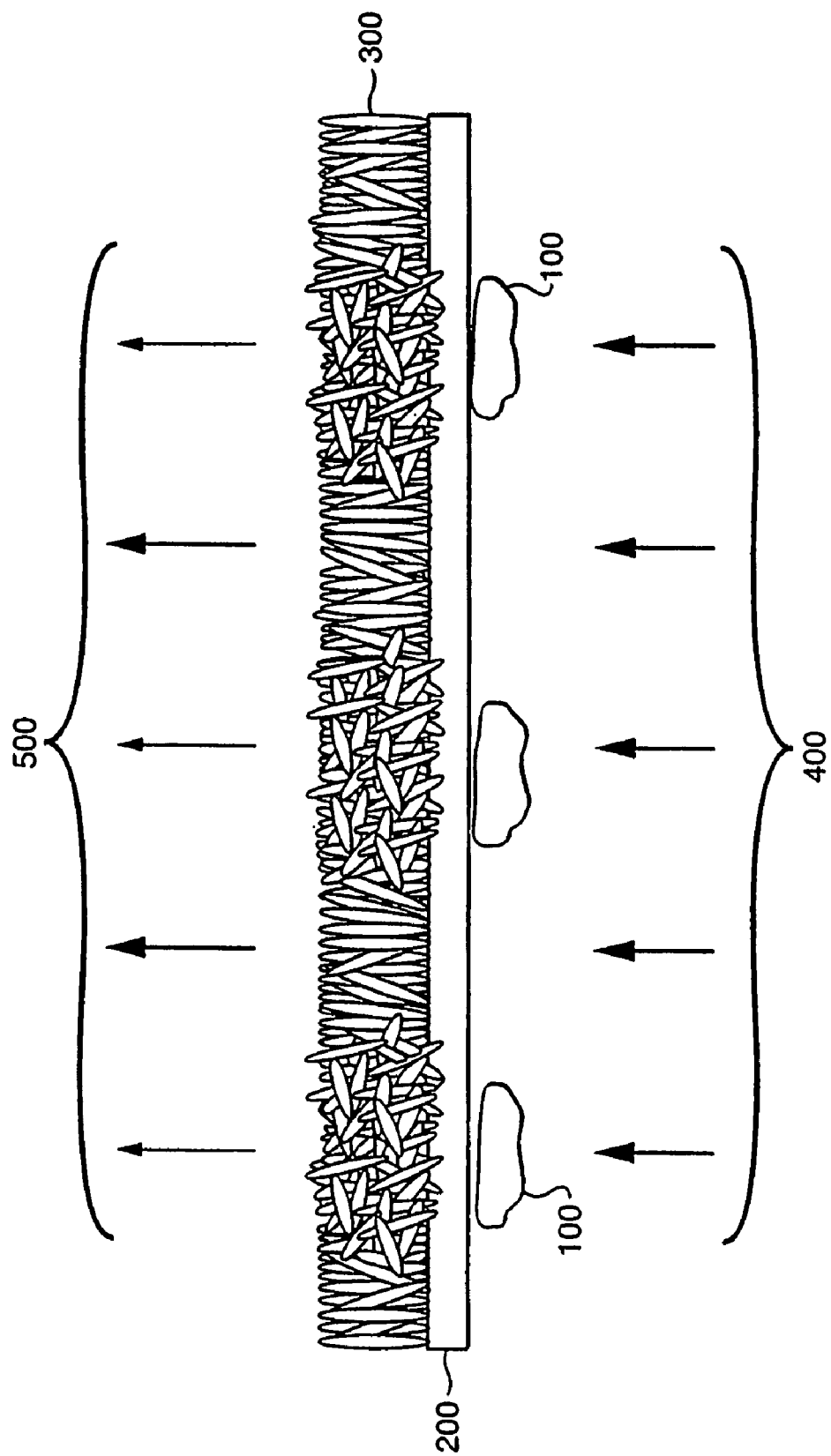
FIG. 35 is a schematic depiction of an assay device of the present invention.

It must be noted that this approach is not limited to use with liquid crystal based assays but is broadly applicable to biophotonic techniques such as calorimetric, optical densitometric, fluorometric and radiometric methodologies. Using this strategy, assays that separate out chemokinesis from chemotaxis can be performed by provision of a chemotactic gradient to the initially seeded cells (using a fluidic delivery system or a degradable pellet to create a gradient of chemotactic factor(s)) and then obtaining multiple readings of cell location within an analytic zone. The software provides either analysis of discrete regions within an analytic zone or is used to determine the resultant size and major axis of the dispersed colony of cells. If a compound is chemokinetic the dispersed cells will be evenly distributed around the initial cell seeding area creating a roughly circular outline with the diameter of the circle being proportional to the potency of the chemokinetic compound while a chemotactic compound will induce the cells to preferentially migrate towards the source of the factor creating an ellipse with the long axis diameter being proportional to the relative chemotactic potency of the compound. This procedure could be done by modifying the software that determines the spatial location of the sensing element(s) and the analytic software. In another embodiment of the invention, a motive force (including but not limited to electrical fields, magnetic fields, and thermal fields) is used to orient thin films of liquid crystal mesogens such that they report the presence and spatial location of cells attached to a substrate. In this embodiment, the mesogens are not in direct contact with the cells. This embodiment makes use of the fact that attached cells create defined zones of impedance (e.g., electrical and/or magnetic and/or thermal) that attenuates the motive force(s) transmitted into the liquid crystal film. An example of this embodiment is depicted in FIG. 35. Cells (100) are seeded onto a non-conducting substrate (200) and allowed to attach (the attachment time is dependent on cell type and culture conditions). The substrate (200) may be functionalized by adsorption or covalent bonding of constitutents that support cell attachment and function (including, but not limited to, extracellular matrix proteins such as collagens, laminins, fibronectin, vitronectin, osteopontin, thrombospondin, Intercellular adhesion molecule-1 (ICAM-1), ICAM-2, proteoglycans such as chondroitin sulfate, von Willebrand factor, entactin, fibrinogen, tenascin, Mucosal adressin cell adhesion molecule (MAdCAM-1), C3b, and MDC (metalloprotease/disintegrin/cysteine-rich) proteins), nucleic acids, specific receptors and cell receptor recognition sequences (e.g., cadherein, immunoglobulin superfamily, selectin, mucin and integrin binding sequences such as RGD, EILDV, LDV, LDVP, IDAP, PHSRN, SLDVP, GRGDAC, and IDSP)). Once attached, a thin film of liquid crystal mesogens (300) is placed in contact with the surface of the substrate opposite to the surface to which cells are attached. With attached cells it makes no difference if the cells are on the upper or the lower surface. A motive force (400, represented by large arrows on lower part of diagram) that is capable of orienting liquid crystal mesogens once a threshold level is attained, is applied across the substrate (100). The magnitude of the motive force is set to be just above threshold for orienting the liquid crystal mesogens overlying the substrate (200) in regions where cells are not attached. At near threshold values, the impedance of attached cells will prevent the orientation of mesogens located on the substrate (200) immediately opposite their site of attachment. The differential attenuation of the motive force as it passes through the cells, substrate and subsequently through the LC film is represented by differing size arrows in the upper part of the diagram (500). This results in regions of the liquid crystal film where mesogens are oriented by the motive force and regions (correlating to cell attachment zones) where mesogens are not exposed to a sufficient magnitude of motive force to cause orientation of mesogens.

In preferred embodiments, the motive force is an electric field applied by first and second electrodes positioned on either side of the substrate. In preferred embodiments, an aqueous electrolyte is incorporated between the cell side of the substrate and the first or second electrode. The electrodes are preferably either solid slab-type electrodes, or more preferably made of a wire mesh. In operation, a potential difference is applied across the substrate. The presence of cells perturbs the electric field lines in a manner that perturbs orientation of the liquid crystal, causing the cells to be imaged.

This embodiment has applications for the detection of cell number useful in assays of cell attachment and cell proliferation. Additionally, since the magnitude of motive force impedance directly correlates with firm cell attachment to the substrate, this embodiment is useful for evaluating the toxic effects of test compounds. A compound toxic to cells will cause weakening or dissolution of attachment to the underlying substrate that in turn results in a quantifiable loss of impedance thus making the mesogens opposite the region occupied by the cell more succeptible to the orienting influence of the motive force(s).

Figure 36:
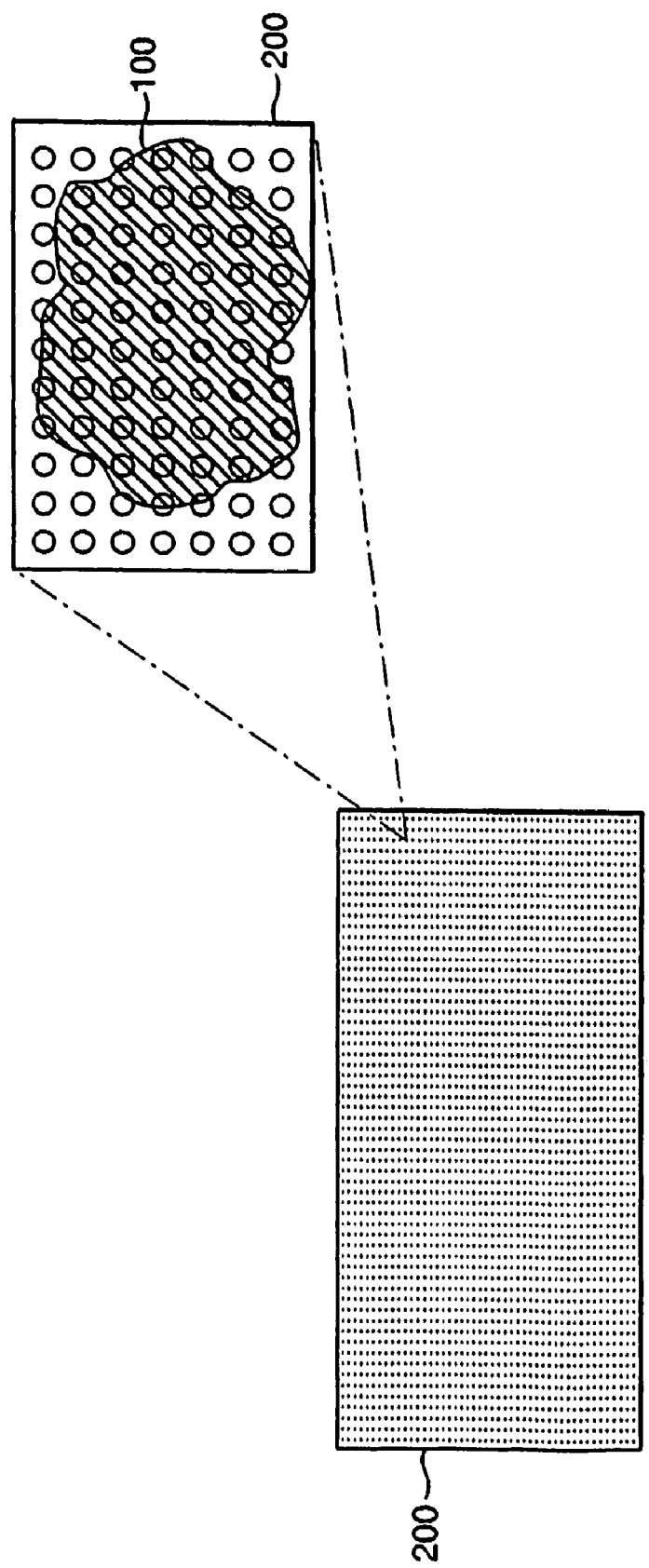
FIG. 36 is a schematic depiction of an assay device of the present invention.

FIG. 36 demonstrates another embodiment of the invention. In this embodiment, cells (100) are seeded on a substrate (200) that has 10 nm to 1 µm diameter perforations in it (300). Such a substrate can be fabricated using a variety of techniques including but not limited to photolithography, x-ray lithography and e-beam lithography. The registered array of perforations would be introduced into a substrate that is insulating in nature, preventing transmission of motive forces into the liquid crystal mesogens located on the surface opposite the surface cells are attached to. A thin conducting fluid layer (biologically inert to cells) is placed on the surface opposite the cells prior to placement of a thin film of LC mesogens. This creates distinct zones of readout of known spatial distribution that will facilitate development of automated process for information processing.

Figure 37A:
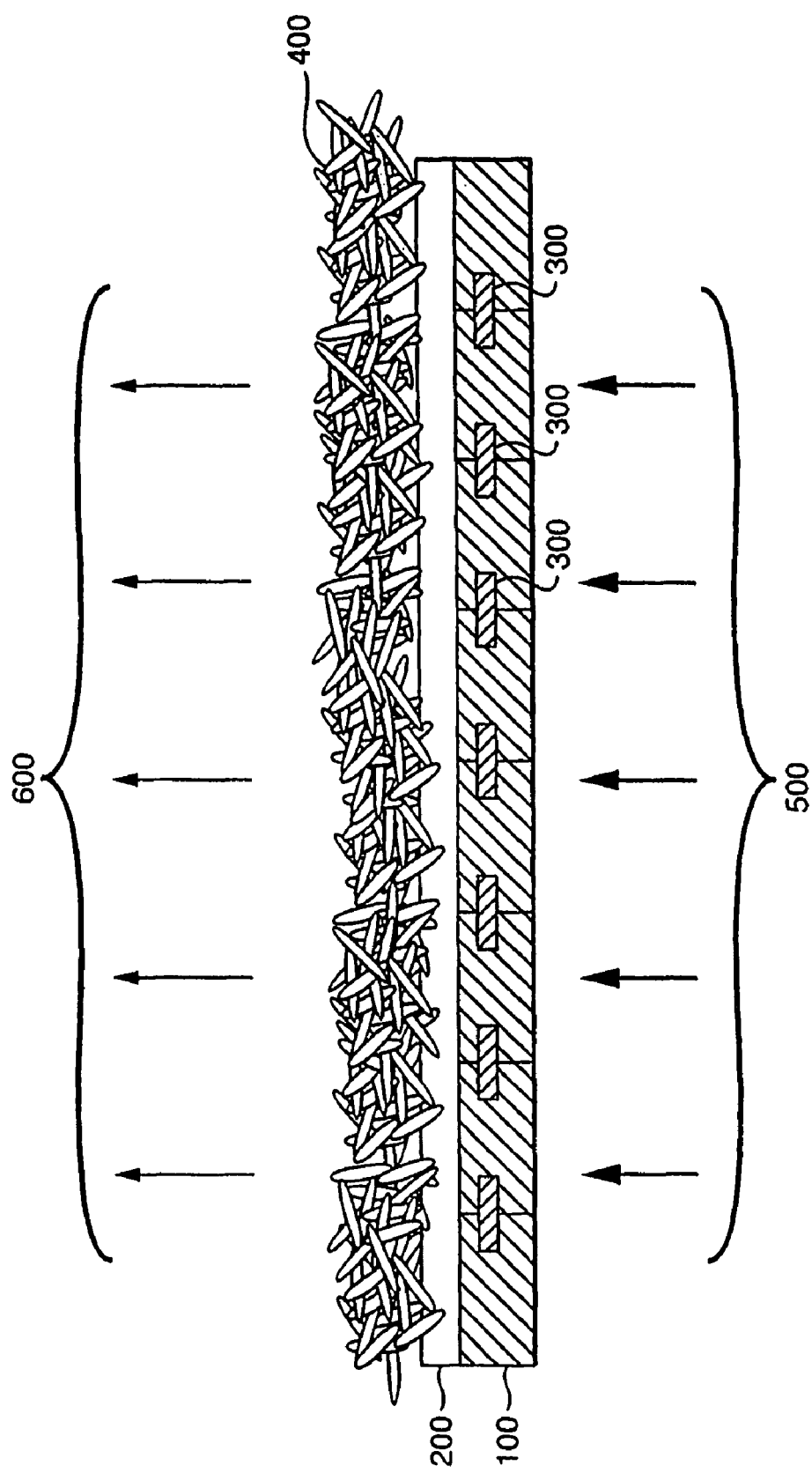
FIG. 37A is a schematic depiction of an assay device of the present invention.

In other embodiments, cells are grown to confluence on test substrates which allow assessment of the integrity of intercellular adhesions. Similar to assays that utilize transepithelia membrane resistance to the conduction of electric fields, this assay has applications to studies of functional morphology, for studies of pathobiology of infectious organisms, to the evaluation of toxic effects of test compounds, and to the in vitro evaluation of neoplastic invasiveness (Zak et al). An example of this embodiment is given in FIGS. 37A and 37B. Cells (100) are seeded on a substrate (200) that conducts a motive force (eg, electrical and/or magnetic and/or thermal fields). Epithelial cells are incubated and allowed to grow to confluence at which point they develop intercellular junctions (300) which makes them more resistant to transmitting motive forces through the substrate and subsequently into a thin film of liquid crystal mesogens (400). At near threshold values of motive force (large arrows in lower part of illustration (500) the intact cellular monolayer prevents transmission of sufficient motive force to align LC mesogens. The attenuation of motive force by the intact epithelial monolayer is depicted by small arrows (600) in the upper part of FIG. 37A.

Figure 37B:
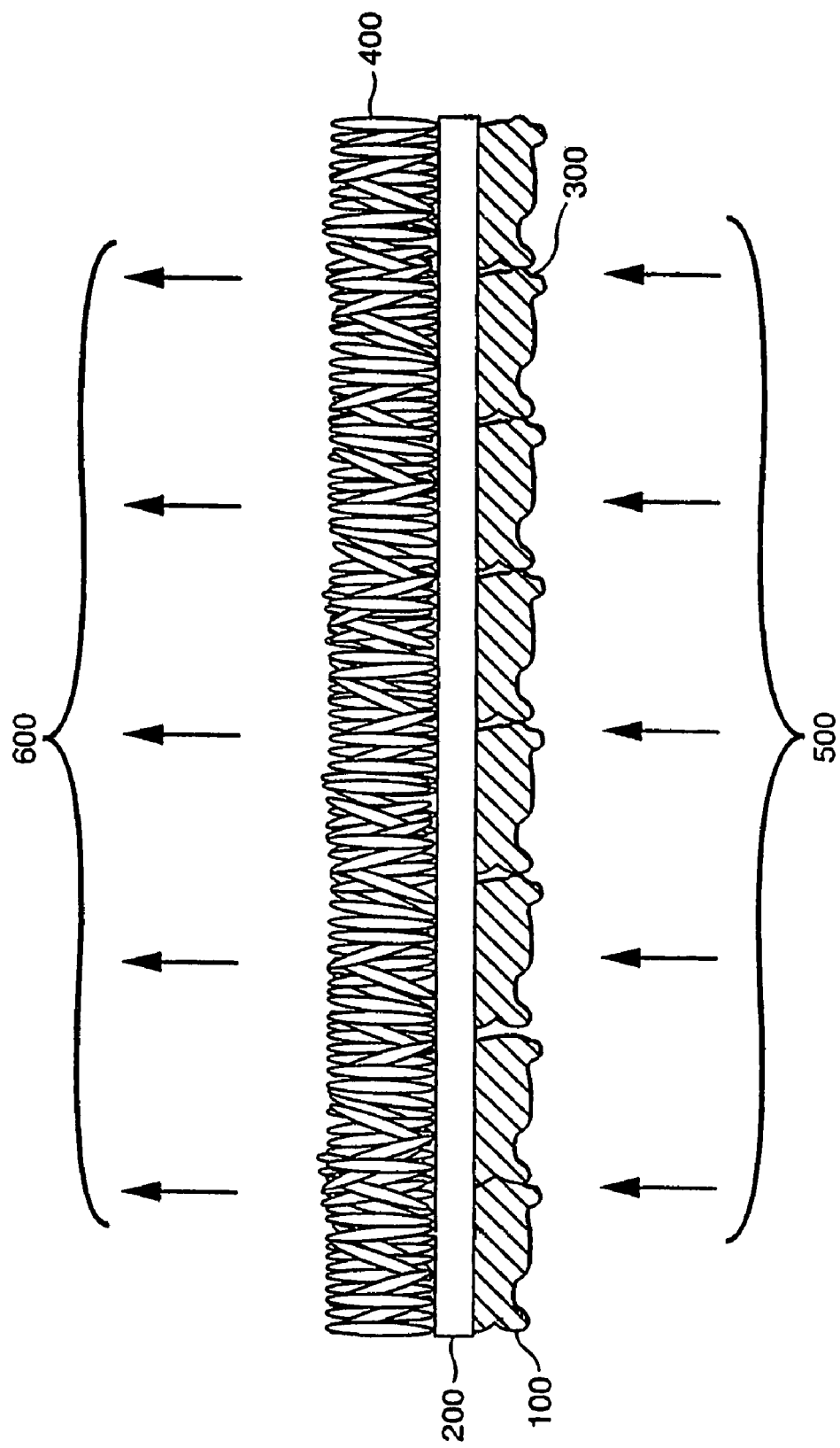
FIG. 37B is a schematic depiction of an assay device of the present invention.

FIG. 37B depicts the consequences of exposure to a test compound that is toxic for the epithelial cells. In this case cellular toxicity (100) is manifested by a breakdown of the intercellular junctions (300) and a loss of impedance (resistance) of the epithelial layer to transmission of motive force(s) into the mesogenic layer located on the surface opposite the cells. In this case, the motive force is sufficient (depicted by large arrows—600) to align the mesogenic layer. This change in the orientation of the liquid crystal mesogens can be quantitated by all of the means previously described in this application. Orientation shifts in the liquid crystal mesogen orientation can be continuously monitored prior to and after exposure to test compound or can be quantitated at pre-determined time points.

Figure 38A:
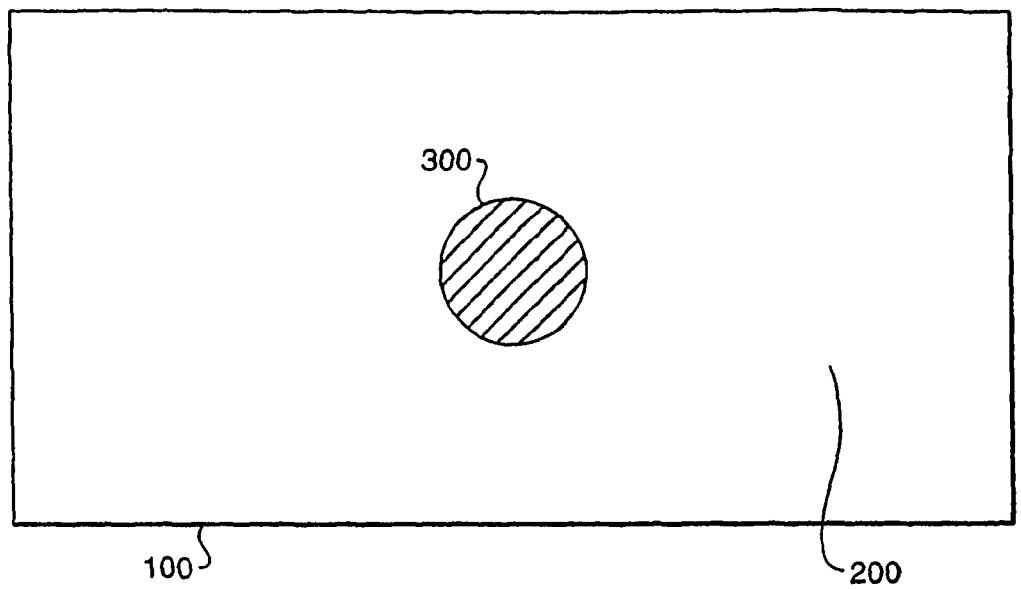
FIG. 38A is a schematic depiction of an assay device of the present invention.

In some embodiments, the substrate (100) consists of an insulating material (200) (e.g., glass in the case of using electric fields as the motive force) with a central window (300) comprised of a conducting material, capable of supporting cell attachment and function, that allows the transmission of motive force(s). These relationships are depicted in FIG. 38A.

Figure 38B:
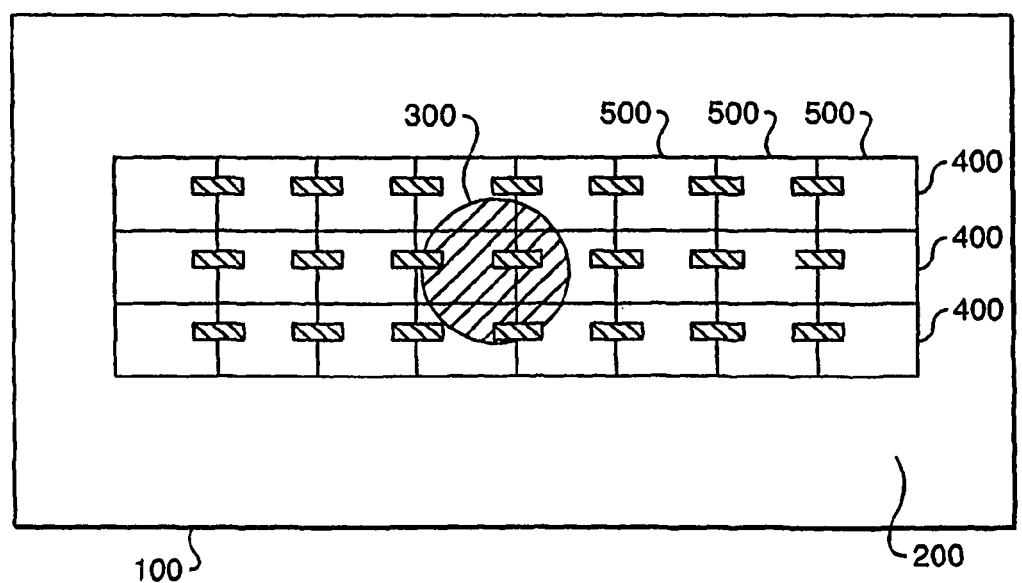
FIG. 38B is a schematic depiction of an assay device of the present invention.

FIG. 38B illustrates the use of this substrate with cells. Cells (400) are seeded on the substrate (100) that is comprised of an insulating material (200) and contains a central window (300) that is conductive for the motive force(s) being used to orient LC mesogens. Once confluence is reached mature intercellular adhesions form (500) that contributes to the resistance to passage of the motive force(s).

In another embodiment, LC mesogens are used to report electrical activity of cells in culture. Types of cells of interest for study include, but are not limited to, neuronal cells, cardiac cells and muscle cells. In this embodiment, cells are cultured on standard laboratory plastic or glassware. A thin film of LC mesogens either non-toxic to the cell type being studied and/or separated from the cell by addition of a thin film of phospholipid that has been shown to interface with mesogenic layers. Electrical activity in the cell results in alteration of the orientation of LC mesogens immediately adjacent to the cell. This change in order can be visualized using all of the techniques previously described.

C. Cytology Assays

In still further embodiments, the present invention provides compositions and methods for reporting cytoskeletal alignment in cell membranes. For example, in certain embodiments, liquid crystals are used to report the order of cytoskeletal elements transmitted through the cell membrane. In some embodiments, the liquid crystal layer is placed directly onto the cells of interest. In other embodiments, the membranes of the cells of interest are solubilized (e.g., using surfactants) to reveal the cytoskeleton to the liquid crystal layer itself. In some embodiments, the liquid crystal layer can be the surfactant (e.g., lyotropic liquid crystals).

Figure 39:
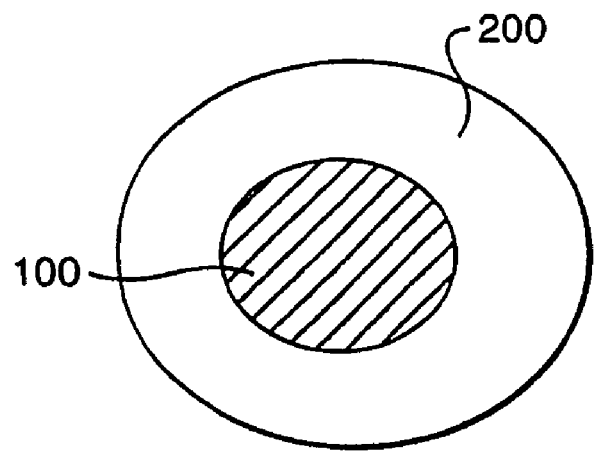
FIG. 39 is a schematic depiction of an assay device of the present invention.

In other embodiments of the present invention, compositions and methods are provided for quantitating the production of specific (or nonspecific) cellular secretory products. The present invention further contemplates specific embodiments directed to quantitating the secretion of specific secretory products in response to contacting cells of interest with one or more compounds that induce secretion of extracellular products. In a preferred embodiment, a nanostructured substrate is fabricated with specific binding sequences incorporated into its surface (e.g., targeted to bind a specific protein product of the cell such as a growth factor or cytokine). Cells of interest are seeded onto the substrate and allowed to attach and grow under appropriate conditions. In a preferred embodiment of the invention, the surface that supports the cells is a second surface, and the first surface is that surface that is fabricated with specific binding sequences incorporated into its surface. This second surface may be placed above or below the first surface. Production of a gradient of liquid crystal response is visualized as a halo effect around the cell(s) with the greatest concentration of a specific factor being closest to the cell(s). (See, FIG. 39). Briefly, FIG. 39 shows the zone of liquid crystal response (200) produced around a cell(s) of interest (100) upon secretion of a specific secretory product by the cell(s). It is contemplated that an estimation of the amount of product secreted by a cell can be correlated to the diameter (ring) of liquid crystal response surrounding the cell. For example, in one specific embodiment, the assays and techniques disclosed herein allow for evaluating cellular secretion of Nerve Growth Factor (NGF) in response to exposure to one or more trophic factors such as EGF.

Figure 40:
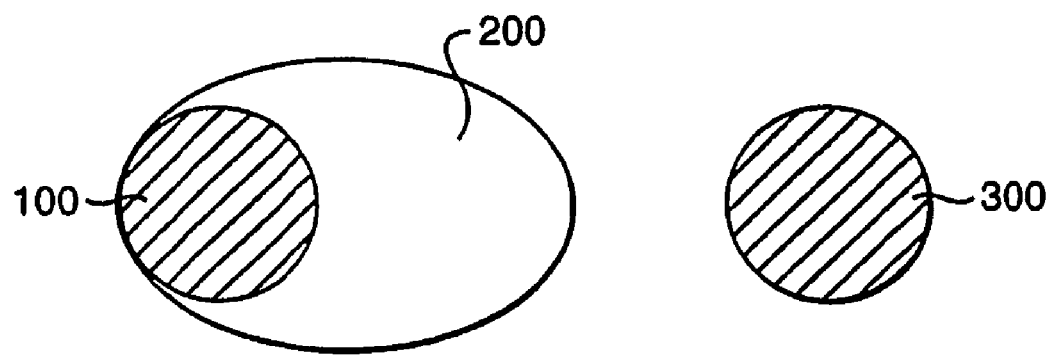
FIG. 40 is a schematic depiction of an assay device of the present invention.

From the above examples, it is clear that the present invention allows for the investigation of cellular secretory responses of single cells or small groups of cells to a variety of environmental stimuli. It is also clear that these techniques and assay substrates allow for the detection and quantitation of cellular factors that are secreted asymmetrically in response to environmental stimuli delivered by additional cells. (See, FIG. 40). FIG. 40 shows, the zone of liquid crystal response (200) produced by a cell(s) of interest (100) upon secretion of a specific secretory product influenced by the presence of another cell (300). Examples would be the stimulation of secretion of factors by epithelial cells (100) due to factors released by adjacently located neuronal cells (300).

Figure 41:
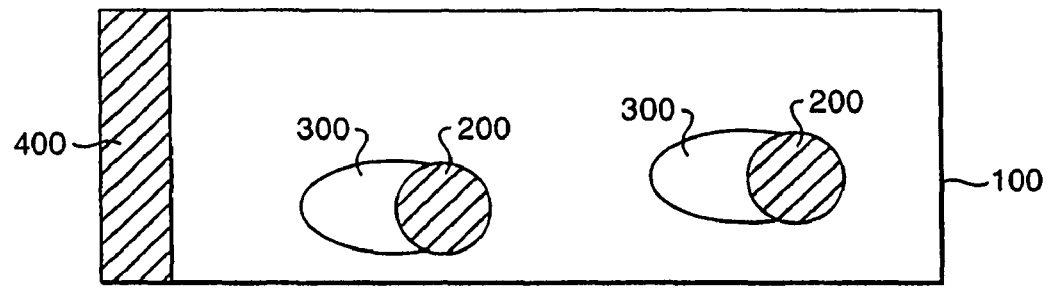
FIG. 41 is a schematic depiction of an assay device of the present invention in use.

In still other embodiments, the secretory response assays disclosed herein are adapted for use with the substrates, reservoirs, and microfluidic systems disclosed above, such that a cell's secretory profile can be quantitated in response to one or more compound gradients established across a liquid crystal surface. For example, FIG. 41 shows the secretory response (300) of two cells (200) reported through a suitable liquid crystal surface (100) in response to a compound gradient established by a reservoir (400) on the substrate.

In a preferred embodiment of the invention, micrometer and nanometer-sized channels are patterned into the surfaces that support the cells. The flow of liquid along the channels permits the sampling of secretory products from the cells that cover the channel. The secretory products collected from the channel can be assayed by using methods that involve the use of liquid crystals, which are well known to those skilled in the art, of by conventional methods of analysis such as mass spectroscopy, UV-Vis absorption spectroscopy, ELISA, gel electrophoresis and other methods of analysis applicable to secretory products.

Figure 42:
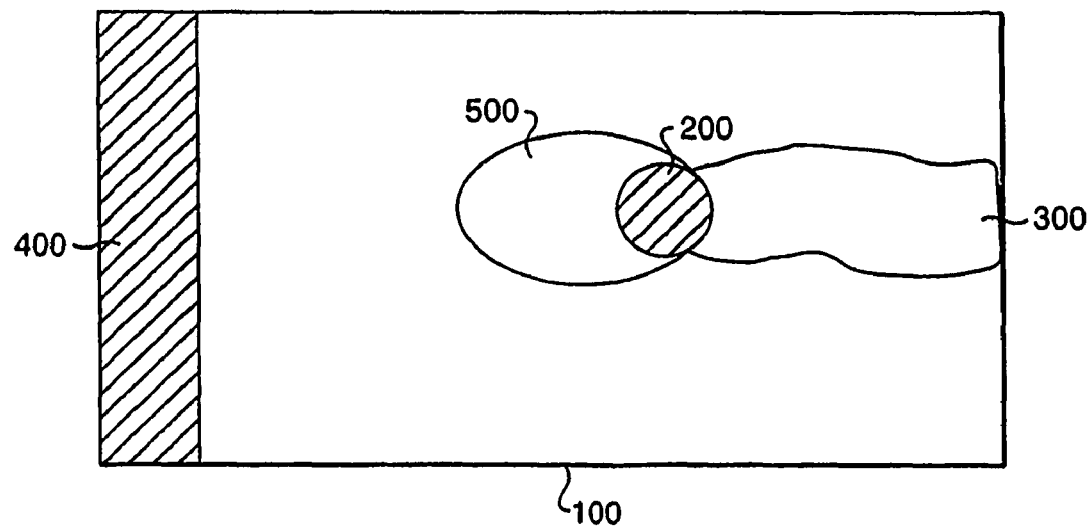
FIG. 42 is a schematic depiction of an assay device of the present invention.

It is contemplated that the cell secretory product assays can be engineered (e.g., adapted) for use with any of the cell migration and motility assay configurations disclosed herein, thus allowing the detection of asymmetric secretion in association with cell migration. In FIG. 42, the nonspecific interaction of the cell (200) during migration across the substrate (100) (having a test compound reservoir (400)) creates a change in the order of the surface of the substrate (100) in its wake which is reported by the liquid crystal layer (300), the presence of the cell (200) is reported by the cell blocking access of the ordered substrate to the liquid crystal layer placed on top and the presence of a specific secretory product (500) of the cell is being reported by the specific receptors which have been incorporated into the nanostructured surface of the substrate (100). A reservoir (400) has been incorporated into this example to demonstrate an asymmetric secretory process (500) by the cell (200) in response to a gradient of a soluble factor being delivered across the surface of substrate (100).

Changes in the metabolic states of cells give rise to changes in the heat output. Because the order within a liquid crystalline can be a strong function of temperature, liquid crystals can be used to detect changes in the heat output of cells. For example, calorimetric changes can be associated with change in metabolic state such as phagocytosis via stimulation with LPS. This could be by simply placing LC on a single cell or population of cells on a nanostructured (ordered) substrate or by using the hybrid ECM-LC. A preferred embodiment of the invention, makes use of mixtures of liquid crystals that possess phase transitions at the temperatures similar to those used for cell cultures. In a preferred embodiment of the invention, the liquid crystal is cooled towards a phase transition and the appearance of the liquid crystal is monitored during the ramp in temperature. The liquid crystal can be a liquid crystalline substrate on which cells are grown. A preferred embodiment of the invention is a liquid crystalline substrate that is decorated with phospholipids or other biological receptors that interact with cells. The liquid crystals can also be lyotropic liquid crystals, and thus cell culture can occur in the presence of the liquid crystal overlying the cells during imaging of the cells.

D. Plate Top Devices

Figure 43:
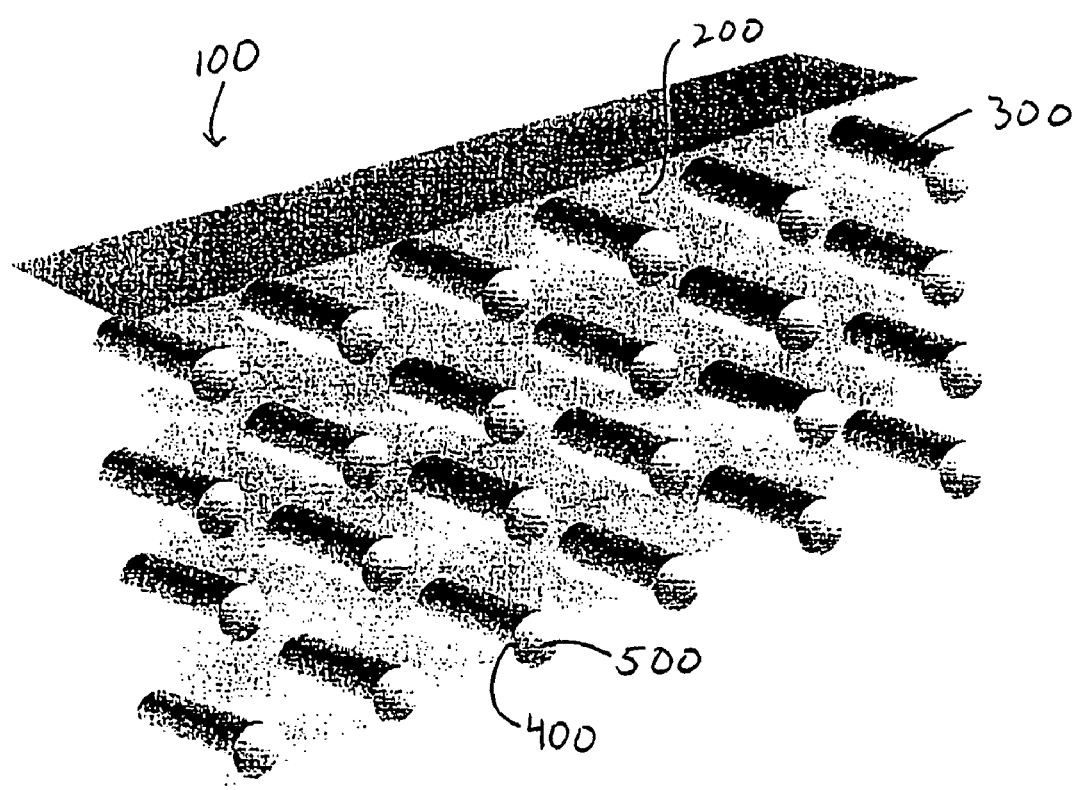
FIG. 43 is a schematic depiction of a plate top of the present invention.

The present invention also provides novel plate top devices for use in conjunction with multiwell (i.e., 8, 16, 24, 96, 364 etc.) plates. In some embodiments, the plate top devices provide anchoring surfaces for mesogens utilized in the assay. Referring to FIG. 43, one embodiment of a plate type device (100) of the present invention comprises a plate top surface (200). A plurality of elongated members (300) extend outwardly from the plate top surface (200). In preferred embodiments the plate top members comprise a distal end (400) having a distal end surface (500). In preferred embodiments, the elongated member (300) is a hollow cylinder. In further preferred embodiments, the distal end (400) is comprised of a optically clear, non-birefringent material (e.g., polycarbonate). In further preferred embodiments, the distal end surface (500) is configured to orient mesogens. Any suitable surface preparation may be used, including, but not limited to, rubbed surfaces, surface with obliquely deposited metals, nano-blasted surfaces.

Figure 44:
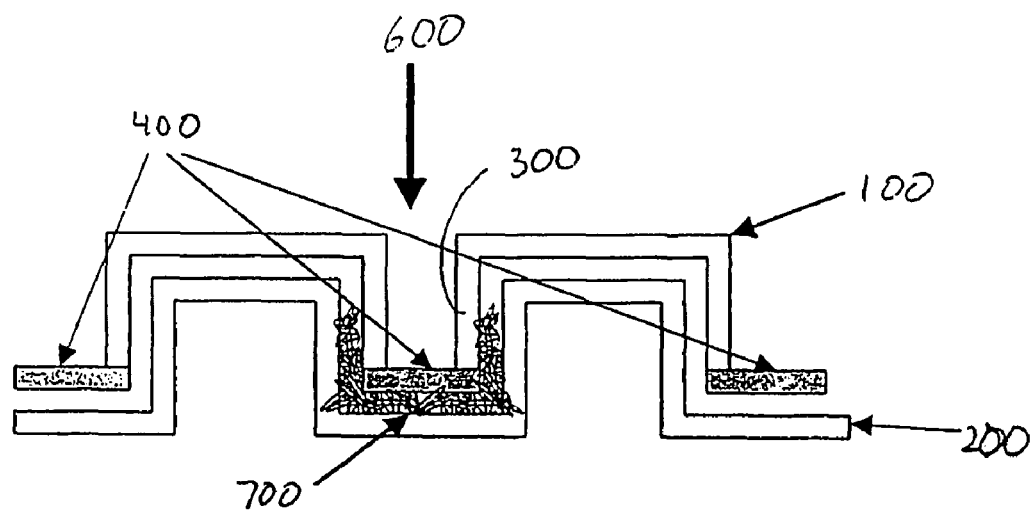
FIG. 44 is a schematic depiction of liquid orientation by the plate top of FIG. 43.

Referring to FIG. 44, the plate top device is placed over a multiwell plate (100, only a portion is shown) having a number of wells (600) equal to the number of elongated members (300) so that each of the elongated members (300) extends into a corresponding well (600). Preferably, the elongated member (300) extends substantially to the bottom of the well (600) so that a thin film of liquid crystal (700) is present between distal end (400) of the elongated member (300). In still other preferred embodiments, the dimensions of the elongated member (300) are only fractionally smaller than the interior dimensions of the wells (600) so that extra liquid crystal mesogens pass upwards along the sides of the elongated members (300) placed in the wells (600). It is contemplated that this arrangement creates uniform contact of the distal end (400) of the elongated member (300) with the liquid crystal film (700).

Figure 45:
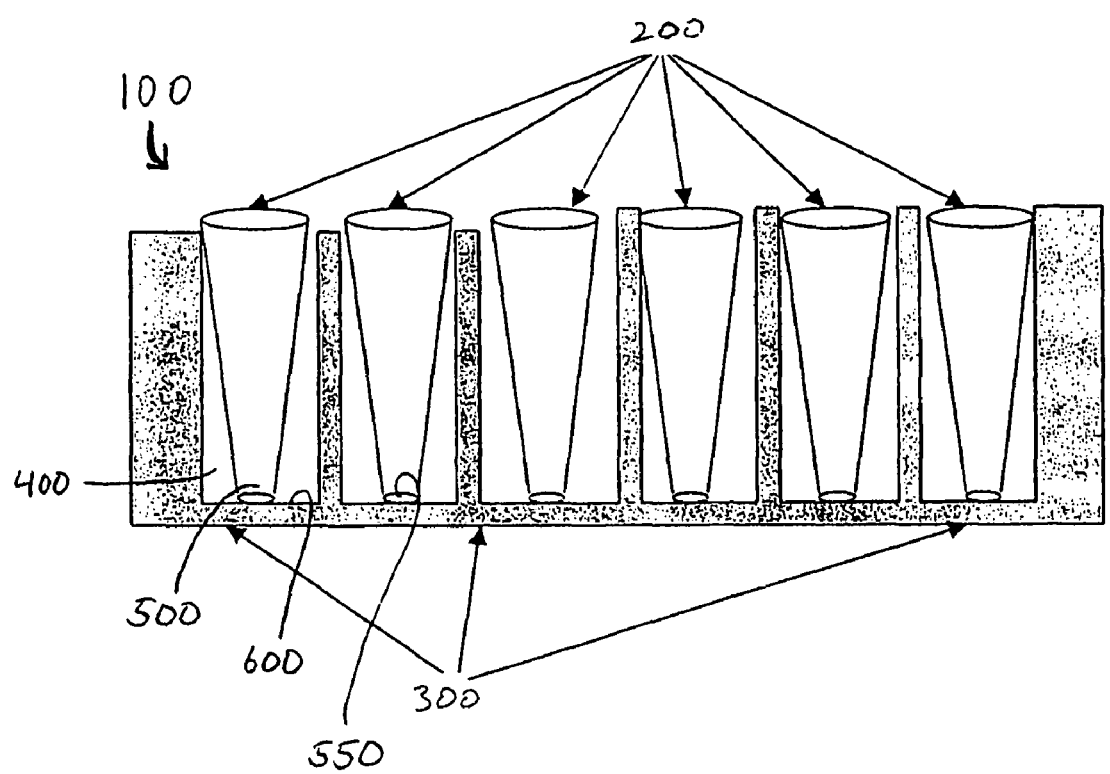
FIG. 45 is a schematic depiction of a plate cover for orienting cells in the center of a well in a multiwell plate.
Figure 46:
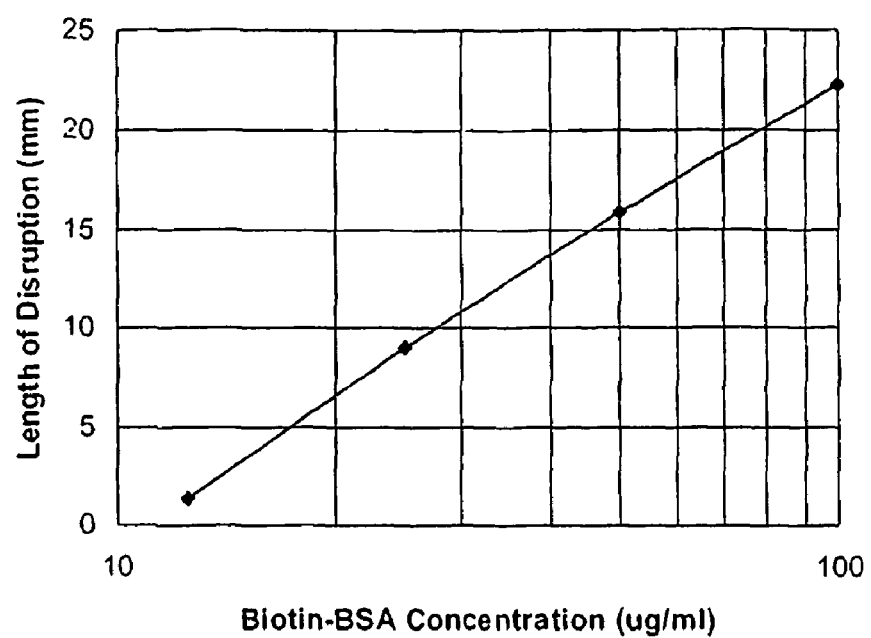
FIG. 46 is a graph depicting results of quantification of an analyte using microfluidic channels and liquid crystals.

The present invention also provides plate tops useful for delivering cells to a predetermined area in a well of a multiwell plate. Referring to FIG. 45, the cell delivery plate top (100) comprises a plurality of elongated members (200) extending downward from a plate top (not shown). When the plate top is placed onto a multiwell plate (300) the elongated members extend into the wells (400) of the multiwell plate so that the distal end (500) of the elongated member (200) contacts the surface (600) of the well (400). In some preferred embodiments, the surface (600) is substantially flat. In other preferred embodiments, the surface of the well (600) has a depression therein. Preferably the distal end (500) comprising an opening (550). In some preferred embodiment, the opening is from about 1-4 mm. In some further preferred embodiments, the edges of the opening 550 are coated with a gasket material, ensuring a tight seal with the surface (600). Non-limiting examples of gasket material include silicone, latex, and petroleum jelly. In other embodiments, the edges of the opening (550) are coated with a hydrophobic material to discourage cell seepage or migration beyond the perimeter of the cylinder opening. In preferred embodiments, the elongated member (200) is hollow so that a solution of cells may be passed through the elongated member (200) to the surface (600). In particularly preferred embodiments, the elongated member (200) is conical in shape. However, the invention is not limited to any particular shape of elongated member (200). For example, the elongated member (200) may be cylindrical and triangular in shape. In further preferred embodiments, the elongated members (200) are oriented with respect to the wells (400) of the multiwell plate (300) so that cells are delivered to the center of the wells (400). The plate tops of the present invention are not limited to any particular material. Indeed, the plate tops may be formed from stainless steel or tissue culture polystyrene.

In use, cells in solution are pipetted into the elongated members (200). The cells are allowed to settle and attach to the surface (600) of the wells (200). After being allowed to attach for a specified period of time (incubation time being determined by cell type and culture conditions), the plate top is removed and non-adherent cells are removed by gentle washing. Culture media is then added to the wells and a standard plate top is placed onto the multiwell plate. In still further embodiments, the plate top devices are used to perform cell invasion assays. In these embodiments, the cells are seeded onto a substrate using the plate top device (or applied by some other method) and allowed to attach. Non-attached cells are rinsed off and the cells are labeled (e.g., with a fluorochrome or vital dye). The substrate is then overlayed with a matrix. The matrix could be an extracellular matrix such as a basement membrane like complex collagen 1 or other extracellular matrices or could be agar. The cells are allowed to incubate. A plate reader is then used as described above in more detail to determine how far the cells have migrated from the original seeding point. In other words, the plate reader can be used to identify the area over which the cells have migrated by detecting the cells labeled cells. This methodology may also be utilized to perform a migration assay, except that no matrix is utilized.

Figure 50:
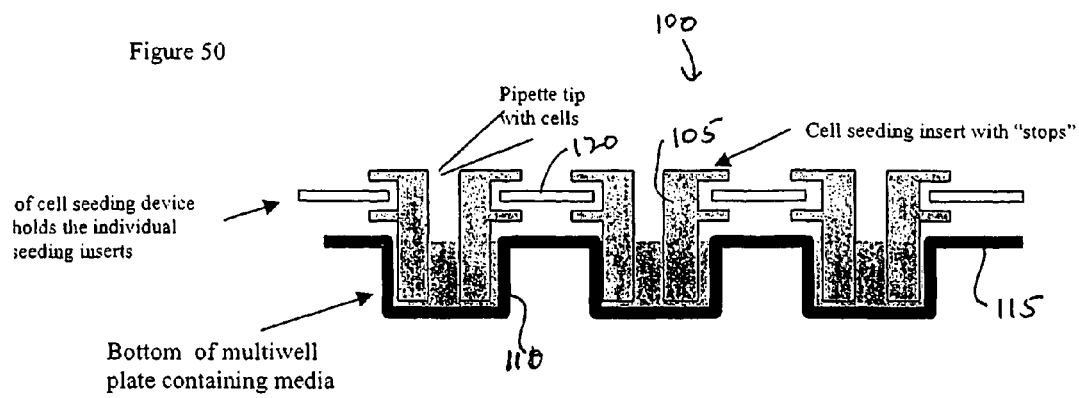
FIG. 50 is a schematic depiction of a device for facilitating the seeding of cells in a multiwell plate.

As shown in FIG. 50, in some embodiments the present invention a device for facilitating the seeding of cells in a well (100) comprising a plurality of cylinders (105) sized to to be inserted into the wells (110) of a multiwell plate (115). In some embodiments, the cylinders (105) are movably connected to at least one horizontal member (120). The device (100) may be positioned over a corresponding multiwell plate (e.g., 115) so that the cylinders (105) extend into the wells (110) and contact the bottom of the wells (110). In some embodiments, the cylinders have vertical freedom or movement, horizontal freedom of movement, or a combination of the two. The device may be configured for use with 6, 12, 24, 36, 96, 384, or 1536 multiwell plates. It will be recognized that the device (as with the other devices and apparatuses described above) may also be configured for use with multiwell plates having other numbers of wells (e.g., between about 6 and about 10,000 wells or more).

Figure 51:
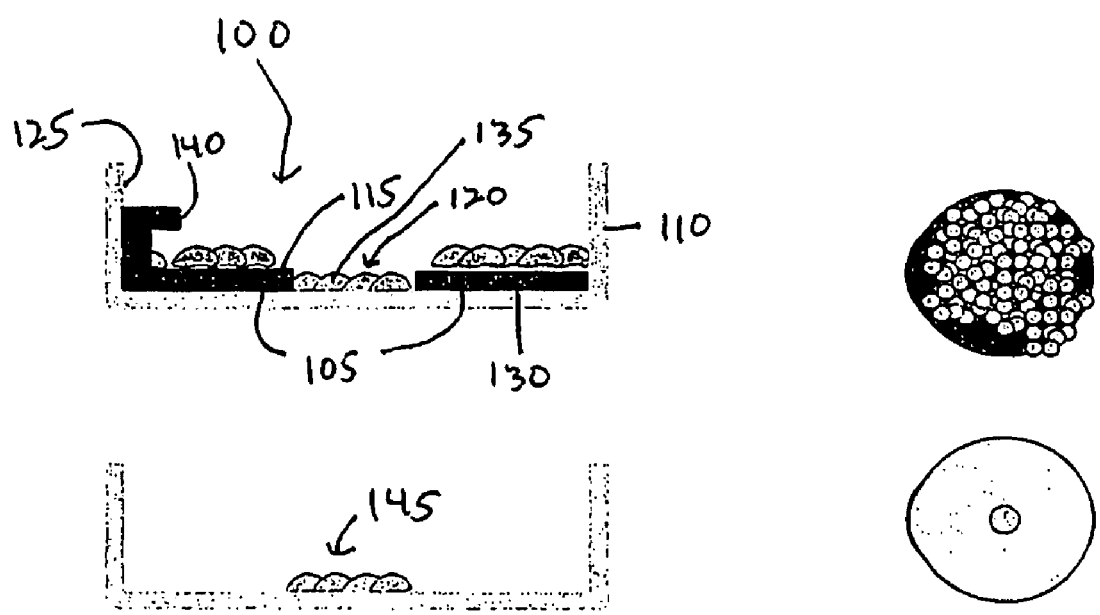
FIG. 51 is a schematic depiction of a device for facilitating the seeding of cells in a multiwell plate.

Referring to FIG. 51, the present invention also provides provides a device (100) for facilitating the seeding of cells in wells of a multiwell plate. In some embodiments, the device (100) comprises an insert (105) sized to be inserted into a well (110). The insert (105) comprises a substantially circular surface (115) having therein an opening (120). When the insert (105) is placed into a well (e.g., 110), the circular surface (115) extends substantially to the sidewall (125) of the well (110). The opening (120) exposes the bottom surface (130) of the well (110) so that when cells (135) are placed in the well (110) they can attach to the bottom surface (130) of the well (110). In some embodiments, the insert (105) further comprises a lift piece (140) so that the insert (105) can be removed from the well (110). The lift piece can be configured in several ways, including as a tab (shown) or as an indent (not shown). When the lift piece is removed, the seeded cells (135) are confined to a predetermined area (145) of the well bottom surface (130). The predetermined area (145) shown is circular, however, the predetermined area can be any shape and located throughout the bottom surface (130) of the well (110). In preferred embodiments, the inserts (105) are configured for use with commercial 6, 12, 24, 96, 384 or 1536 well plates. It will be recognized that the inserts can be configured for use with custom plates and plates with non-circular wells (e.g., oval or rectangular wells).

VIII. Zymography Assays

In still other embodiments, the present invention provides devices and methods that utilize liquid crystals to report the results of zymology assays. In particular, it is contemplated that the liquid crystal assay devices of the present invention can be used to report the action of enzyme on its substrate. In some preferred embodiments, the substrates are patterned or otherwise treated as described above (see, e.g., description relating to collagen, MATRIGEL, and other substrates) so that they orient mesogens. An analyte or sample suspected of containing an analyte (which can be an enzyme that acts on the substrate) is then contacted with the substrate so that the analyte can interact with or act on the substrate. The liquid crystal is then applied to the substrate. Activity by the analyte on the substrate is detected by a lack or order in the liquid crystal.

In other embodiments, an enzymatic substrate is applied to a surface that orients liquid crystal (e.g., a surface onto which gold has been obliquely deposited) so that the placement of the enzymatic substrate on the surface prevents orientation of the liquid crystal. The analyte or sample suspected of containing an analyte is then contacted with the enzymatic substrate so that the analyte can interact with or act on the enzymatic substrate. The liquid crystal is then applied to the enzymatic substrate. Activity by the analyte on the enzymatic substrate is detected by the presence of order in the liquid crystal.

In some embodiments, an enzymatic substrate is covalently immobilized on a surface and then rubbed so that liquid crystals are aligned by the enzymatic substrate. A sample suspected of containing an enzymatic activity specific for the enzymatic substrate is then contacted with the enzymatic substrate. After allowing time for a reaction to occur, a liquid crystal is then applied to the substrate. The presence of an enzyme capable of acting on the enzymatic substrate is evidenced by an absence of liquid crystal alignment. In some preferred embodiments, the enzymatic substrate is present in plurality of analytic zones on a substrate surface. In further preferred embodiments, the samples are transported to the analytic zones via microfluidic channels. In still further embodiments, the degree of loss of liquid crystal alignment is proportional to enzyme content in the sample.

In still other embodiments, enzymatic substrates are nanostamped onto a surface to introduce anisotropy. Action of an enzyme in a sample on the enzymatic substrate causes loss of the anisotropy, which is detected by application of a liquid crystal. It will be recognized that this approach can also be used for creating anisotropy with a recognition moiety such as an immunoglobulin.

The zymographic methods described above find use for the study of a variety enzymes. The methods are not limited to the analysis of one enzymatic substrate at a time. For example, more than one enzymatic substrate may be applied to any given analytic zone. Likewise, the methods are not limited to any particular sample type. In some embodiments, the sample is aqueous. In other embodiments, the sample is a sectioned tissue (e.g., cryosectioned tissue) that is contacted with the analytic zone and allowed to incubate. The sectioned tissue is then removed, the analytic zone rinsed, and imaging is conducted by application of a liquid crystal. The present invention is also not limited to any particular type of analytic zone. In some embodiments, the analytic zones are circular or square. In other embodiments, the analytic zones are microfluidic channels. When the sample is caused to flow through the channel, the amount of enzyme in the channel is proportional to the length along the microfluidic channel in which liquid crystal alignment is disrupted.

In still other embodiments, the sample are partially purified before being applied to the enzyme substrate. For example, where a sample may contain more than one enzyme that is capable of acting on a substrate, a non-target enzyme or enzymes may be removed by passing the sample along a microaffinity column that removes the non-target enzyme(s). In preferred embodiments, the microaffinity column comprising micro- or nano-beads that are coated with antibodies specific for the non-target enzyme(s).

IX. Detection and Analysis of Entities with Lipid Membranes

The present invention finds use in the detection of variety of viruses and entities having lipid membranes. Examples of such entities having lipid membranes include, but are not limited to, viruses, bacteria, liposomes, cells, mycoplasmas, protozoans, fungi and the like. Surprisingly, it has now been discovered that entities having lipid membranes can homeotropically orient mesogens independent of any underlying topography pattern on the substrate (see also, co-pending application Ser. No. 10/897,626, incorporated herein by reference in its entirety). Thus, assay devices can be developed and manufactured without the time consuming and expensive stop of optimizing and fabricating nanostructured surfaces. Homeotropic alignment is observed in the present assays if the entity is either specifically or non-specifically bound to a substrate surface. The assays of the present invention can utilize a variety of recognition moieties to detect a wide variety of viral particles in a wide variety of samples. Furthermore, the assays operate independent of temperature constraints.

The present invention is not limited to the detection of any particular types of cells. Examples of such cells include, but are not limited to, Chinese hamster ovary cells (CHO-K1, ATCC CCl-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); human hepatoma line (Hep G2), and, for example, the following cancerous cells or cells isolated from the following carcinomas: fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrbm's macroglobulinemia, and heavy chain disease.

The present invention provides methods and devices for the detection of viruses and/or entities having a biological membrane in a sample. The device of the present invention can be of any configuration that allows for the contact of a mesogenic layer with an organic layer or inorganic layer (e.g., metal, metal salt or metal oxide). The only limitations on size and shape are those that arise from the situation in which the device is used or the purpose for which it is intended. The device can be planar or non-planar. Thus, it is within the scope of the present invention to use any number of polarizers, lenses, filters lights, and the like to practice the present invention.

Accordingly, in some embodiments, the present invention provides substrates comprising at least one detection region comprising a recognition moiety that binds to or otherwise interacts with a virus or a biological entity having a lipid membrane. In preferred embodiments, the detection regions are discreet and created by arraying at least one recognition moiety on the surface of the substrate. As described above, the inventors have made the surprising discovery that viral particles bound to a virus recognition moiety on a substrate surface provide for the homeotropic orientation of mesogens in a liquid crystal independent of the presence of any other homeotropic director (e.g., surface topography that causes homeotropic orientation) in the detection region. Also, the inventors have surprisingly found that entities with lipid membranes (e.g., cells) also provide for the homeotropic orientation of mesogens independent of the presence of other homeotropic directors. Accordingly, in some preferred embodiments, the detection region does not include structures which homeotropically orient mesogens in a liquid crystal in the absence of virus or entity with a lipid membrane bound to or otherwise interacting with the detection region. In preferred embodiments, the recognition moiety is immobilized on the substrate as described in detail above. In some embodiments, a plurality of recognition moieties are arrayed on the surface of the substrate so that multiplexed assays for a variety of viruses and/or entities having a lipid membrane can be performed simultaneously. In other embodiments, the control regions are included on the substrate that comprise control species immobilized on the surface of the substrate or which provide a site to contact with a control sample containing a known amount of the entity that is being detected.

The devices of the present invention can be used to detect the presence of wide variety of biological entities in a sample, including, but not limited to those described above. Likewise, the devices of the present invention can be used to detect biological entities in a variety of samples. In some embodiments, the biological sample is a biological fluid, tissue homogenate, feces, vesicular fluid, swab of an orifice or tissue, or media in which virus has been cultured or prepared. In some embodiments, the biological fluid is cerebral-spinal fluid, urine, serum, plasma, nasal secretion, sputum, semen or saliva.

In some embodiments, ligands are incorporated to detect a variety of bacteria and pathogens including, but not limited to, sialic acid to detect HIV (Wies et al., Nature 333: 426 [1988]), influenza (White et al., Cell 56: 725 [1989]), chlamydia (Infect. Imm. 57: 2378 [1989]), reovirus, *Streptococcus suis, Salmonella*, Sendai virus, mumps, newcastle, myxovirus, and *Neisseria meningitidis;* 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); β-adrenergic receptor to detect rheovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpesvirus (Kaner et al., Science 248: 1410 [1990]); oligomannose to detect *Escherichia coli*; ganglioside $G_{M}1$ to detect *Neisseria meningitidis;* and antibodies to detect a broad variety of pathogens (e.g., *Neisseria gonorrhoeae, V. vulnificus, V parahaemolyticus, V. cholerae, V. alginolyticus*, etc.).

In some embodiments, a second substrate is provided which is configured opposite the first substrate so that cell is formed. In some embodiments, the second substrate is also arrayed with recognition moieties, while in other embodiments, the second substrate is free of recognition moieties. In some embodiments, the second substrate is blocked to prevent non-specific binding or resists non-specific binding.

In some embodiments, samples suspected of containing a virus or entity having a lipid membrane are allowed to contact a detection region(s) on the first substrate. The sample is allowed to contact the substrate for a period of time (e.g., for about 0.5-24 hours, preferably about 2 to 10 hours, and most preferably about 1.5 to 5 hours). In some embodiments, the substrate is rocked during the incubation period. In some embodiments, flowing incubation, the substrate is washed with a suitable buffer (e.g., PBS). The preceding steps can be performed in the presence or absence of the second substrate. For example, in some embodiments, the sample is applies to the substrate and the incubation and wash steps are performed without assembling a cell. In other embodiments, the cell is assembled and the incubation and wash steps are performed in the cell.

Following the wash step, the cell is constructed if necessary. In some embodiments, mesogens are then added to the cell so that a liquid crystal is formed in the cell. The cell is then incubated for a period of time to allow for a change to occur in the liquid crystal. In some embodiments, the change in the liquid crystal occurs immediately. The present assays operate a variable temperature range. In some embodiments, the incubation is conducted at about 15 to 50 degrees C., preferably from about 22 to 35 degrees C.

Following incubation with the liquid crystal, the cell is assayed for whether a change in the liquid crystal has occurred over one or more of the detection regions. Although many changes in the mesogenic layer can be detected by visual observation under ambient light, any means for detecting the change in the mesogenic layer can be incorporated into, or used in conjunction with, the device. Thus, it is within the scope of the present invention to use lights, microscopes, spectrometry, electrical techniques and the like to aid in the detection of a change in the mesogenic layer. In some embodiments, binding of virus to the virus recognition moiety is detected by a change in the color and texture of the liquid crystal. The present invention is not limited to any particular mechanism of action. Indeed, an understanding of the mechanism of action is not necessary to practice the invention. Nevertheless, it is believed that the change in color and texture is due tilting of the mesogens in the liquid crystal prior to assumption of a homeotropic orientation.

Accordingly, in those embodiments utilizing light in the visible region of the spectrum, the light can be used to simply illuminate details of the mesogenic layer. Alternatively, the light can be passed through the mesogenic layer and the amount of light transmitted, absorbed or reflected can be measured. The device can utilize a backlighting device-such as that described in U.S. Pat. No. 5,739,879, incorporated herein by reference. Light in the ultraviolet and infrared regions is also of use in the present invention.

In some embodiments, the cell is placed in between cross polar lenses and light is passed though the lenses and the cell. Areas of homeotropic orientation appear black, while areas of planar orientation appear bright. Thus, the presence of bound virus is indicated by a black field while areas where no virus is bound are indicated by a bright field.

In some embodiments, the present invention utilizes plate readers to detect changes in the orientation of mesogens upon binding of an analyte. In particular, the present invention includes methods and processes for the quantification of light transmission through films of liquid crystals based on quantification of transmitted or reflected light.

The present invention is not limited to any particular mechanism of action. Indeed, an understanding of the mechanism of action is not required to practice the present invention. Nevertheless, it is contemplated that ordered nanostructured substrates impart order to thin films of liquid crystal placed onto their surface. These ordered films of liquid crystal preserve the plane of polarized light passed through them. If the liquid crystal possesses a well-defined distortion—such as a 90 degree twist distortion—then the liquid crystal will change the polarization of the transmitted light in a well-defined and predictable manner. It is further contemplated that ordered films (e.g., areas of homeotropic orientation) of liquid crystal differentially absorb (relative to randomly ordered films of liquid crystal) specific wavelengths of light.

Accordingly, the present invention contemplates the use of plate readers to detect light transmission through an LC assay device when viewed through cross polars, the transmission of light through an LC assay device illuminated with a suitable wavelength of light, or reflection of light (i.e., polarized light or non-polarized light of specific wavelengths) from the surface of an LC assay device. In particularly preferred embodiments, plate readers are provided that are designed to be used in conjunction with LC assays. Other embodiments of the present invention provide modified commercially available readers such as ELISA readers and fluorometric readers adapted to read LC assays.

In some embodiments, the present invention provides kits for the detection of entities having a lipid membrane. In preferred embodiments, the kits comprise one or more substrates as described in detail above. In further embodiments, the kits comprise a second substrate and materials for assembling a liquid crystal cells. In some embodiments, the kits comprise a vial containing mesogens. In still other embodiments, the kits comprise at least one vial containing a entity having a lipid membrane (e.g., control virus or viruses or cells). In still other embodiments, the kit comprises instructions for using the reagents contained in the kit for the detection of at least one type of entity having a lipid membrane. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510 (k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

X. Quality Control

Figure 53A:
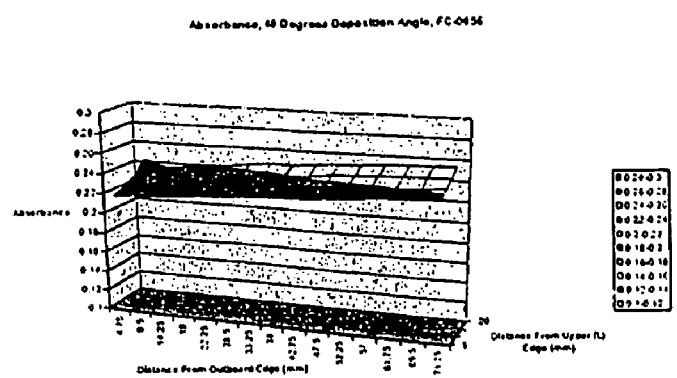
FIG. 53A is a graph of the optical density of various regions of gold-coated aluminosilicate glass slide.
Figure 53B:
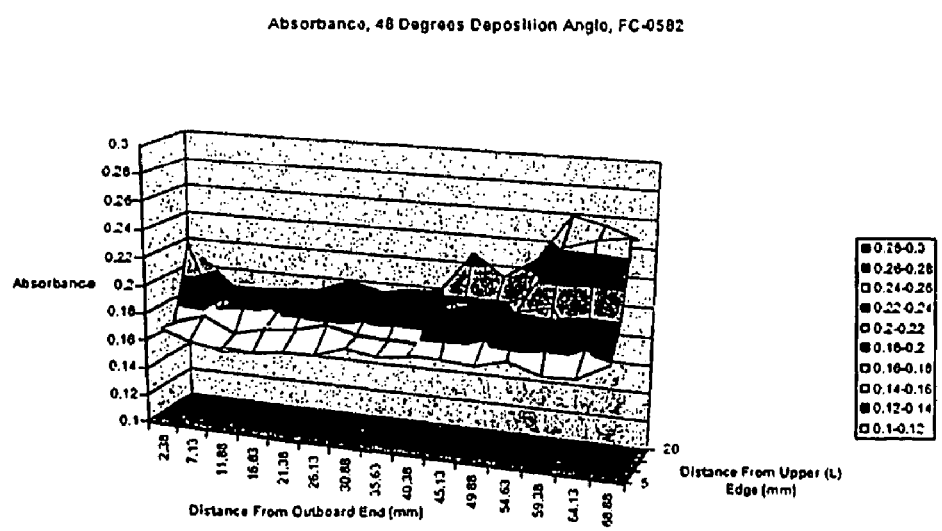
FIG. 53B is a graph of the optical density of various regions of gold-coated soda lime glass slide.

The present invention further provides methods of using plate readers to provide for quality control of coated surfaces (e.g., surfaces coated with gold or some other metal, SAMs, or a polymer). In these embodiments, a plate reader is used to determine the optical density of a coated surface at a plurality of predetermined regions. In some embodiments, the plurality of predetermined regions corresponds to the location of wells in a 6, 12, 24, 96, 384, or 1526 well plate. The optical density of region region is then compared to provide data on the uniformity of the surface. In some embodiments, the degree of uniformity is then compared to a predetermined standard. Surfaces not meeting the predetermined standard are preferably discarded. FIGS. 53a and 53b provide three dimensional plots of optical density of regions of gold coated aluminosilicate (53a) and soda lime (53b) slides. For purposes of determining uniformity, all of the regions can be compared or only a subset of regions may be compared. Moreover, if one region is particularly non-uniform, the entire surface may rejected even though there is good uniformity in all other regions.

EXPERIMENTAL

Example 1

Fabrication of Nanostructured Substrates for use in Cell Assays

Nanostructured substrates that align liquid crystal (LC) for use in LC cell assays have been fabricated using: 1) nanoscale molding, 2) nanoabrasives, 3) obliquely deposited gold films.

Nanomolded substrates were fabricated by the molding of polyurethane and polystyrene from hard masters prepared in silicon. The silicon masters were prepared by electron beam lithography and the topography present in the masters had a width of 200 nm and a height of 50 nm. Studies indicated that immersion of these substrates into aqueous media (phosphate buffered saline) for at least 24 hours does not lead to loss of topography. Furthermore, because of the relatively large scale features, these substrates did not respond (in terms of LC alignment) to non-specific protein adsorption. Polyurethane, micromolded, nanostructured substrates with 50 nm deep tracks were incubated for 4 hrs with cell culture medium (MEM) containing 10% fetal bovine serum. The ability to align LC's was not affected. When viewed with a polarizing microscope, the area within the tracks appeared dark and uniform, while the areas outside of the tracks appeared bright. Sharp lateral resolution of the LC alignment between nanostructured regions and non-structured region of the surface was observed microscopically.

Abraded surfaces were created on glass slides by hand rubbing the slides with a fine commercial emery cloth. Even pressure was applied throughout the rubbing. A liquid crystal film was applied on the surface of the abraded slide and viewed through polarizing filters. The liquid crystal film appeared dark when viewed through crossed polars indicating that the liquid crystals were aligned on the nano-abraded surface. Cell culture medium (MEM) containing 10% fetal calf serum was incubated on the surfaces. A film of LC's was added to the surface. When viewed with polarizing lenses, the LC's were aligned on the surface, indicating that the alignment of LC's is not affected by protein adsorption to the nano-abraded surface.

Obliquely deposited gold films were prepared on glass slides. The gold was deposited from a vapor that impacts the glass slide at an oblique angle of incidence (12.5 degrees). This method leads to a surface with nano-meter scale statistical topography. The slide was incubated with cell culture medium (MEM) containing 10% fetal calf serum. Following the removal of the cell culture medium, a layer of LC was applied and the slide was visualized through polarizing filters. The liquid crystals were aligned on the slide. This demonstrates that such surfaces will be useful in liquid crystal based cellular assays.

Example 2

Liquid Crystals Reliably Report Cell Number

Figure 47:
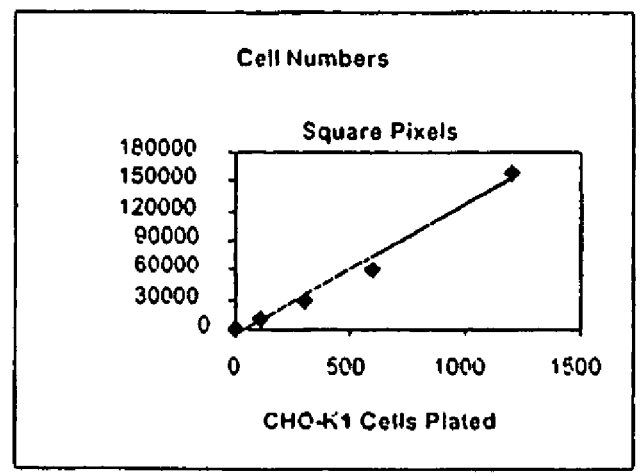
FIG. 47 is a graph depicting results of an experiment to determine cell number with a liquid crystal assay.

CHO K1 cells were seeded in DMSO onto anisotropically ordered nanostructured substrates of obliquely deposited gold that align liquid crystals. The cells were allowed to attach for 4 hours. The media was removed and the cells were fixed in methanol, gluteraldehyde or they were left unfixed. The slides were either dried in a stream of Nitrogen or left wet and then covered with a film of a nematic LC. A variety of LC films, including 5CB, E7 and TL205 were able to accurately report the presence of cells regardless of their state of hydration or method of fixation. Substrates with 100, 300, 600 and 1200 cells per 3.14 mm2 (equivalent to approx 5,600-67,000 cells seeded into a single 15 mm diameter of a 24 well plate) were imaged through polarizing filters and the images were analyzed for gray scale intensity using NIH Image software. The presence of cells locally prevents the LC film from gaining access to the ordering influence of the underlying nanostructured substrate. Regions of the LC film directly overlying cells are therefore disordered and do not preserve the plane of polarization of light. When viewed in a cross polar configuration the amount of light transmitted is therefore proportional to cell number. These data are presented in FIG. 47.

Example 3

Stability of LC Response

It was noted in the experiments conducted with cells, the LC assays provide an unambiguous signal that persists for weeks without appreciable change. This was true of cells that were fixed prior to the addition of LC and to live cells coated with the LC.

Example 4

LC's Do Not Inhibit Cell Mobility

Matrigel (diluted 1:1 with MEM) and LC TL 205 were mixed in equal volumes and the emulsion was applied to a glass slide which was incubated at 37 C for 30 minutes. Hepa-1c1c7 (hepatic rodent cell line) was plated onto the matrix and incubated for 2 hrs. The cells were visualized with a microscope. In the presence of LC TL 205, the cells formed tracks on the Matrigel. This experiment shows that LC 205 is not inhibitory to cellular movement and that imaging of cellular movement on Matrigel by LC's is feasible.

Example 5

Quantification of an Analyte using Microfluidic Channels and Liquid Crystals This example describes the results of an experiment in which disruption of a liquid crystal along a microfluidic channel was used quantify the amount of an analyte in a sample. Five microchannels were (1 mm wide by 25 μm deep) were formed on a block of PDMS that was supported on a glass slide. Samples containing PBS (control) or biotin-bovine serum albumin (BSA) in varying concentrations: 12.5, 25, 50 or 100 μg/ml, were placed into a reservoir and moved into the microchannel by capillary force. The substrate was incubated at 37° C. for 60-90 minutes. After incubation, a vacuum was applied to remove the liquids from the microchannels and reservoirs. The PDMS was then peeled off from the glass slide, rinsed with water, dried in a stream of nitrogen gas and placed onto an OTS treated glass slide. Liquid crystals (E7) were introduced into each microchannel through its reservoir by capillary force. Images of the alignment of liquid crystals inside the microchannels were taken with a polarized microscope.

Liquid crystals assume a homeotropic alignment on the PDMS in the absence of bound protein. This region appears dark and homogenous when viewed through polarizing lenses. When biotin-BSA is present on the surface of the microchannel, the liquid crystal loses its homeotropic alignment. This disruption is evidenced by the transmission of light in the regions where protein is bound. The higher the concentration of protein in the sample, the longer the region of disruption along the microchannel (FIG. 48). The length of the disruption of liquid crystals alignment in the microchannel was measured from the images by using the width of the microchannel (1 mm) as a standard. Additional experiments with higher concentrations of biotin-BSA (6.25-400 μg/ml) showed similar results.

Example 6

Detection of Zymographic Activity by Liquid Crystals

The enzymatic digestion of a protein substrate can be detected by the orientation of a layer of liquid crystals placed upon the substrate following exposure to an enzyme. To demonstrate this, we prepared thin films of obliquely deposited gold (45°) on glass slides. The gold slide was functionalized with a self assembling monolayer of an alkanethiol (2 mM, C16SH). A solution of collagen IV (BD Biosciences, 50 μg/mL) was incubated on the slide for 2 hrs at 37° C. A test sample containing 1 pg total enzyme of activated MMP-9 (Chemicon) in 5 mM Tris buffer with 0.005 IGEPAL, pH 7.5 was added to the surface and incubated for 30 minutes at 37° C. The surfaces were washed with water, dried with a stream of nitrogen and a drop of liquid crystal was placed on the surface. The alignment of the liquid crystal was observed microscopically and the degree of disruption of the liquid crystal alignment was measured using Scion software.

Figure 49:
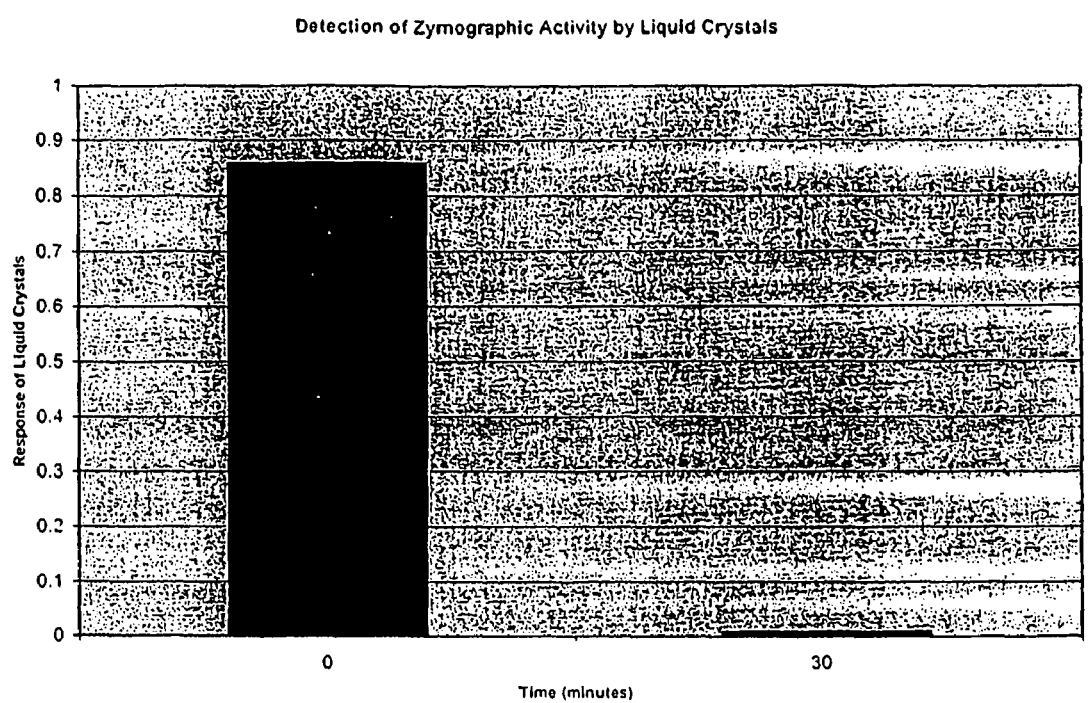
FIG. 49 is graph of the results of a zymography experiment.

Liquid crystals align in a regular fashion on the surfaces prepared with SAM. On surfaces presenting collagen IV, the liquid crystals appear disordered when viewed through a polarizing filter. If MMP-9 digests the collagen IV, the underlying SAM is exposed and liquid crystals align on the SAM. FIG. 49 demonstrates that a surface presenting collagen IV causes disruption in the alignment of the liquid crystal layer (0 min), however, after 30 minutes incubation with 1 pg MMP-9, the collagen IV has been digested and the liquid crystals align on the exposed SAM (30 min).

Example 7

Homeotropic Orientation by Cells

Tables 2 and 3 present the results of experiments in which different liquid crystals were surveyed for their ability to be homeotropically oriented by cultured cells. Many liquid crystals align homeotropically in response to phospholipids and cholesterol. Phospholipids (2 ul; 0.01 M in chloroform) were applied to discrete marked areas on glass slides. The phospholipids had dioleoyl alkyl chains and the following headgroups: phosphatidylserine (DOPS), phosphatidylglycerol (DOPG), phosphatidylethanolamine (DOPE), phosphatidylserine (DOPS), phosphatidic acid (DOPA), and lysophosphatidylcholine (DOLPC). After the solvent dried, optical cells were assembled with liquid crystals applied nematically and heated to isotropy. Homeotropic alignment was confirmed by conoscopic analysis. Chol=cholesterol; C=cholesteric alignment; Bkg=background alignment; U=unaligned; H=homeotropically aligned; ND indicates not done due to background. 4OCB, 4'-octyl-4-biphenyl-carbonitrile (Aldrich); 6CHBT, 1-(trans-4-hexylcyclohexyl)-4-isothiocyanato-benzene. All other liquid crystals are from EM Industries/Merck.

TABLE 2

Survey of liquid crystals for alignment by cells and by slide exposed to medium.

| Liquid Crystal | FBS/DMEM | 3T3 cells |
| --- | --- | --- |
| 4OCB | Disrupted | Homeotropic |
| 5CB | Disrupted | Homeotropic |
| 6CHBT | Planar, with defects | Homeotropic |
| E7 | Disrupted | Homeotropic |
| ZLI-1221 | Planar, streaky | Disrupted |
| ZLI-1557 | Planar with streaky defects | Homeotropic |
| ZLI-2222 | Planar, minor defects | Homeotropic |
| ZLI-3225 | Planar with streaky defects | Homeotropic (tilt) |
| ZLI-3497 | Planar with streaky defects | Homeotropic (tilt) |
| ZLI-4431 | Planar with streaky defects | Homeotropic (tilt) |
| ZLI-4446 | Planar, with defects | Homeotropic |
| ZLI-5070 | Planar with streaky defects | Homeotropic (tilt) |
| MLC-6080 | Planar with squiggly defects | Homeotropic |
| MLC-6466 | Planar with streaky defects | Homeotropic |
| MLC-6710-080 | Planar with streaky defects | Homeotropic |
| MLC-15700-000 | Planar, streaky | Homeotropic |
| TL205 | Somewhat planar | Homeotropic |

TABLE 3

Investigation of phospholipid influence on liquid crystal alignment.

| Liquid Crystal | Bkg | DOPS | DOPG | DOPC | DOPE | DOPA | DOLPC | Chol |
| --- | --- | --- | --- | --- | --- | --- | --- | --- |
| 4OCB | H | ND | ND | ND | ND | ND | ND | ND |
| 5CB | | U | H | H | H | Planar | H | U |
| 6CHBT | | U | H | H | H | H | H | U |
| E7 | | Twisted planar | H | H | H | Twisted planar | H | H |
| ZLI-1221 | | H | H | H | H | H | H | H |

TABLE 3-continued

Investigation of phospholipid influence on liquid crystal alignment.

| Liquid Crystal | Bkg | DOPS | DOPG | DOPC | DOPE | DOPA | DOLPC | Chol |
|---|---|---|---|---|---|---|---|---|
| ZLI-1557 |  | H | H | H | H | H | H | H |
| ZLI-2222 |  | H | H | H | H | H | H | H |
| ZLI-3225 |  | U | H | H | H | H | H | H |
| ZLI-3497 | H | ND | ND | ND | ND | ND | ND | ND |
| ZLI-4431 | Chol | U | U | U | U | U | U | U |
| ZLI-4446 | H | ND | ND | ND | ND | ND | ND | ND |
| ZLI-5070 |  | Twisted planar | H | H | H | H | H | H |
| MLC-6080 |  | U | H | H | H | H | H | H |
| MLC-6466 |  | U | H | H | H | H | H | H |
| MLC-6710-080 |  | U | H | H | H | H | H | H |
| MLC-15700-000 |  | H | H | H | U | H | H | U |
| TL205 |  | U | H | H | H | H | H | H |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in chemical engineering, cell biology, or molecular biology or related fields are intended to be within the scope of the following claims.

We claim:

1. A method for assaying cell movement comprising:
   a) providing:
      i) a multiwell plate comprising a bottom surface;
      ii) an elongated member configured for use with said multiwell plate, said elongated member comprising a surface that contacts the bottom surface of said well and has an opening therein that exposes said bottom surface of said well to constrain cells to a discrete location within said well when said insert is inserted into said well; and
      iii) cells
   b) inserting said elongated member into at least one well of said multiwell plate, wherein said elongated member contacts said bottom surface of said well to define said discrete location on said bottom surface of said at least one well;
   c) seeding said cells in said at least one well in said multiwell plate;
   d) incubating said cells with said elongated member in said at least one well;
   e) removing said elongated member after said cells have attached to said bottom surface of said well, wherein said seeded cells are confined to said discrete location defined by said elongated member
   f) culturing said cells;
   g) assaying said cells for movement from said discrete location.

2. The method of claim 1, wherein said assaying is selected from the group consisting of colorimetric, fluorimetric, optical density, liquid crystal and light scattering assays.

3. The method of claim 2, wherein said assays are read by a plate reader.

4. The method of claim 1, wherein said multiwell plate is selected from the group consisting of 6, 12, 24, 36, 96, 384, or 1536 well plates.

5. The method of claim 1, wherein said at least one well is configured to orient mesogens.

6. The method of claim 1, further comprising the step of contacting said cells with a test compound suspected of promoting or inhibiting movement of said cells.

7. The method of claim 1, wherein said discrete location is circular.

8. The method of claim 1, wherein said wells are partially masked.

* * * * *